(12) United States Patent
Prisco et al.

(10) Patent No.: US 11,207,130 B2
(45) Date of Patent: Dec. 28, 2021

(54) RF ENERGY ENABLED TISSUE DEBRIDEMENT DEVICE

(71) Applicant: Medtronic Xomed, Inc., Jacksonville, FL (US)

(72) Inventors: John R. Prisco, Jacksonville, FL (US); Eric P. Detmers, Jacksonville, FL (US); Wenjeng Li, Saint Johns, FL (US); David J. Little, Ponte Vedra Beach, FL (US); Patrick Richart, Jacksonville, FL (US); Jose Valdez, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 847 days.

(21) Appl. No.: 15/047,242

(22) Filed: Feb. 18, 2016

(65) Prior Publication Data
US 2016/0235469 A1    Aug. 18, 2016

Related U.S. Application Data

(60) Provisional application No. 62/117,523, filed on Feb. 18, 2015.

(51) Int. Cl.
*A61B 18/14* (2006.01)
*A61B 17/32* (2006.01)
(Continued)

(52) U.S. Cl.
CPC .... *A61B 18/1485* (2013.01); *A61B 17/32002* (2013.01); *A61B 18/148* (2013.01);
(Continued)

(58) Field of Classification Search
CPC .......... A61B 17/32002; A61B 17/3207; A61B 17/320758; A61B 17/320783;
(Continued)

(56) References Cited

U.S. PATENT DOCUMENTS

| 2,888,928 A | 6/1959 | Seiger |
| 3,191,084 A | 6/1965 | Ooka et al. |

(Continued)

FOREIGN PATENT DOCUMENTS

| CN | 2323742 Y | 6/1999 |
| CN | 1222065 A | 7/1999 |

(Continued)

OTHER PUBLICATIONS

International Search Report and Written Opinion dated May 3, 2016 for International Application No. PCT/US2016/018486 (12 pgs).

(Continued)

*Primary Examiner* — Eun Hwa Kim
*Assistant Examiner* — Catherine Premraj
(74) *Attorney, Agent, or Firm* — Dicke, Billig & Czaja, PLLC

(57) ABSTRACT

A bipolar electrosurgical device including an outer shaft, an inner shaft, first and second electrode surfaces, and an irrigation channel. The outer shaft defines a lumen, a proximal end and a distal end forming a cutting window. The inner shaft is rotatably disposed within the outer shaft, and defines a distal portion forming a cutting tip. The cutting tip and the cutting window combine to define a cutting implement. The first and second electrode surfaces are electrically isolated, and are formed at the cutting implement. The irrigation channel extends parallel to the outer shaft, and terminates in at least one outlet port. The outlet port is proximally spaced from the cutting window and is located radially outside of the outer shaft. Fluid (e.g., saline) is emitted at the exterior surface of the device near the cutting window and is readily present for interacting with the electrode surfaces.

21 Claims, 58 Drawing Sheets

(51) Int. Cl.
*A61B 18/00* (2006.01)
*A61B 17/3207* (2006.01)

(52) U.S. Cl.
CPC ........... *A61B 17/320783* (2013.01); *A61B 2018/00083* (2013.01); *A61B 2018/00202* (2013.01); *A61B 2018/00208* (2013.01); *A61B 2018/00327* (2013.01); *A61B 2018/00595* (2013.01); *A61B 2018/00601* (2013.01); *A61B 2217/007* (2013.01); *A61B 2218/002* (2013.01); *A61B 2218/007* (2013.01)

(58) Field of Classification Search
CPC ......... A61B 17/320024; A61B 18/148; A61B 18/1482; A61B 18/1485; A61B 18/1487; A61B 18/1492; A61B 2217/007; A61B 2218/002; A61B 2018/1472; A61B 10/0266–0275; A61B 17/320016; A61B 2017/320024; A61B 2017/320032; A61B 2018/00083; A61B 2018/00202; A61B 2018/00327; A61B 2018/00595; A61B 2018/00601; A61B 2218/007
See application file for complete search history.

(56) References Cited

U.S. PATENT DOCUMENTS

| | | |
|---|---|---|
| 3,223,088 A | 12/1965 | Barber et al. |
| 3,682,130 A | 8/1972 | Jeffers |
| 3,750,650 A | 8/1973 | Ruttgers |
| 3,886,944 A | 6/1975 | Jamshidi |
| 3,955,284 A | 5/1976 | Balson |
| 3,955,578 A | 5/1976 | Chamness |
| 4,014,342 A | 3/1977 | Staub |
| 4,060,088 A | 11/1977 | Morrison |
| 4,174,713 A | 11/1979 | Mehl |
| 4,195,637 A | 4/1980 | Gruntzig |
| 4,207,897 A | 6/1980 | Lloyd |
| 4,248,224 A | 2/1981 | Jones |
| 4,651,734 A | 3/1987 | Doss |
| 4,823,791 A | 4/1989 | D'Amelio et al. |
| 4,878,493 A | 11/1989 | Pasternak |
| 4,931,047 A | 6/1990 | Broadwin et al. |
| 4,932,952 A | 6/1990 | Wojciechowicz |
| 4,943,290 A | 7/1990 | Rexroth |
| 4,950,232 A | 8/1990 | Ruzicka |
| 4,985,030 A | 1/1991 | Melzer |
| 4,998,933 A | 3/1991 | Eggers |
| 5,112,299 A | 5/1992 | Pascaloff |
| 5,190,541 A | 3/1993 | Abele |
| 5,195,959 A | 3/1993 | Smith |
| 5,230,704 A | 7/1993 | Moberg |
| 5,234,428 A | 8/1993 | Kaufman |
| 5,254,117 A | 10/1993 | Rigby |
| 5,275,609 A | 1/1994 | Pingleton |
| 5,281,215 A | 1/1994 | Milder |
| 5,282,799 A | 2/1994 | Rydell |
| 5,330,521 A | 7/1994 | Cohen |
| 5,334,181 A | 8/1994 | Rubinsky |
| 5,336,220 A | 8/1994 | Ryan |
| 5,336,443 A | 8/1994 | Odashima |
| 5,352,222 A | 10/1994 | Rydell |
| 5,364,395 A | 11/1994 | West |
| 5,376,078 A | 12/1994 | Dinger |
| 5,383,874 A | 1/1995 | Jackson |
| 5,385,148 A | 1/1995 | Lesh |
| 5,395,312 A | 3/1995 | Desai |
| 5,401,272 A | 3/1995 | Perkins |
| 5,405,348 A | 4/1995 | Anspach |
| 5,405,376 A | 4/1995 | Mulier |
| 5,413,556 A | 5/1995 | Whittingham |
| 5,417,709 A | 5/1995 | Slater |
| 5,431,168 A | 7/1995 | Webster |
| 5,431,649 A | 7/1995 | Mulier |
| 5,441,503 A | 8/1995 | Considine |
| 5,443,463 A | 8/1995 | Stern |
| 5,445,638 A | 8/1995 | Rydell |
| 5,460,629 A | 10/1995 | Shlain |
| 5,490,819 A | 2/1996 | Nicholas |
| 5,492,527 A | 2/1996 | Glowa |
| 5,496,271 A | 3/1996 | Burton |
| 5,505,700 A | 4/1996 | Leone |
| 5,540,562 A | 7/1996 | Giter |
| 5,540,708 A | 7/1996 | Lim |
| 5,542,196 A | 8/1996 | Kantro |
| 5,542,945 A | 8/1996 | Fritzsch |
| 5,556,397 A | 9/1996 | Long |
| 5,560,373 A | 10/1996 | De Santis |
| 5,562,702 A | 10/1996 | Huitema |
| 5,569,243 A | 10/1996 | Kortenbach |
| 5,569,254 A | 10/1996 | Carlson |
| 5,573,424 A | 11/1996 | Poppe |
| 5,595,183 A | 1/1997 | Swanson |
| 5,599,346 A | 2/1997 | Edwards |
| 5,605,539 A | 2/1997 | Buelna |
| 5,609,573 A | 3/1997 | Sandock |
| 5,620,415 A | 4/1997 | Lucey |
| 5,620,447 A | 4/1997 | Smith |
| 5,647,869 A | 7/1997 | Goble |
| 5,676,693 A * | 10/1997 | LaFontaine ........ A61B 18/1485 607/116 |
| 5,685,838 A | 11/1997 | Peters |
| 5,688,267 A | 11/1997 | Panescu |
| 5,697,536 A | 12/1997 | Eggers |
| 5,712,543 A | 1/1998 | Sjostrom |
| 5,713,942 A | 2/1998 | Stern |
| 5,733,280 A | 3/1998 | Avitall |
| 5,743,903 A | 4/1998 | Stern |
| 5,766,167 A | 6/1998 | Eggers |
| 5,792,167 A | 8/1998 | Kablik |
| 5,797,905 A | 8/1998 | Fleischman |
| 5,797,960 A | 8/1998 | Stevens |
| 5,810,764 A | 9/1998 | Eggers |
| 5,810,802 A | 9/1998 | Panescu |
| 5,810,809 A | 9/1998 | Rydell |
| 5,814,044 A | 9/1998 | Hooven |
| 5,827,216 A | 10/1998 | Igo |
| 5,836,947 A | 11/1998 | Fleischman |
| 5,840,030 A | 11/1998 | Petrie |
| 5,843,021 A | 12/1998 | Edwards |
| 5,843,152 A | 12/1998 | Tu |
| 5,849,023 A | 12/1998 | Mericle |
| 5,873,855 A | 2/1999 | Eggers |
| 5,873,886 A | 2/1999 | Larsen |
| 5,891,142 A | 4/1999 | Eggers |
| 5,895,355 A | 4/1999 | Schaer |
| 5,897,553 A | 4/1999 | Mulier |
| 5,899,915 A | 5/1999 | Saadat |
| 5,902,272 A | 5/1999 | Eggers et al. |
| 5,904,681 A | 5/1999 | West, Jr. |
| 5,913,854 A | 6/1999 | Maguire |
| 5,916,150 A * | 6/1999 | Sillman ................. A61B 1/227 600/184 |
| 5,916,213 A | 6/1999 | Haissaguerre |
| 5,921,982 A | 7/1999 | Lesh |
| 5,925,045 A | 7/1999 | Reimels |
| 5,927,284 A | 7/1999 | Borst |
| 5,928,191 A | 7/1999 | Houser |
| 5,935,123 A | 8/1999 | Edwards |
| 5,941,876 A | 8/1999 | Nardella |
| 5,944,715 A | 8/1999 | Goble |
| 5,957,881 A | 9/1999 | Peters |
| 5,957,919 A | 9/1999 | Laufer |
| 5,971,980 A | 10/1999 | Sherman |
| 5,971,983 A | 10/1999 | Lesh |
| 5,980,516 A | 11/1999 | Mulier |
| 5,989,248 A | 11/1999 | Tu |
| 5,993,412 A | 11/1999 | Deily |
| 6,004,316 A | 12/1999 | Laufer |
| 6,004,319 A | 12/1999 | Goble |
| 6,010,476 A | 1/2000 | Saadat |
| 6,010,500 A | 1/2000 | Sherman |
| 6,012,457 A | 1/2000 | Lesh |

(56) References Cited

U.S. PATENT DOCUMENTS

| | | | |
|---|---|---|---|
| 6,015,391 A | 1/2000 | Rishton | |
| 6,024,733 A | 2/2000 | Eggers | |
| 6,042,556 A | 3/2000 | Beach | |
| 6,042,593 A | 3/2000 | Karl | |
| 6,053,923 A * | 4/2000 | Veca | A61B 17/32002 606/79 |
| 6,063,081 A | 5/2000 | Mulier | |
| 6,071,279 A | 6/2000 | Whayne | |
| 6,074,386 A | 6/2000 | Goble | |
| 6,088,894 A | 7/2000 | Oakley | |
| 6,096,037 A | 8/2000 | Mulier | |
| 6,117,101 A | 9/2000 | Diederich | |
| 6,142,993 A | 11/2000 | Whayne | |
| 6,142,994 A | 11/2000 | Swanson | |
| 6,152,920 A | 11/2000 | Thompson | |
| 6,152,941 A | 11/2000 | Himes | |
| 6,161,543 A | 12/2000 | Cox | |
| 6,165,174 A | 12/2000 | Jacobs | |
| 6,193,715 B1 | 2/2001 | Wrublewski | |
| 6,197,024 B1 | 3/2001 | Sullivan | |
| 6,214,003 B1 | 4/2001 | Morgan | |
| 6,217,528 B1 | 4/2001 | Koblish | |
| 6,217,576 B1 | 4/2001 | Tu | |
| 6,217,598 B1 | 4/2001 | Berman | |
| 6,221,088 B1 | 4/2001 | Bays | |
| 6,224,592 B1 | 5/2001 | Eggers | |
| 6,231,518 B1 | 5/2001 | Grabek | |
| 6,235,024 B1 | 5/2001 | Tu | |
| 6,237,605 B1 | 5/2001 | Vaska | |
| 6,238,347 B1 | 5/2001 | Nix | |
| 6,238,393 B1 | 5/2001 | Mulier | |
| 6,245,061 B1 | 6/2001 | Panescu | |
| 6,245,064 B1 | 6/2001 | Lesh | |
| 6,245,065 B1 | 6/2001 | Panescu | |
| 6,246,638 B1 | 6/2001 | Zook | |
| 6,251,092 B1 | 6/2001 | Qin | |
| 6,251,128 B1 | 6/2001 | Knopp | |
| 6,270,471 B1 | 8/2001 | Hechel | |
| 6,292,689 B1 | 9/2001 | Wallace | |
| 6,293,943 B1 | 9/2001 | Panescu | |
| 6,293,957 B1 | 9/2001 | Peters | |
| 6,296,638 B1 | 10/2001 | Davison | |
| 6,325,797 B1 | 12/2001 | Stewart | |
| 6,328,736 B1 | 12/2001 | Mulier | |
| 6,332,881 B1 | 12/2001 | Carner | |
| 6,358,248 B1 | 3/2002 | Mulier | |
| 6,361,531 B1 | 3/2002 | Hissong | |
| 6,364,876 B1 | 4/2002 | Erb | |
| 6,368,275 B1 | 4/2002 | Sliwa | |
| 6,383,151 B1 | 5/2002 | Diederich | |
| 6,385,472 B1 | 5/2002 | Hall | |
| 6,398,792 B1 | 6/2002 | O'Connor | |
| 6,409,722 B1 | 6/2002 | Hoey | |
| 6,413,254 B1 | 7/2002 | Hissong | |
| 6,419,648 B1 | 7/2002 | Vitek | |
| 6,425,867 B1 | 7/2002 | Vaezy | |
| 6,430,426 B2 | 8/2002 | Avitall | |
| 6,440,130 B1 | 8/2002 | Mulier | |
| 6,443,952 B1 | 9/2002 | Mulier | |
| 6,454,782 B1 | 9/2002 | Schwemberger | |
| 6,461,357 B1 | 10/2002 | Sharkey | |
| 6,471,697 B1 | 10/2002 | Lesh | |
| 6,471,698 B1 | 10/2002 | Edwards | |
| 6,474,340 B1 | 11/2002 | Vaska | |
| 6,475,216 B2 | 11/2002 | Mulier | |
| 6,477,396 B1 | 11/2002 | Mest | |
| 6,484,727 B1 | 11/2002 | Vaska | |
| 6,488,678 B2 | 12/2002 | Sherman | |
| 6,488,680 B1 | 12/2002 | Francischelli | |
| 6,494,892 B1 | 12/2002 | Ireland | |
| 6,502,575 B1 | 1/2003 | Jacobs | |
| 6,503,263 B2 | 1/2003 | Adams | |
| 6,514,250 B1 | 2/2003 | Jahns | |
| 6,527,767 B2 | 3/2003 | Wang | |
| 6,537,248 B2 | 3/2003 | Mulier | |
| 6,537,272 B2 | 3/2003 | Christopherson | |
| 6,558,382 B2 | 5/2003 | Jahns | |
| 6,558,385 B1 | 5/2003 | McClurken | |
| 6,565,560 B1 | 5/2003 | Goble | |
| 6,565,561 B1 | 5/2003 | Goble | |
| 6,584,360 B2 | 6/2003 | Francischelli | |
| 6,585,732 B2 | 7/2003 | Mulier | |
| 6,605,084 B2 | 8/2003 | Acker | |
| 6,610,055 B1 | 8/2003 | Swanson | |
| 6,610,059 B1 * | 8/2003 | West, Jr. | A61B 17/32002 606/41 |
| 6,610,060 B2 | 8/2003 | Mulier | |
| 6,613,048 B2 | 9/2003 | Mulier | |
| 6,623,500 B1 | 9/2003 | Cook et al. | |
| 6,645,199 B1 | 11/2003 | Jenkins | |
| 6,648,883 B2 | 11/2003 | Francischelli | |
| 6,656,175 B2 | 12/2003 | Francischelli | |
| 6,663,627 B2 | 12/2003 | Francischelli | |
| 6,663,628 B2 | 12/2003 | Peters | |
| 6,689,131 B2 | 2/2004 | McClurken | |
| 6,699,240 B2 | 3/2004 | Francischelli | |
| 6,702,810 B2 | 3/2004 | McClurken | |
| 6,702,811 B2 | 3/2004 | Stewart | |
| 6,706,038 B2 | 3/2004 | Francischelli | |
| 6,706,039 B2 | 3/2004 | Mulier | |
| 6,716,211 B2 | 4/2004 | Mulier | |
| 6,716,215 B1 | 4/2004 | David | |
| 6,736,810 B2 | 5/2004 | Hoey | |
| 6,752,816 B2 | 6/2004 | Culp | |
| 6,755,827 B2 | 6/2004 | Mulier | |
| 6,764,487 B2 | 7/2004 | Mulier | |
| 6,773,433 B2 | 8/2004 | Stewart | |
| 6,776,780 B2 | 8/2004 | Mulier | |
| 6,780,180 B1 | 8/2004 | Goble | |
| 6,807,968 B2 | 10/2004 | Francischelli | |
| 6,824,550 B1 | 11/2004 | Noriega | |
| 6,827,715 B2 | 12/2004 | Francischelli | |
| 6,849,073 B2 | 2/2005 | Hoey | |
| 6,858,028 B2 | 2/2005 | Mulier | |
| 6,887,238 B2 | 5/2005 | Jahns | |
| 6,899,711 B2 | 5/2005 | Stewart | |
| 6,911,019 B2 | 6/2005 | Mulier | |
| 6,916,318 B2 | 7/2005 | Francischelli | |
| 6,923,803 B2 | 8/2005 | Goble | |
| 6,936,046 B2 | 8/2005 | Hissong | |
| 6,949,097 B2 | 9/2005 | Stewart | |
| 6,949,098 B2 | 9/2005 | Mulier | |
| 6,953,461 B2 | 10/2005 | McClurken | |
| 6,960,205 B2 | 11/2005 | Jahns | |
| 6,962,589 B2 | 11/2005 | Mulier | |
| 6,979,332 B2 | 12/2005 | Adams | |
| 7,052,494 B2 | 5/2006 | Goble | |
| 7,115,139 B2 | 10/2006 | McClurken | |
| 7,150,747 B1 | 12/2006 | McDonald | |
| 7,166,103 B2 | 1/2007 | Carmel | |
| 7,179,255 B2 | 2/2007 | Lettice | |
| 7,229,437 B2 | 6/2007 | Johnson | |
| 7,232,440 B2 | 6/2007 | Dumbauld | |
| 7,237,990 B2 | 7/2007 | Deng | |
| 7,247,155 B2 | 7/2007 | Hoey | |
| 7,247,161 B2 | 7/2007 | Johnston | |
| 7,261,711 B2 | 8/2007 | Mulier | |
| 7,276,074 B2 | 10/2007 | Adams | |
| 7,278,994 B2 | 10/2007 | Goble | |
| 7,309,325 B2 | 12/2007 | Mulier | |
| 7,311,708 B2 | 12/2007 | McClurken | |
| 7,322,974 B2 | 1/2008 | Swoyer | |
| 7,361,175 B2 | 4/2008 | Suslov | |
| 7,364,579 B2 | 4/2008 | Mulier | |
| 7,416,539 B2 | 8/2008 | Johnston | |
| 7,442,191 B2 | 10/2008 | Hovda | |
| 7,537,595 B2 | 5/2009 | McClurken | |
| 7,604,635 B2 | 10/2009 | McClurken | |
| 7,608,072 B2 | 10/2009 | Swanson | |
| 7,645,277 B2 | 1/2010 | McClurken | |
| 7,651,494 B2 | 1/2010 | McClurken | |
| 7,674,263 B2 * | 3/2010 | Ryan | A61B 18/148 606/180 |
| 7,691,050 B2 | 4/2010 | Gellman | |

(56) References Cited

U.S. PATENT DOCUMENTS

| | | | |
|---|---|---|---|
| 7,699,846 B2 | 4/2010 | Ryan | |
| 7,736,361 B2 | 6/2010 | Palanker | |
| 7,749,608 B2 | 7/2010 | Laude | |
| 7,785,337 B2* | 8/2010 | Adams | A61B 17/1688 604/22 |
| 7,811,282 B2 | 10/2010 | McClurken | |
| 7,815,634 B2 | 10/2010 | McClurken | |
| 7,854,736 B2 | 12/2010 | Ryan | |
| 7,909,820 B2 | 3/2011 | Lipson | |
| 7,942,872 B2 | 5/2011 | Ein-Gal | |
| 7,976,544 B2 | 7/2011 | McClurken | |
| 7,993,337 B2 | 8/2011 | Lesh | |
| 7,997,278 B2 | 8/2011 | Utley | |
| 7,998,140 B2 | 8/2011 | McClurken | |
| 8,012,153 B2 | 9/2011 | Woloszko | |
| 8,034,071 B2 | 10/2011 | Scribner | |
| 8,038,670 B2 | 10/2011 | McClurken | |
| 8,048,070 B2 | 11/2011 | O'Brien | |
| 8,083,736 B2 | 12/2011 | McClurken | |
| 8,105,323 B2 | 1/2012 | Buysse | |
| 8,109,956 B2 | 2/2012 | Shadeck | |
| 8,172,828 B2 | 5/2012 | Chang | |
| 8,177,783 B2 | 5/2012 | Davison | |
| 8,202,288 B2 | 6/2012 | Adams | |
| 8,216,233 B2 | 7/2012 | McClurken | |
| 8,277,474 B2 | 10/2012 | Norman et al. | |
| 8,317,786 B2 | 11/2012 | Dahla | |
| 8,323,276 B2 | 12/2012 | Palanker | |
| 8,348,946 B2 | 1/2013 | McClurken | |
| 8,361,068 B2 | 1/2013 | McClurken | |
| 8,377,086 B2 | 2/2013 | Flynn | |
| 8,388,642 B2 | 3/2013 | Muni | |
| 8,414,572 B2 | 4/2013 | Davison | |
| 8,568,419 B2 | 10/2013 | de Wekker | |
| 9,226,792 B2 | 1/2016 | Bloom | |
| 2001/0047183 A1 | 11/2001 | Privitera | |
| 2002/0038129 A1 | 3/2002 | Peters | |
| 2002/0049483 A1 | 4/2002 | Knowlton | |
| 2002/0062131 A1 | 5/2002 | Gallo | |
| 2002/0082643 A1 | 6/2002 | Milla | |
| 2002/0165549 A1 | 11/2002 | Akyaw | |
| 2003/0014050 A1 | 1/2003 | Sharkey | |
| 2003/0032954 A1 | 2/2003 | Carranza | |
| 2003/0045872 A1 | 3/2003 | Jacobs | |
| 2003/0073993 A1 | 4/2003 | Ciarrocca | |
| 2003/0097129 A1 | 5/2003 | Davison | |
| 2003/0144656 A1 | 7/2003 | Ocel | |
| 2003/0165794 A1 | 9/2003 | Matoba | |
| 2003/0191462 A1 | 10/2003 | Jacobs | |
| 2003/0204185 A1 | 10/2003 | Sherman | |
| 2003/0216724 A1 | 11/2003 | Jahns | |
| 2004/0001025 A1 | 1/2004 | Carusillo | |
| 2004/0015106 A1 | 1/2004 | Coleman | |
| 2004/0015219 A1 | 1/2004 | Francischelli | |
| 2004/0024395 A1 | 2/2004 | Ellman | |
| 2004/0044340 A1 | 3/2004 | Francischelli | |
| 2004/0049179 A1 | 3/2004 | Francischelli | |
| 2004/0078069 A1 | 4/2004 | Francischelli | |
| 2004/0082948 A1 | 4/2004 | Stewart | |
| 2004/0087940 A1 | 5/2004 | Jahns | |
| 2004/0092926 A1 | 5/2004 | Hoey | |
| 2004/0111136 A1 | 6/2004 | Sharkey | |
| 2004/0111137 A1 | 6/2004 | Shankey | |
| 2004/0116923 A1 | 6/2004 | Desinger | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0153057 A1* | 8/2004 | Davison | A61B 18/148 606/41 |
| 2004/0167427 A1 | 8/2004 | Quick | |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0243163 A1 | 12/2004 | Casiano | |
| 2004/0267326 A1 | 12/2004 | Ocel | |
| 2005/0010095 A1 | 1/2005 | Stewart | |
| 2005/0033280 A1 | 2/2005 | Francischelli | |
| 2005/0090815 A1 | 4/2005 | Francischelli | |
| 2005/0090816 A1 | 4/2005 | McClurken | |
| 2005/0143729 A1 | 6/2005 | Francischelli | |
| 2005/0165392 A1 | 7/2005 | Francischelli | |
| 2005/0171525 A1 | 8/2005 | Rioux | |
| 2005/0209564 A1 | 9/2005 | Bonner | |
| 2005/0222566 A1 | 10/2005 | Nakahira | |
| 2005/0267454 A1 | 12/2005 | Hissong | |
| 2005/0277970 A1 | 12/2005 | Norman | |
| 2006/0009756 A1 | 1/2006 | Francischelli | |
| 2006/0009759 A1 | 1/2006 | Christian | |
| 2006/0064085 A1 | 3/2006 | Schechter | |
| 2006/0106375 A1 | 5/2006 | Werneth | |
| 2006/0178670 A1 | 8/2006 | Woloszko et al. | |
| 2006/0200123 A1* | 9/2006 | Ryan | A61B 18/148 606/48 |
| 2006/0259055 A1 | 11/2006 | Thorne | |
| 2007/0049920 A1 | 3/2007 | McClurken | |
| 2007/0093808 A1 | 4/2007 | Mulier | |
| 2007/0100336 A1 | 5/2007 | McFarlin et al. | |
| 2007/0118114 A1 | 5/2007 | Miller | |
| 2007/0149965 A1 | 6/2007 | Gallo | |
| 2007/0179495 A1 | 8/2007 | Mitchell | |
| 2007/0208332 A1 | 9/2007 | Mulier | |
| 2008/0015563 A1 | 1/2008 | Hoey | |
| 2008/0042513 A1 | 2/2008 | Kuenzel et al. | |
| 2008/0058796 A1 | 3/2008 | O'Brien | |
| 2008/0071270 A1 | 3/2008 | Desinger | |
| 2008/0132890 A1* | 6/2008 | Woloszko | A61B 18/1402 606/41 |
| 2008/0207028 A1 | 8/2008 | Schutz | |
| 2008/0262489 A1 | 10/2008 | Steinke | |
| 2009/0118729 A1 | 5/2009 | Auth | |
| 2009/0264879 A1 | 10/2009 | Mcclurken | |
| 2009/0270896 A1 | 10/2009 | Sullivan | |
| 2009/0306655 A1 | 12/2009 | Stangenes | |
| 2010/0087812 A1 | 4/2010 | Davison | |
| 2010/0100095 A1 | 4/2010 | McClurken | |
| 2010/0160906 A1 | 6/2010 | Jarrard | |
| 2010/0241178 A1 | 9/2010 | Tilson | |
| 2010/0298763 A1 | 11/2010 | Adams | |
| 2010/0298855 A1* | 11/2010 | Dierck | A61B 17/32002 606/170 |
| 2010/0317998 A1 | 12/2010 | Hibner | |
| 2011/0009856 A1 | 1/2011 | Jorgensen | |
| 2011/0017801 A1 | 1/2011 | Zemlok | |
| 2011/0028965 A1 | 2/2011 | Mcclurken | |
| 2011/0066142 A1 | 3/2011 | Tal | |
| 2011/0137298 A1 | 6/2011 | Nguyen | |
| 2011/0017851 A1 | 7/2011 | Bloom | |
| 2011/0196367 A1 | 8/2011 | Gallo | |
| 2011/0295249 A1 | 12/2011 | Bloom | |
| 2011/0301578 A1 | 12/2011 | Muniz-Medina | |
| 2011/0319889 A1 | 12/2011 | Conley | |
| 2012/0004657 A1 | 1/2012 | Conley | |
| 2012/0012638 A1 | 1/2012 | Huang et al. | |
| 2012/0071712 A1 | 3/2012 | Manwaring | |
| 2012/0101496 A1 | 4/2012 | Mcclurken | |
| 2012/0109130 A1 | 5/2012 | Casey | |
| 2012/0116261 A1 | 5/2012 | Mumaw et al. | |
| 2012/0116397 A1 | 5/2012 | Rencher | |
| 2012/0143293 A1 | 6/2012 | Mauch | |
| 2012/0150165 A1 | 6/2012 | Conley | |
| 2012/0157989 A1 | 6/2012 | Stone | |
| 2012/0172877 A1 | 7/2012 | Ryan | |
| 2012/0179158 A1 | 7/2012 | Stierman | |
| 2012/0184983 A1 | 7/2012 | Chang | |
| 2012/0191084 A1 | 7/2012 | Davison | |
| 2012/0191117 A1 | 7/2012 | Palmer | |
| 2012/0215245 A1 | 8/2012 | Palmer | |
| 2012/0221035 A1 | 8/2012 | Harvey | |
| 2012/0253343 A1 | 10/2012 | McClurken | |
| 2012/0330272 A1 | 12/2012 | Nilsson et al. | |
| 2012/0330292 A1 | 12/2012 | Shadduck | |
| 2013/0004595 A1 | 1/2013 | Bhatia | |
| 2013/0053830 A1 | 2/2013 | Edwards | |

(56) References Cited

U.S. PATENT DOCUMENTS

| | | |
|---|---|---|
| 2013/0085498 A1 | 4/2013 | Matusaitis |
| 2013/0144288 A1 | 6/2013 | Ryan |
| 2013/0331833 A1 | 12/2013 | Bloom |
| 2013/0345704 A1 | 12/2013 | Palmer |
| 2014/0005700 A1 | 1/2014 | Casey |
| 2014/0100567 A1* | 4/2014 | Edwards .......... A61B 17/32002 606/42 |
| 2014/0132126 A1 | 5/2014 | Vicars et al. |
| 2014/0155888 A1 | 6/2014 | Edwards |
| 2014/0155889 A1 | 6/2014 | Edwards |
| 2014/0155923 A1 | 6/2014 | Edwards |
| 2014/0207217 A1 | 7/2014 | Lischinsky et al. |
| 2014/0276808 A1 | 9/2014 | Gittard et al. |
| 2014/0277036 A1 | 9/2014 | Flynn |
| 2015/0265337 A1 | 9/2015 | Bloom |
| 2016/0235468 A1 | 8/2016 | Prisco et al. |
| 2016/0235474 A1 | 8/2016 | Prisco et al. |
| 2017/0143406 A1 | 5/2017 | Bloom |

FOREIGN PATENT DOCUMENTS

| | | |
|---|---|---|
| CN | 103096828 B | 7/2016 |
| EP | 1201196 | 5/2002 |
| EP | 1853187 | 11/2007 |
| EP | 2044893 | 4/2009 |
| EP | 2133028 | 12/2009 |
| GB | 247060 | 12/2010 |
| WO | WO1996/037156 | 11/1996 |
| WO | WO1997/023169 | 7/1997 |
| WO | WO1998/034550 | 8/1998 |
| WO | WO1998/038932 | 9/1998 |
| WO | WO2003/079911 | 10/2003 |
| WO | WO2011/037664 | 3/2011 |
| WO | WO2012/102838 | 8/2012 |
| WO | 2013/191811 | 12/2013 |
| WO | WO2014/084983 | 6/2014 |
| WO | WO2014/133663 | 9/2014 |

OTHER PUBLICATIONS

Non-Final Office Action for U.S. Appl. No. 15/046,853 dated Apr. 12, 2018 (38 pages).
Non-Final Office Action for U.S. Appl. No. 15/046,869 dated Mar. 28, 2018 (29 pages).
Non-Final Office Action for U.S. Appl. No. 14/951,697 dated Jul. 12, 2018 (40 pages).
Non-Final Office Action for U.S. Appl. No. 14/951,697 dated Jan. 23, 2019 (25 pages).
Non-Final Office Action for U.S. Appl. No. 15/046,853 dated Oct. 25, 2018 (39 pages).
Notice of Allowance for U.S. Appl. No. 15/046,869 dated Oct. 9, 2018 (23 pages).
Notice of Allowance for U.S. Appl. No. 15/046,853 dated Apr. 3, 2019 (11 pages).
Non-Final Office Action for U.S. Appl. No. 14/951,697 dated Jul. 25, 2019 (15 pages).

* cited by examiner

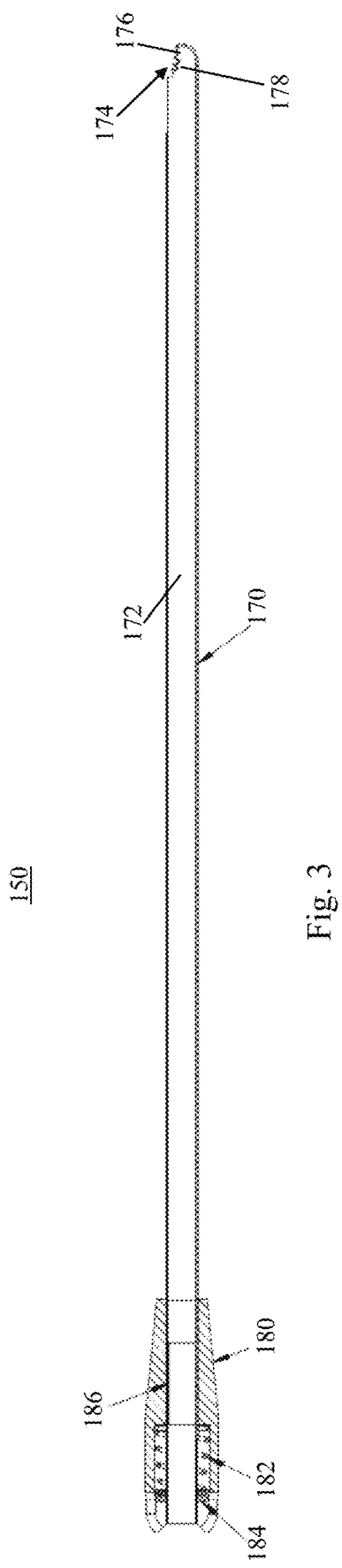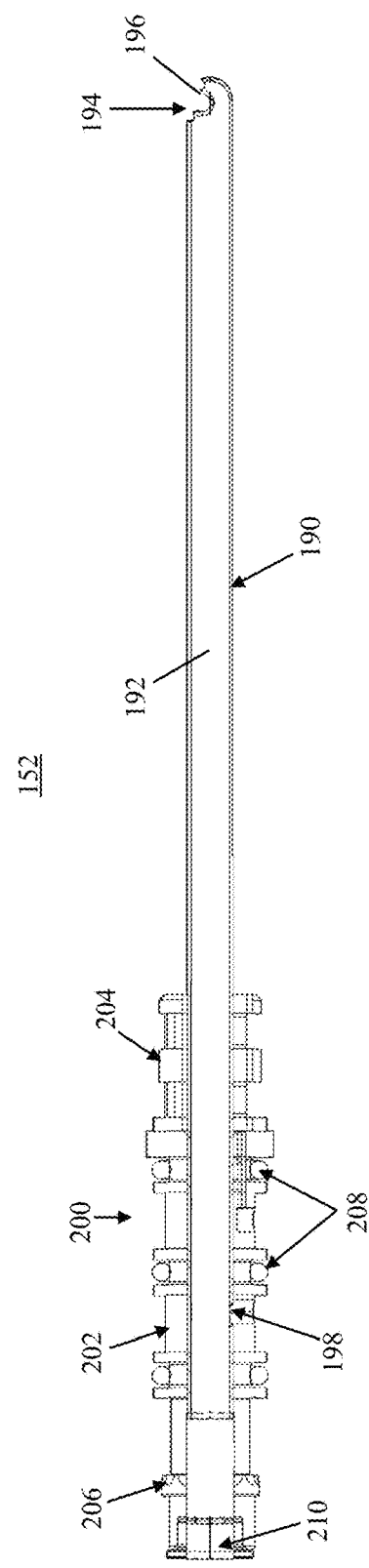
Fig. 3
Fig. 4

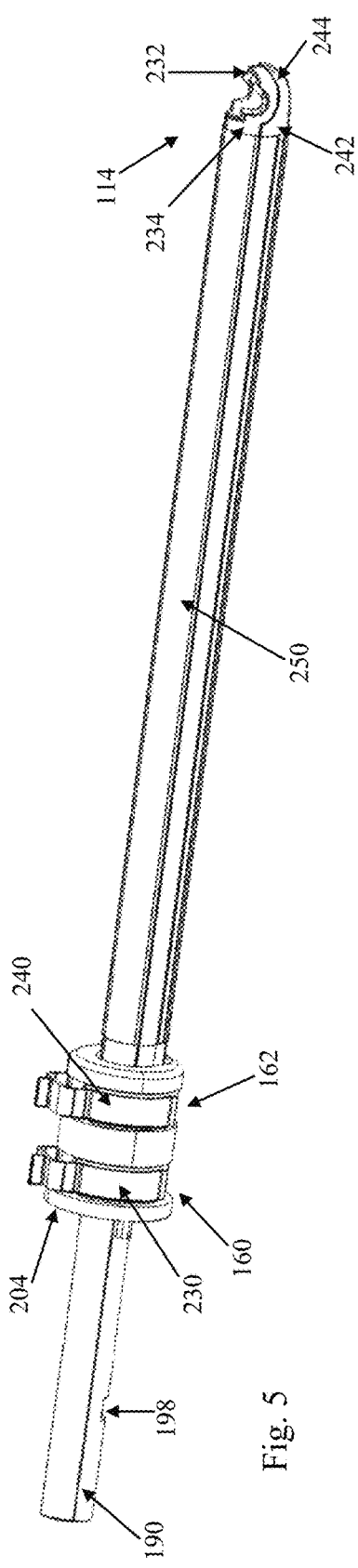
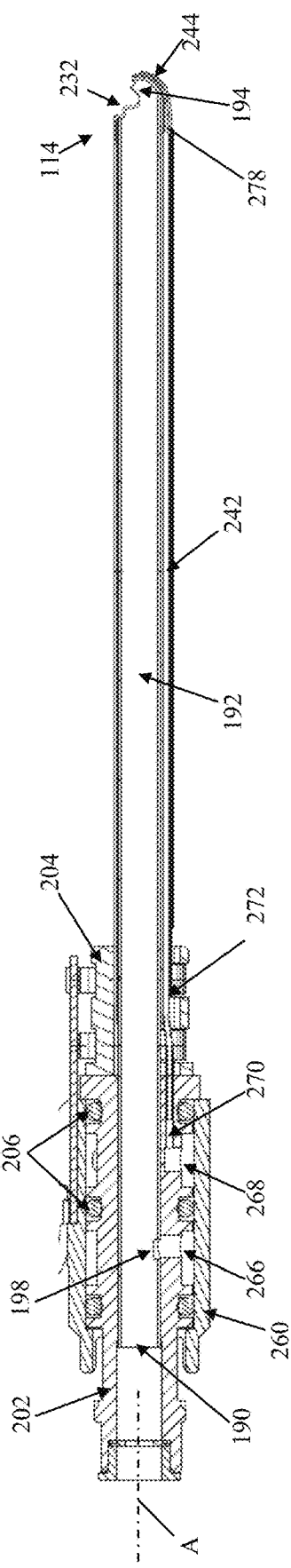
Fig. 5
Fig. 8

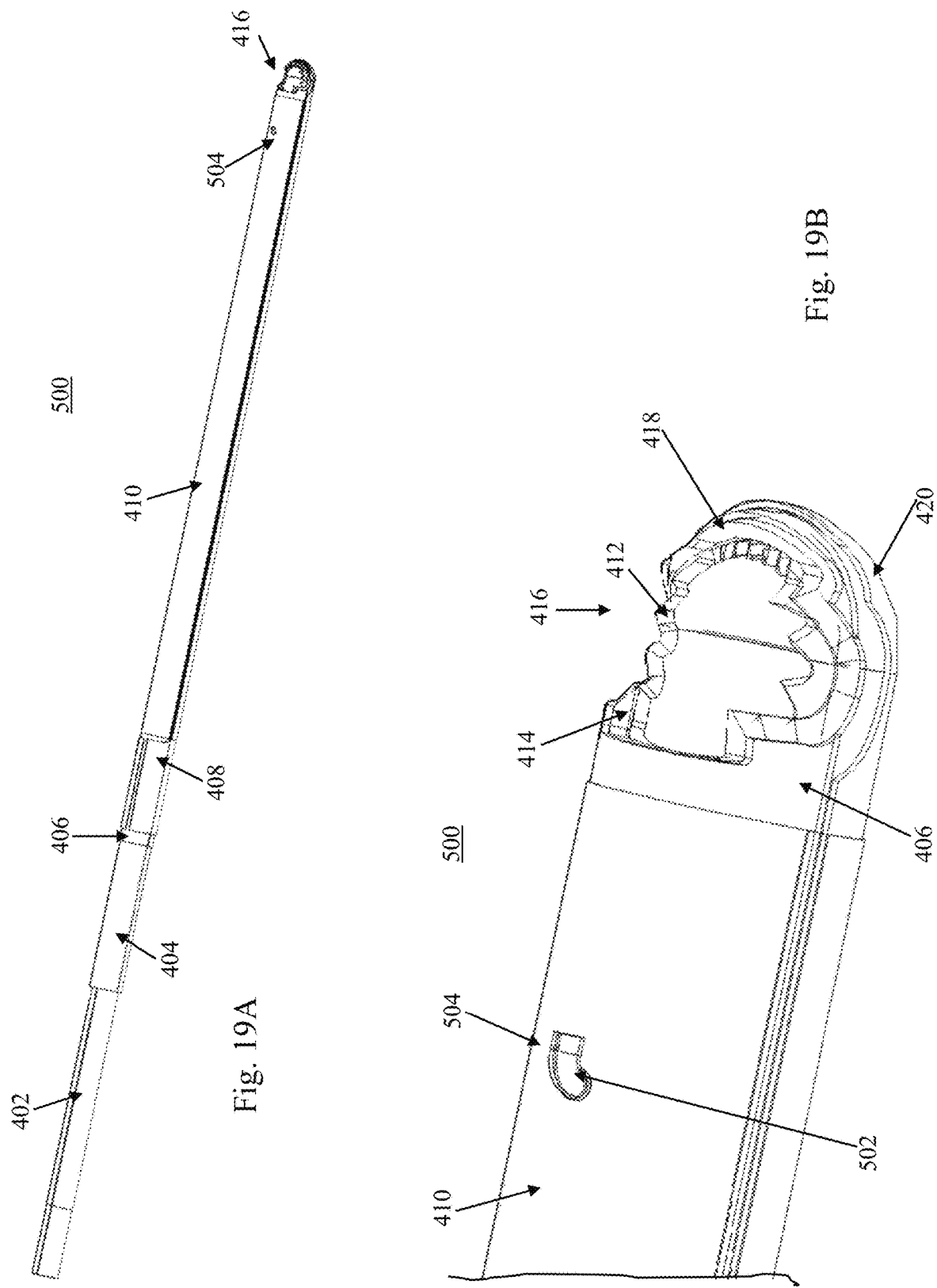

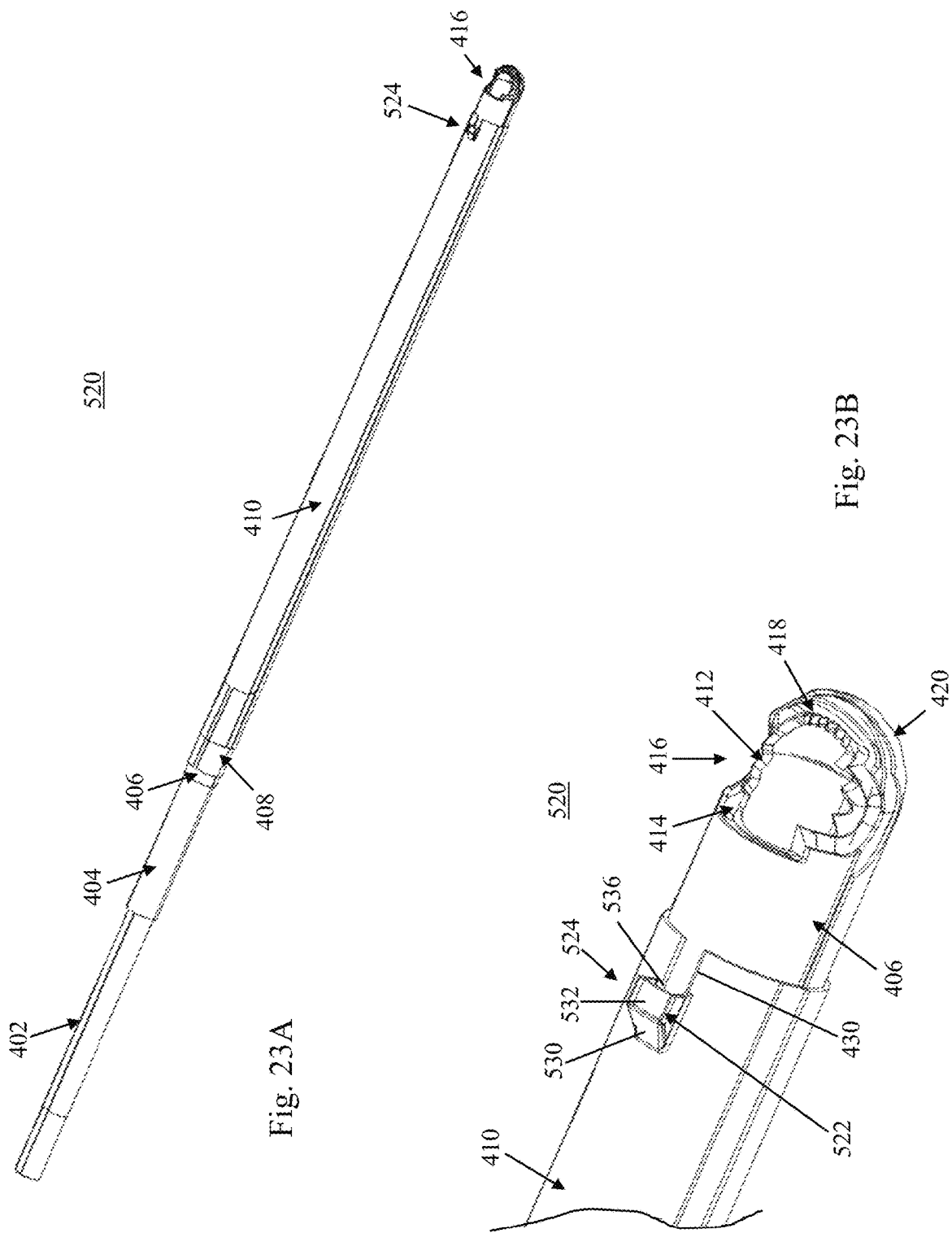

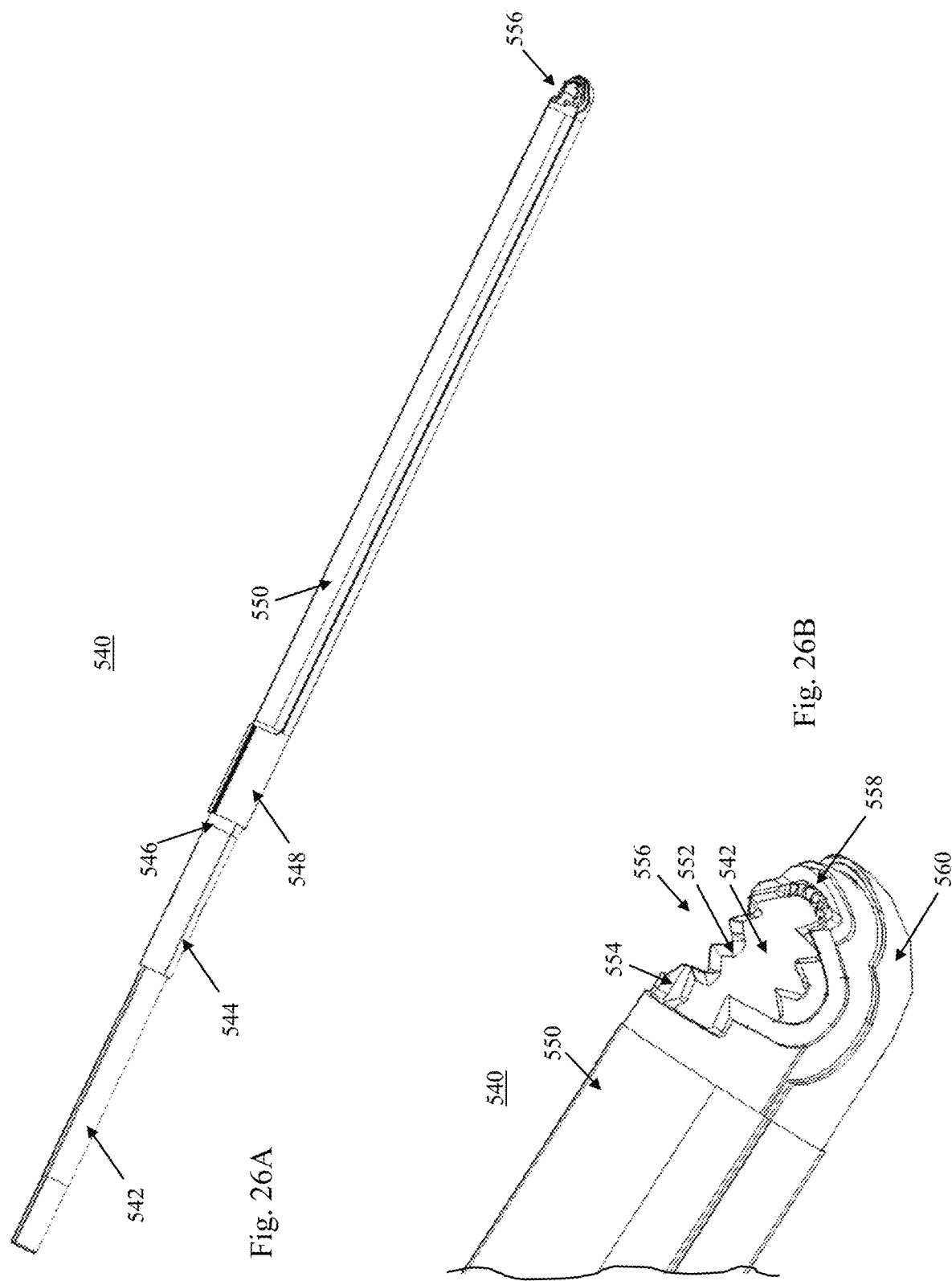

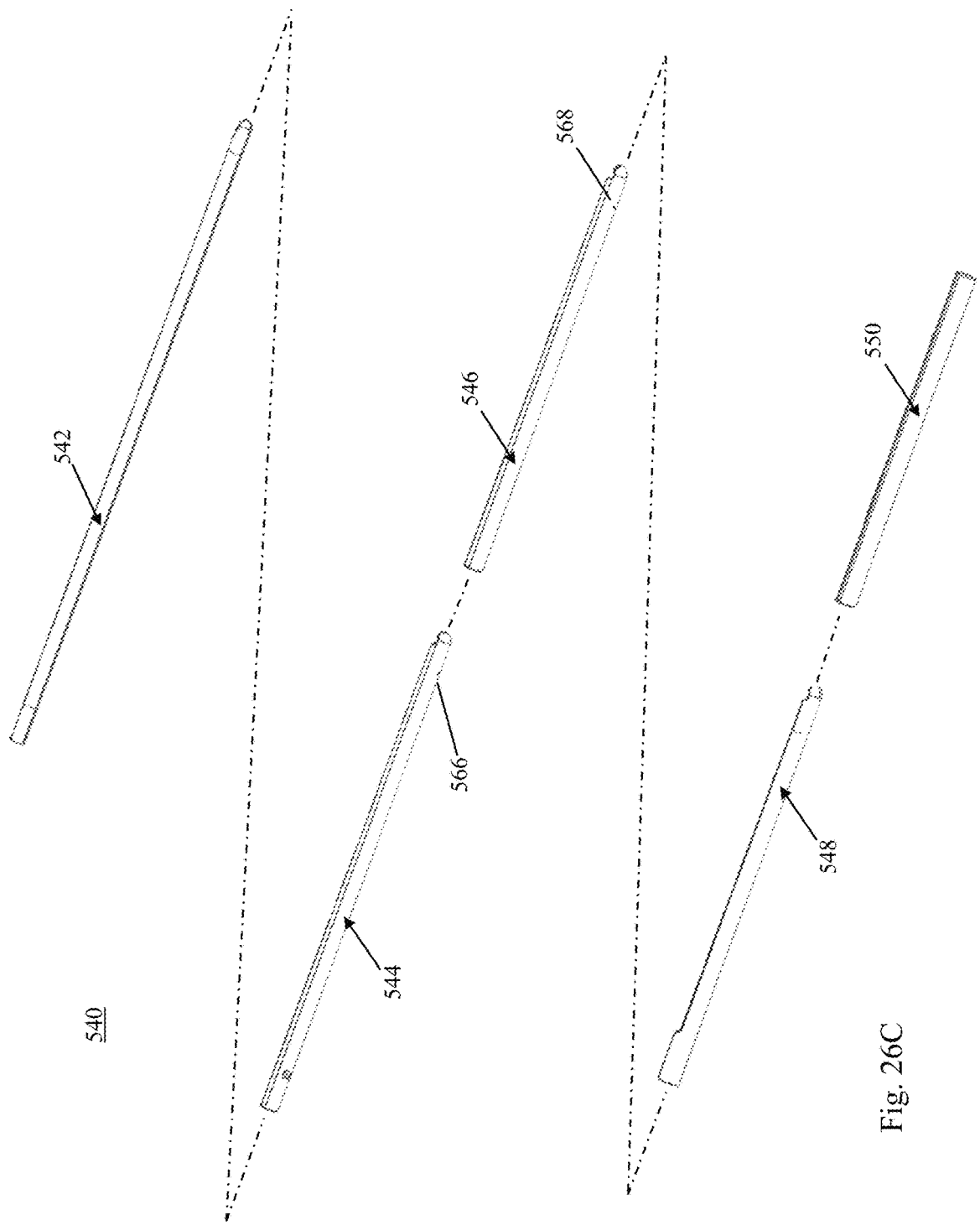

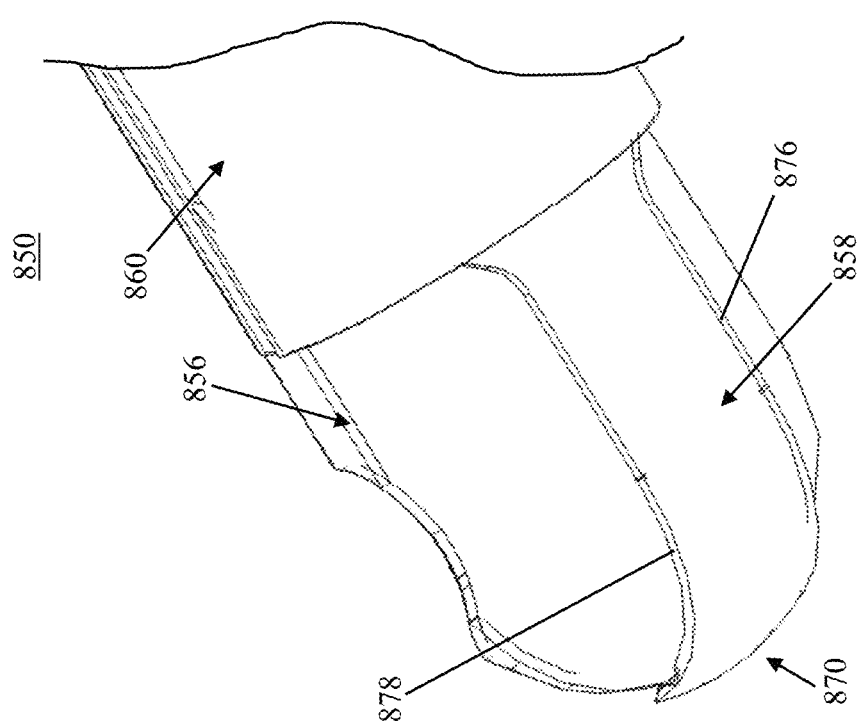
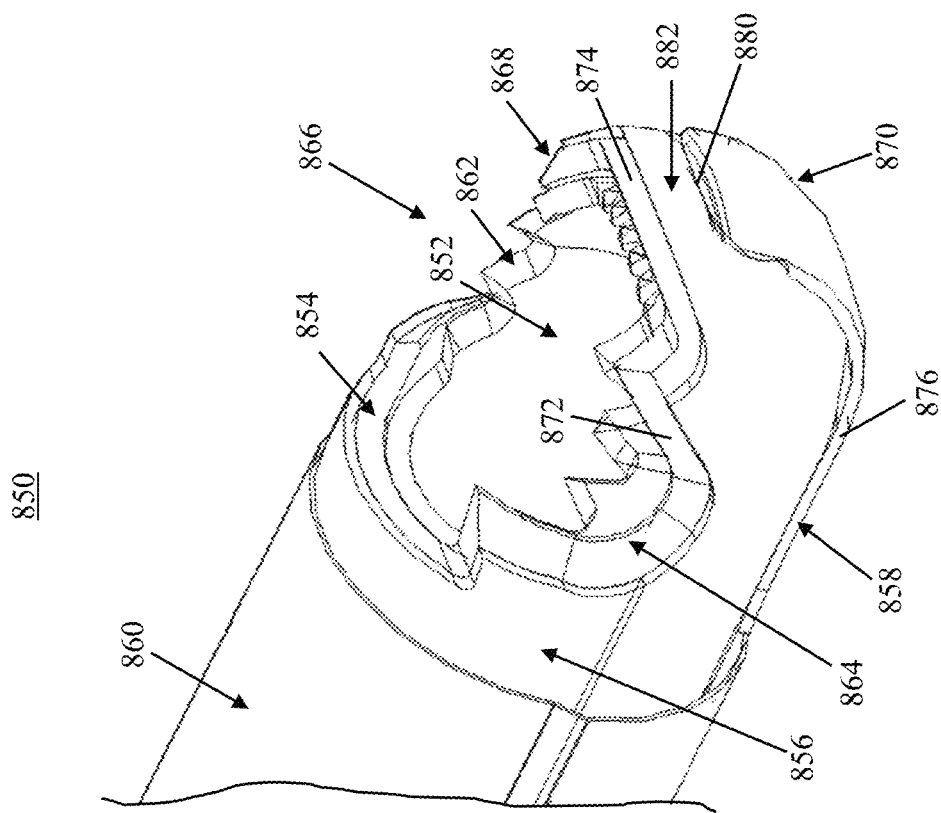
Fig. 46A
Fig. 46B

RF ENERGY ENABLED TISSUE DEBRIDEMENT DEVICE

BACKGROUND

This Non-Provisional Patent Application claims the benefit of the filing date of U.S. Provisional Patent Application Ser. No. 62/117,523, filed Feb. 18, 2015, entitled "IRRIGATION FOR RF ENERGY ENABLED TISSUE DEBRIDEMENT DEVICE," which is herein incorporated by reference.

BACKGROUND

This disclosure is generally directed to devices, systems and methods for cutting and sealing tissue such as bone and soft tissue. The concepts presented herein may be particularly suitable for sinus applications and nasopharyngeal/laryngeal procedures and may combine or provide Transcollation® technology with a microdebrider device.

Devices, systems and methods according to the present disclosure may be suitable for a variety of procedures including ear, nose and throat (ENT) procedures, head and neck procedures, otology procedures, including otoneurologic procedures. The present disclosure may be suitable for a varient of other surgical procedures including mastoidectomies and mastoidotomies; nasopharyngeal and laryngeal procedures such as tonsillectomies, trachael procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and transsphenoidal procedures; rhinoplasty and removal of fatty tissue in the maxillary and mandibular regions of the face.

Sinus surgery is challenging due to its location to sensitive organs such as the eyes and brain, the relatively small size of the anatomy of interest to the surgeon, and the complexity of the typical procedures. Examples of debriders with mechanical cutting components are described in U.S. Pat. Nos. 5,685,838; 5,957,881 and 6,293,957. These devices are particularly successful for powered tissue cutting and removal during sinus surgery, but do not include any mechanism for sealing tissue to reduce the amount of bleeding from the procedure. Sealing tissue is especially desirable during sinus surgery which tends to be a complex and precision oriented practice.

Current approaches to sealing tissue include utilizing Transcollation® technology, where sealing energy is supplied by the Aquamantys® System (available from Medtronic Advanced Energy of Portsmouth, N.H.), which stops bleeding and reduces blood loss during and after surgery. The technology uses a combination of radiofrequency (RF) energy and saline to provide hemostatic sealing of soft tissue and bone, which may lower transfusion rates and reduce the need for other blood management products during or after surgery. Transcollation® technology integrates RF energy and saline to deliver controlled thermal energy to tissue. Coupling of saline and RF energy allows a device temperature to stay in a range which produces a tissue effect without the associated charring found in other ablation methods.

Other ablation devices include mechanical cutting as well as cauterization or electrocautherization energy. For example, the PK diego® powered dissector is commercially available from Gyms ENT of Bartlett, Tenn. This device utilizes two mechanical cutting blade components that are moveable relative to each other, one of which acts as an electrode in a bipolar cauterization system. While providing cauterization and cutting, this device limits effectiveness in delivery of fluid during electrical energy delivery.

SUMMARY

A bipolar electrosurgical device including an outer shaft, an inner shaft, first and second electrode surfaces, and an irrigation channel. The outer shaft defines a lumen extending along a central axis, a proximal end and a distal end opposite the proximal end. The distal end forms a cutting window open to the lumen. The inner shaft is rotatably disposed within the lumen of the outer shaft about the central axis. The inner shaft defines a distal portion forming a cutting tip. The cutting tip and the cutting window combine to define a cutting implement. The first and second electrode surfaces are electrically isolated from one another, and are formed at the cutting implement. The irrigation channel extends parallel to the outer shaft, and terminates in at least one outlet port. The outlet port is proximally spaced from the cutting window and is located radially outside of the outer shaft. With this construction, fluid (e.g., saline) is emitted at the exterior surface of the device near the cutting window and is readily present for interacting with the electrode surfaces, for example promoting bipolar energization at the electrode surfaces. In contrast to conventional electrocautery debrider constructions in which the fluid (e.g., saline) is emitted between the inner and outer shaft, with the devices of the present disclosure, the delivered fluid is not immediately aspirated.

BRIEF DESCRIPTION OF THE DRAWINGS

FIG. 3 is a cross-sectional view of an inner shaft assembly portion of the device of FIG. 2A.

FIG. 4 is a cross-sectional view of an outer shaft assembly portion of the device of FIG. 2A.

FIG. 5 is an isometric view of first and second electrode assembly portions of the device of FIG. 2A.

FIG. 8 is a cross-sectional view of a portion of the device of FIG. 2A, including an irrigation hub and associated irrigation pathways.

FIG. 19A is a perspective view of a portion of another bipolar electrical surgical device in accordance with principles of the present disclosure.

FIG. 19B is an enlarged, perspective view of a portion of the device of FIG. 19A.

FIG. 23A is a perspective view of a portion of another bipolar electrical surgical device in accordance with principles of the present disclosure.

FIG. 23B is an enlarged, perspective view of a portion of the device of FIG. 23A.

FIG. 26A is a perspective view of a portion of another bipolar electrical surgical device in accordance with principles of the present disclosure.

FIG. 26B is an enlarged, perspective view of a portion of the device of FIG. 26A.

FIG. 26C is an exploded, perspective view of the device of FIG. 26A.

FIG. 46A is an enlarged, top perspective view of a portion of another bipolar electrical surgical device in accordance with principles of the present disclosure.

FIG. 46B is a bottom perspective view of the device of FIG. 46A.

DETAILED DESCRIPTION

Figure 1:
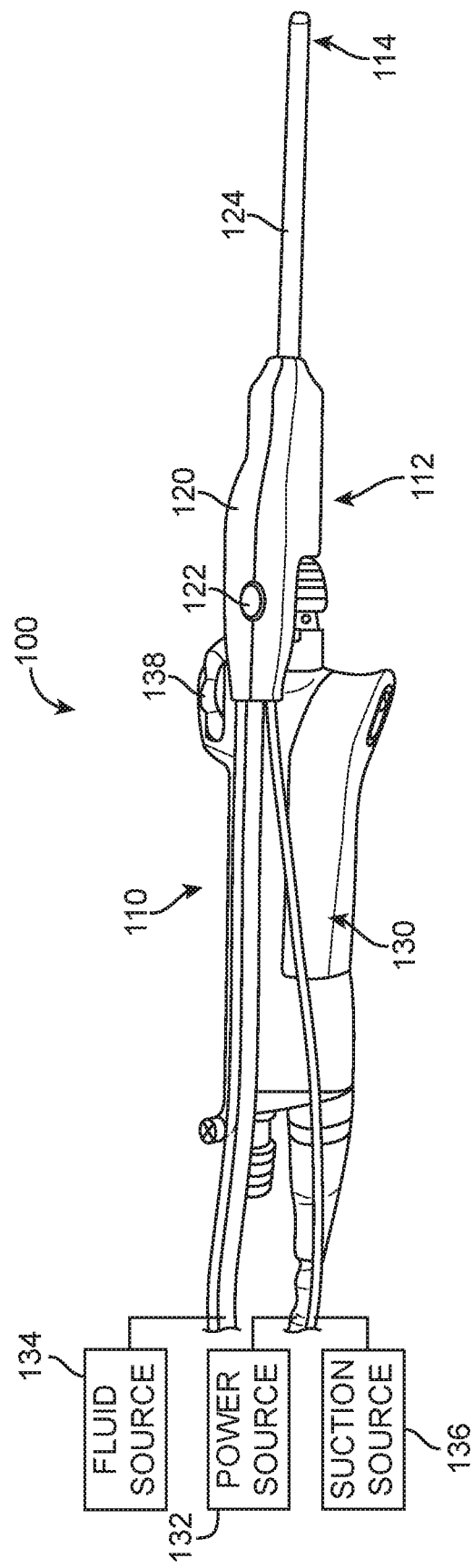
FIG. 1 is a schematic view of a system including a bipolar electrical device.

FIG. 1 illustrates a system 100 that includes a bipolar electrical device 110 having a proximal end region indicated generally at 112 and a distal end region indicated generally at 114. The proximal end region 112 includes a housing 120 maintaining a button 122. A blade assembly 124 extends from the housing 120 to the distal end region 114. As discussed in more detail below, the blade assembly 124 maintains a cutting implement and an electrode assembly to mechanically cut and cauterize or electrocauterize tissue, respectively.

The system 100 further includes a handpiece 130, a power source 132, a fluid source 134 and a suction source 136. It will be appreciated that the power source 132, the fluid source 134 and the suction source 136 can be formed of one or more separate sources as desired and not limited to a single source. The device 110 is configured to couple to the handpiece 130, which can be manipulated by a user (e.g., a surgeon) during operation of the system 100 to cut and cauterize or electrocauterize tissue. In one embodiment, in order to cut tissue, the handpiece 130 includes a motor (not shown) internal to the handpiece 130 that is coupled with the power source 132. The motor is rotationally coupled with the blade assembly 124 to provide mechanical cutting. The handpiece 130 further includes an actuator 138 external to the handpiece 130 that can be used for manual rotation of one or more components of the device 110 relative to the housing 120 and the handpiece 130.

The power source 132 can further be coupled with the device 110 to deliver electrical energy through the blade assembly 124 to the distal region 114. For example, the power source 132 can include a generator and optionally may be designed for use with bipolar energy or a bipolar energy supply. For example, the Transcollation® sealing energy supplied by the Aquamantys® System (available from Medtronic Advanced Energy of Portsmouth, N.H.) may be used.

Fluid can be provided to the distal region 114 through the fluid source 134 connected directly to the device 110 and/or to the device 110 through the handpiece 130. One fluid useful with the present disclosure is saline, however, other fluids are contemplated. The suction source 136 can be coupled to the handpiece 130. Use of fluid in conjunction with energy delivery aids in providing optimal tissue effect, thus embodiments of the present disclosure include specific arrangement of the device 110 for coupling of energy with a fluid. In use, a fluid (e.g., saline) may be emitted from one or more opening(s) at or adjacent the distal end region 114 of the device 110. Tissue fragments and fluids can be removed from a surgical site through an opening in the distal end region 114 via the suction source 136, as will be further explained below. Both the fluid source 134 and suction source 136 are optional components of the system 100.

Figure 2A:
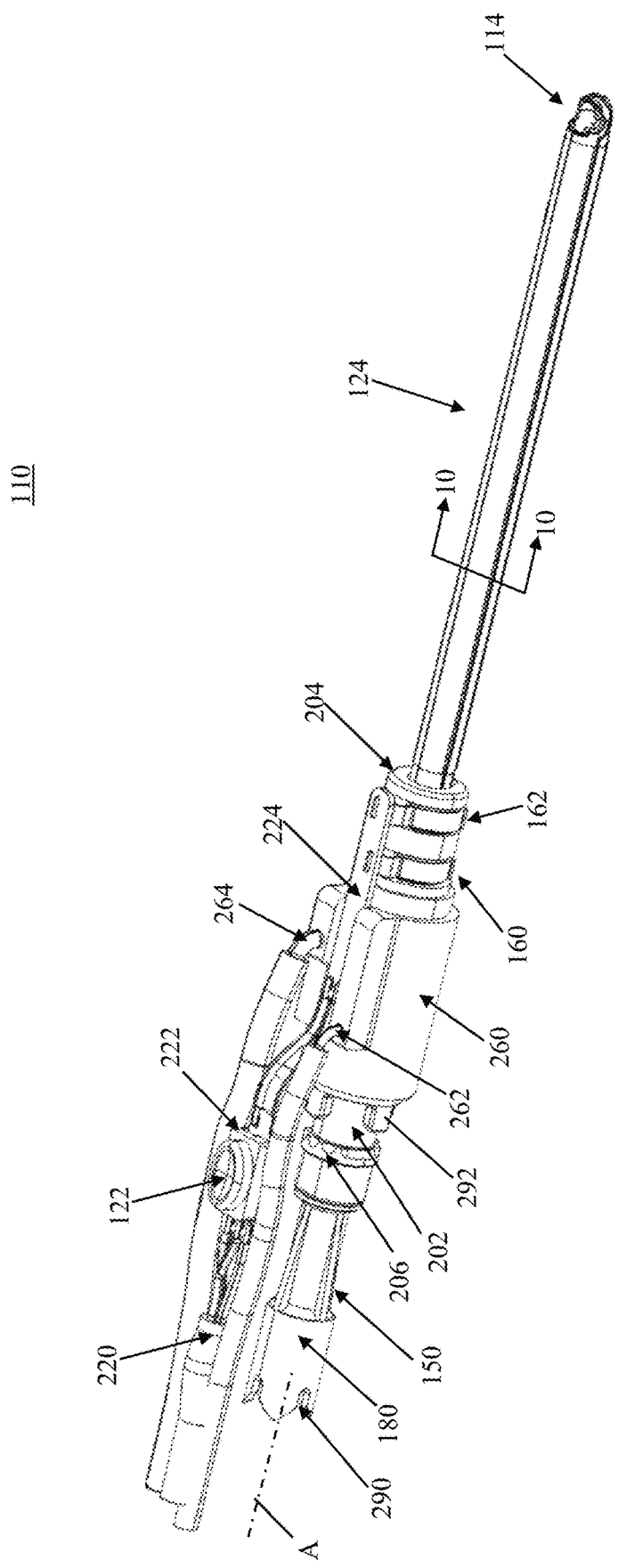
FIG. 2A is an isometric view of a bipolar electrical device of the system of FIG. 1 with a housing portion removed.
Figure 2B:
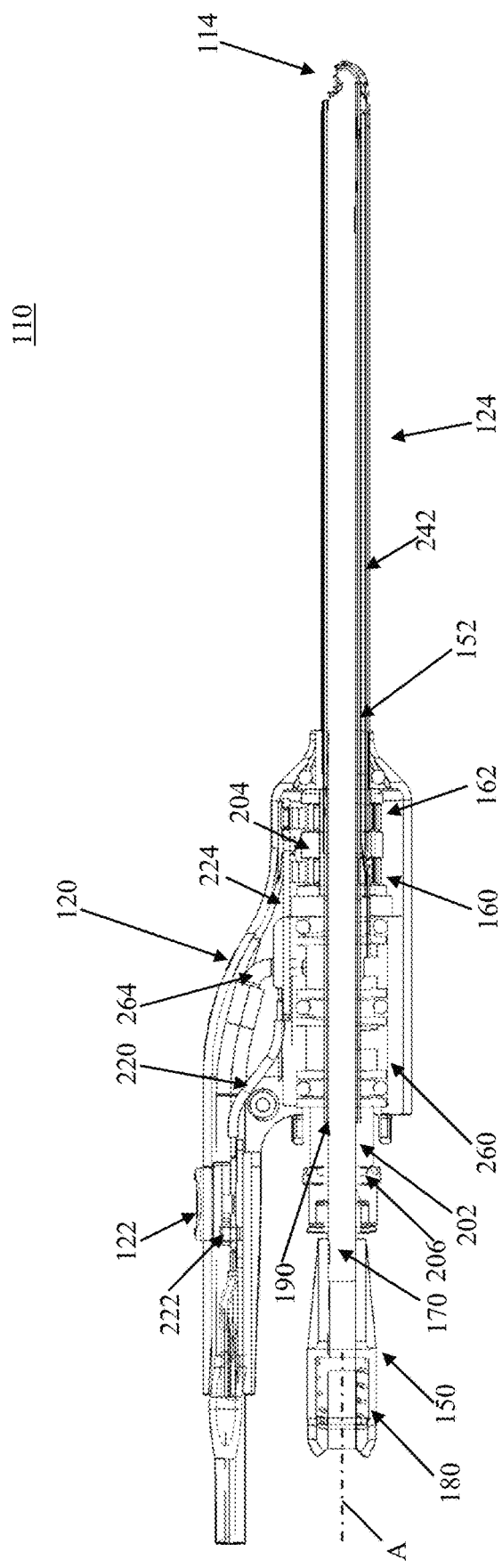
FIG. 2B is a cross-sectional view of the bipolar electrical device of the system of FIG. 1.

With further reference to FIGS. 2A and 2B, an isometric view of the device 110 with the housing 120 removed (FIG. 2A) and a cross section (FIG. 2B) of the device 110 are provided. Details for operation of the device 110 are provided below. In general, the device 110, and in particular the blade assembly 124, includes an inner shaft assembly 150 rotatably disposed within an outer shaft assembly 152 (referenced generally in FIG. 2B) about a central rotational axis A. Upon final assembly, the device 110 is operable with the handpiece 130 (FIG. 1) to provide mechanical cutting due to rotation between the inner shaft assembly 150 and the outer shaft assembly 152. Further details of the inner shaft assembly 150 and the outer shaft assembly 152 are provided below in relation to FIGS. 3 and 4, respectively. In addition to mechanical cutting, the device 110 is operable to provide energy to tissue through a first electrode assembly 160 and a second electrode assembly 162 due to, or in response to, operation of the button 122, further described below with respect to FIG. 5. Also during operation, the device 110 can provide irrigation to the distal end region 114, for example interior to the outer shaft assembly 152 and/or exterior to the outer shaft assembly 152, as discussed below with respect to the non-limiting embodiments of FIGS. 6 and 7. Moreover, a user, through operation of the actuator 138 (FIG. 1), can rotate the outer shaft assembly 152 with respect to the housing 120 and/or the inner shaft assembly 150 so as to alter an orientation of the outer shaft assembly 152 with respect to tissue of interest, as further discussed with respect to FIGS. 8A and 8B.

With further reference to the cross section of FIG. 3, the inner shaft assembly 150 includes a first tubular member (also can be referred to as an inner shaft or inner blade) 170 defining a lumen 172 and a cutting tip 174. In one embodiment, the cutting tip 174 defines a serrated edge 176 including teeth surrounding an opening 178 (referenced generally in FIG. 3) that is fluidly connected to the lumen 172. Alternatively, the cutting tip 174 can assume a variety of other forms. In one embodiment, the first tubular member 170 is formed of a rigid material, such as 304 stainless steel, and is linear in longitudinal extension. Alternatively, the first tubular member 170 can be configured to effectuate bending thereof, such as by a flexible coupling (not shown). A hub 180 coupled to the first tubular member 170 is adapted for connection to the motor of the handpiece 130 (FIG. 1). The motor provides rotational power to the inner shaft assembly 150. The inner shaft assembly 150 further includes a biasing member 182 disposed within the hub 180. Upon final assembly, the biasing member 182 biases the cutting tip 174 into contact with the outer shaft assembly 152. A cap 184 retains the biasing member 182 within the hub 180 and also creates a fluid seal to the suction source 136 (FIG. 1). In one embodiment, the lumen 172 is fluidly coupled with the suction source 136 to provide aspiration of tissue that is cut by the cutting tip 174. The first tubular member 170 is optionally secured to the hub 180 by an adhesive, as indicated generally in FIG. 3 at 186.

As illustrated in the cross section of FIG. 4, the outer shaft assembly 152 includes a second tubular member (also can be referred to as an outer shaft or outer blade) 190 defining a lumen 192 and a cutting window 194. The cutting window 194, in one embodiment, is defined by a serrated edge 196. In one embodiment, the second tubular member 190 is rigid and longitudinally straight or linear and formed by 304 stainless steel. In alternative embodiments, the second tubular member 190 can incorporate, or be forced to assume, one or more bends. Regardless, the second tubular member 190, and in particular the lumen 192, is sized to co-axially receive the first tubular member 170 in a manner that allows rotation and/or oscillation of the first tubular member 170 relative to second tubular member 220 about rotational axis A (FIG. 2B), and optionally to provide a path for internal irrigation. To this end, the lumen 192 of the second tubular member 190 has a diameter slightly greater than an outer diameter of a corresponding portion of the first tubular member 170, and defines an irrigation inlet 198 fluidly connected to the lumen 192 in some embodiments.

A hub assembly 200 is provided with the outer shaft assembly 152 and includes a first, proximal hub member 202 and a second, distal hub member 204. The hub assembly 200, including the first hub member 202 and the second hub member 204, is connected to the second tubular member 190 in a fixed manner so as to rotate together. As such, rotation of the hub assembly 200 causes rotation of the cutting window 194. The hub assembly 200 is adapted for connection to the actuator 138 (FIG. 1) in order to rotate the outer shaft assembly 152, and thus the cutting window 194, relative to the housing 120 (FIG. 1) and the inner shaft assembly 150. In particular, the first hub member 202 can include an engagement member 206 (e.g., gear teeth) that directly couples with a complementary drive member (e.g., a gear) of the actuator 138 to effectuate rotation of the first hub member 202 and, due to the fixed coupling with between the hub assembly 200 and the second tubular member 190, the cutting window 194. A plurality of o-rings 208 are coupled to the first hub member 202 to provide seals for the first hub member 202, as discussed below. In addition, a cap 210 is provided at a proximal end of the outer shaft assembly 152.

Returning to FIGS. 2A and 2B, the device 110 further includes wiring 220 electrically connected with the power source 132 (FIG. 1). The wiring 220 extends to a button activation assembly 222 that controls flow of electrical energy between the wiring 220 and a printed circuit board (PCB) 224 upon operation of the button 122. The PCB 224 is coupled with the first and second electrode assemblies 160 and 162. The electrode assemblies 160 and 162 are electrically isolated from one another so as to provide bipolar electrical energy delivery to tissue positioned proximate the distal region 114.

Figure 6A:
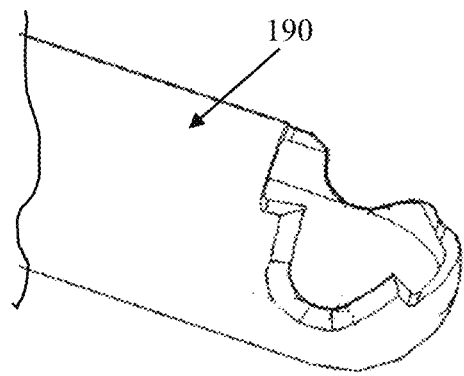
FIG. 6A is an enlarged perspective view of a portion of a second tubular member of the device of FIG. 2A.
Figure 6B:
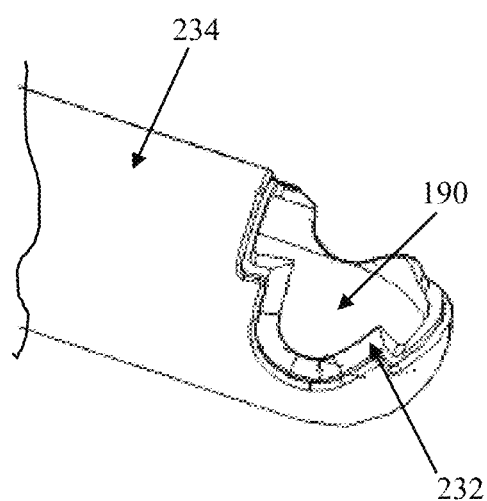
FIG. 6B is an enlarged perspective view of the second tubular member of FIG. 6A coated with an electrical insulator.

As illustrated in FIG. 5, the first electrode assembly 160 includes a first rotary electrical connection assembly 230 maintained by the second hub member 204, the second tubular member 190 (forming or serving as a first elongate electrode body) and a first electrode 232 positioned at the distal end region 114. In some embodiments, the first electrode 232 is defined as an exposed region or surface area of the second tubular member 190. For example, it will be recalled that the second tubular member 190 can be formed of stainless steel (or other electrically conductive metal or material). Portions of an exterior surface of the second tubular member 190 can be coated or covered with an electrical insulator material 234; as generally reflected by FIG. 5, a proximal region of the second tubular member 190 is not covered by the electrical insulator 234 and is thus electrically coupled with the first rotary electrical connection assembly 230. FIG. 6A illustrates a distal region of the second tubular member 190 prior to application of the electrical insulator 234. This same region is shown in the view of FIG. 6B following application of the electrical insulator 234. As best seen in FIG. 6B, a portion of an exterior surface of the second tubular member 190 is exposed or not otherwise covered by the electrical insulator, and thus serves as the first electrode or electrode surface 232.

Figure 7:
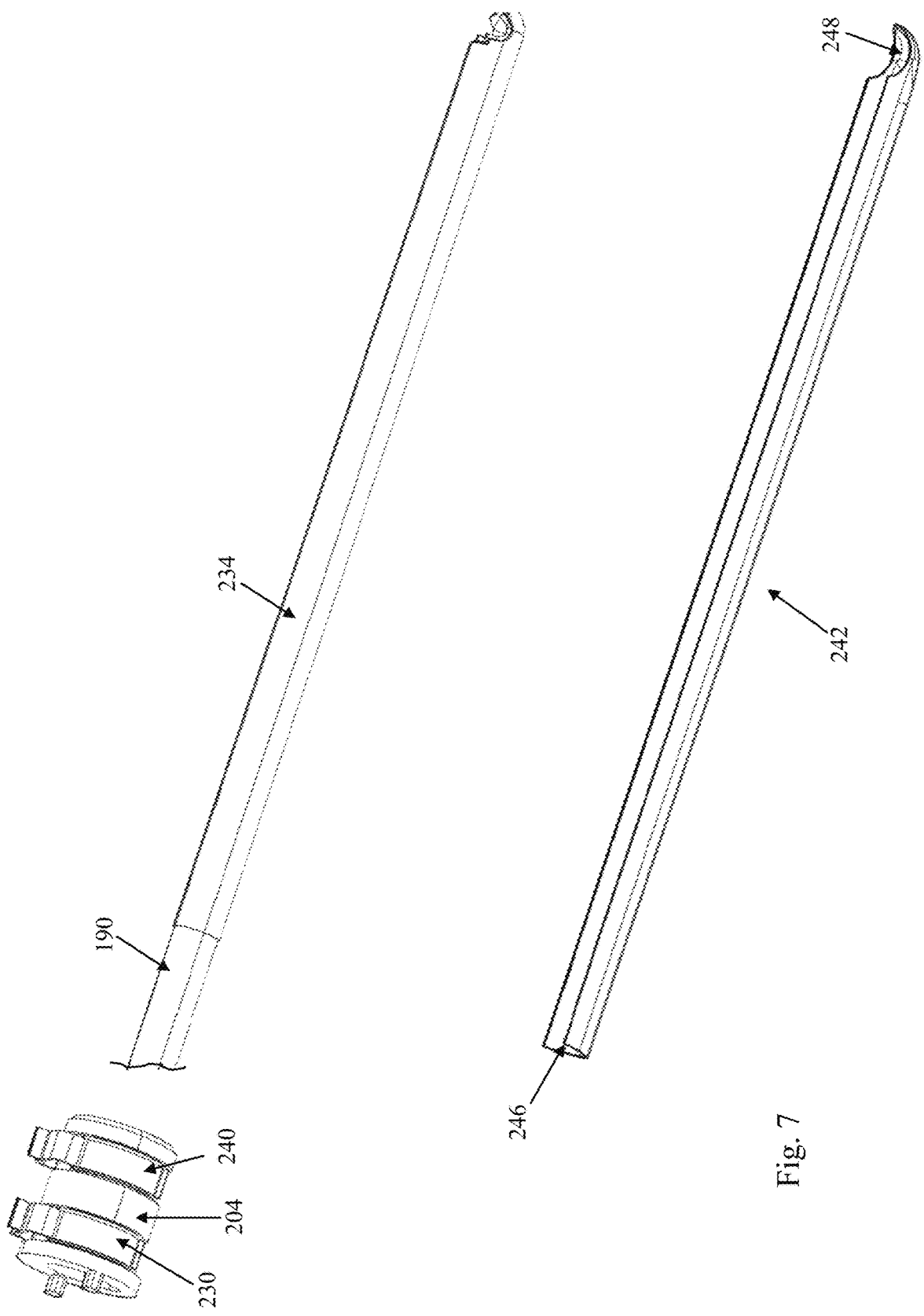
FIG. 7 is an exploded perspective view of the first and second electrode assemblies of FIG. 5.

Returning to FIG. 5, in a similar manner, the second electrode assembly 162 includes a second rotary electrical connection assembly 240 maintained by the second hub member 204, a second elongate electrode body (or cap) 242 and a second electrode 244 positioned at the distal end region 114. As a point of reference, FIG. 7 illustrates the second electrode body 242 apart from the second tubular member 190 (that is otherwise coated with the electrical insulator 234 as described above). The second electrode body 242 is formed of an electrically conductive metal, and forms a trough 246 generally sized and shaped to receive the coated second tubular member 190. A cup section 248 is formed by the trough 246 at a distal end of the second electrode body 242. Upon final assembly, the second electrode body 242 is electrically connected to the second rotary electrical connection assembly 240 (it being recalled that the second tubular member 190 serves as the first electrode body and is electrically connected to the first rotary electrical connection assembly 230), and is electrically isolated from the second tubular member/first electrode body 190 by the electrical insulator 234. Returning to FIG. 5, an insulating layer 250 is applied about and covers portions of an exterior surface of the second electrode body 242 (e.g., the insulating layer 250 can be a heat shrink type material that couples the second electrode body 242 to the coated second tubular member 190). A portion of an exterior surface of the second electrode body 242 is exposed or not otherwise covered by the insulating layer 250, and thus serves as the second electrode or electrode surface 244.

The first and second electrodes or electrode surfaces 232, 244 are electrically isolated from one another (e.g., by the electrical insulator 234) and can comprise bipolar electrodes. The electrodes 232, 244 may comprise or operate as wet or dry electrodes. The electrodes 232, 244 may be used to deliver any suitable energy for purposes of coagulation, hemostasis or sealing of tissue. As described above, the electrodes 232, 244 can be spaced apart to provide energy delivery to tissue. The electrical insulator 234 is applied to the second tubular member 190 to electrically isolate the second tubular member 190 from the second electrode body 242. In addition, the insulating layer 250 (e.g., formed from or through a heat shrinking process) can be applied around the second electrode body 242.

With reference to FIGS. 2A, 2B and 8, the electrodes 232, 244 are particularly useful with fluid such as saline provided by the fluid source 134 (FIG. 1) which may be emitted at or adjacent the distal end region 114. In order to provide fluid delivery to the distal end region 114, in some optional embodiments the device 110 includes an irrigation hub or collar 260. As best seen in FIG. 2A, the irrigation collar 260 includes a first fluid connector 262 and a second fluid connector 264.

The first fluid connector 262 is fluidly coupled with a first annular channel 266 formed in the first hub member 202 as most clearly seen in FIG. 8. The first annular channel 266 is fluidly coupled with the irrigation inlet 198 of the second tubular member 190, and is thus fluidly open to the lumen 192 and the cutting window 194 of the second tubular member 190. Fluid entering the irrigation inlet 198 is carried within the lumen 192 between the first tubular member 170 and the second tubular member 190 (it being recalled that in some embodiments, an outer diameter of the first tubular member 170 is slightly less than a diameter of the lumen 192 of the second tubular member 190, generating a gap or spacing between the first and second tubular members 170, 190 along which fluid entering the irrigation inlet 198 can flow). Fluid carried within the lumen 192 is dispensed at the cutting window 194.

Figure 9:
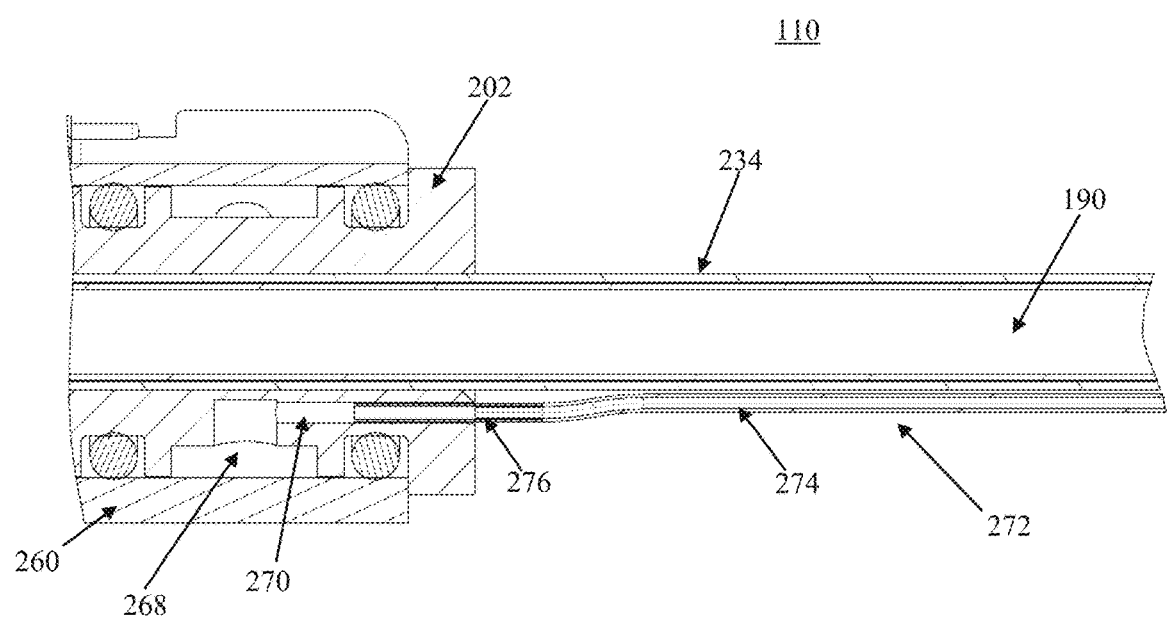
FIG. 9 is an enlarged, cross-sectional view of portions of the device of FIG. 2A.

The second fluid connector 264 is fluidly coupled with a second annular channel 268 formed in the first hub member 202. The second annular channel 268 includes or forms a passageway 270 that is fluidly coupled with an irrigation channel 272. The irrigation channel 272 extends from the first hub member 202 within the second hub member 204 and then distally in an orientation substantially parallel to the central axis A. The irrigation channel 272 can be generated in various fashions, as can the fluid coupling between the irrigation channel 272 and the second annular channel 268 in the first hub member 202. For example, FIG. 9 illustrates a portion of the device 110, including the second tubular member 190 (coated with the electrical insulator 234) mounted to the first hub member 202 (i.e., for ease of understanding, the second hub member 204 (FIG. 2B), the first tubular member 170 (FIG. 2B) and the second electrode body 242 (FIG. 8) are omitted from the view of FIG. 9). The irrigation channel 272 can, in some embodiments, include or be defined by an irrigation tube 274 that is fluidly coupled to the passageway 270 by a tubular fitting 276. The tubular fitting 276 can be press-fit into the passageway 270 or otherwise coupled thereto. The irrigation tube 274 is assembled to the fitting 276 and extends distally at an exterior of the second tubular member 190 (e.g., the irrigation tube 274 can be located between the second tubular member 190 and the second electrode body 242 as described below). The irrigation tube 274 may be formed of a variety of materials including a variety of metals and/or polymers. As examples, the tube 274 may be formed of stainless steel, polyimide, polyether block amide or polyamide. The irrigation channel 272 can be formed in a number of other manners that may or may not include the irrigation tube 274 as described below. Returning to FIG. 8, the irrigation channel 272 extends from the first hub member 202 to an outlet end 278 proximal the electrodes 232, 244. The irrigation channel 272 is positioned between the second tubular member 190 and the second electrode body 242, and extends to the outlet end 278 fluidly separate from the second tubular member 190 and the second electrode body 242. The irrigation channel 272 (e.g., the irrigation tube 274 (FIG. 9) is coupled to the second hub member 204 such that rotation of the second hub member 204 about the central axis A causes rotation of the irrigation channel 272 about the central axis A.

O-rings 206 provide fluid seals within the first hub member 202 such that fluid entering the first annular channel 266 from the first fluid connector 262 (FIG. 2A) is sealed on either side of the first annular channel 266. Likewise, fluid entering the second annular channel 268 from the second fluid connector 264 (FIG. 2A) is sealed on either side of the second annular channel 268.

Figure 10:
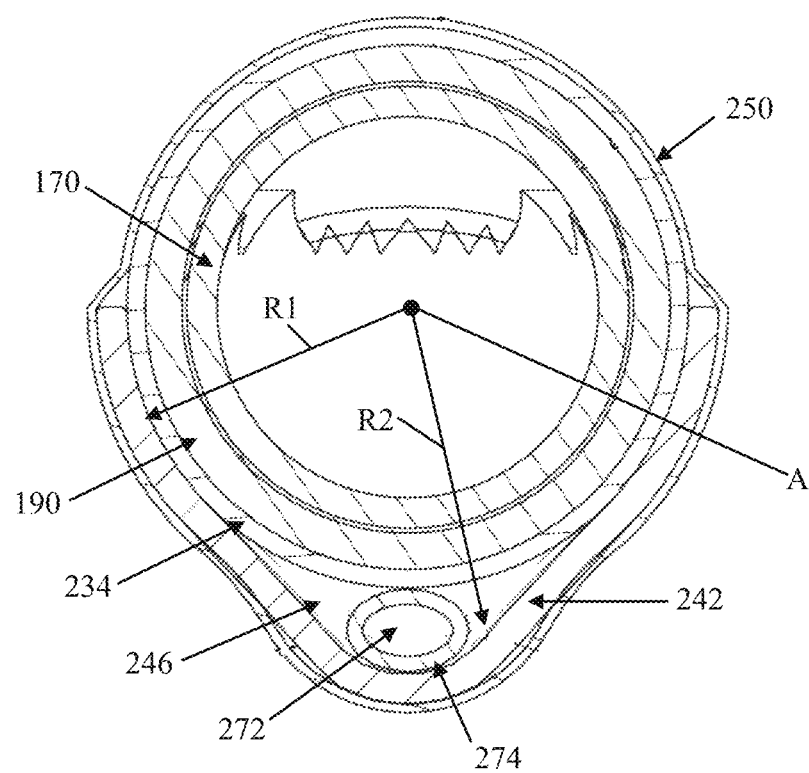
FIG. 10 is a cross section of the bipolar electrical device taken along line 10-10 of FIG. 2A.

FIG. 10 illustrates a cross section of device 110 along line 10-10 in FIG. 2A. As illustrated, the optional irrigation tube 274 is elliptical in cross section in defining the irrigation channel 272, but can be formed of other cross sectional shapes as well (e.g., a circle). The second electrode body 242 is U-shaped in cross section with respect to a plane that is perpendicular to the central axis A, adjoining with the electrical insulator 234 on either side of the irrigation tube 274. In particular, the second electrode body 242 has an arcuate shape defining the trough 246. The trough 246 is sized to co-axially receive the second tubular member 190 (coated with or covered by the electrical insulator 234) therein such that the second electrode body 242 partially surrounds an outer circumference of the second tubular member 190. To this end, a first radius R1 of the trough 246 is sized to accommodate the outer circumference of the second tubular member 190 having the electrical insulator 234 thereon. The trough 246 may define a second radius R2, greater than the first radius R1, to allow for the irrigation tube 274 to be positioned between the second tubular member 190 and the second electrode body 242. The first tubular member 170 is coaxially disposed within the second tubular member 190, with FIG. 10 reflecting that an outer diameter of the first tubular member 170 can be slightly less than an inner diameter of the second tubular member 190. Finally, the insulating layer 250 electrically insulates the second electrode body 242 and serves to retain the second electrode body 242 relative to the second tubular member 190 (as covered by the electrical insulator 234), such as by a heat shrink application.

Figure 11A:
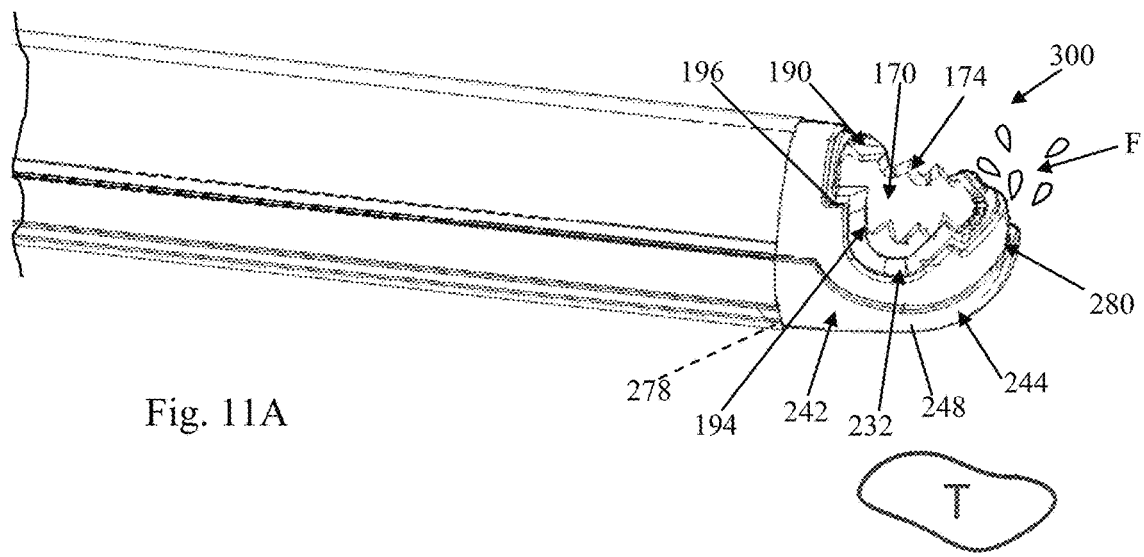
FIGS. 11A and 11B are isometric views of a distal end region of the bipolar electrical device of FIG. 2A in first and second special orientations, respectively.
Figure 11B:
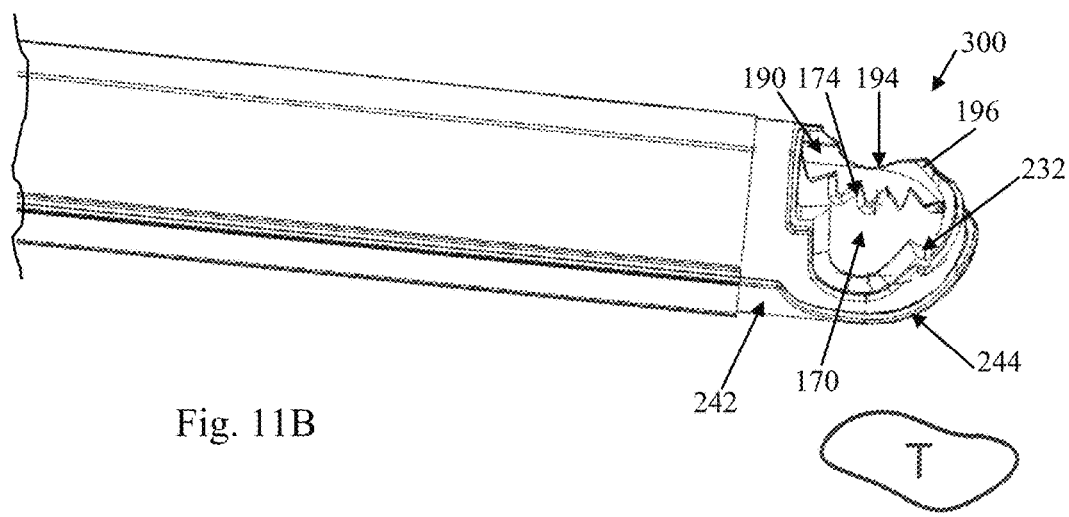

As illustrated in FIGS. 11A and 11B, the orientation of the second tubular member 190, when maintained in the trough 246 (FIG. 10), is such that the cutting window 194 of the second tubular member 190 faces in a direction opposite (or away from) the second electrode body 242. In this way, the serrated edge 196 of the cutting window 194 is fully exposed, as shown, upon final assembly of the second tubular member 190 within the trough 246.

In some embodiments, and likewise as shown, the distal cup 248 (referenced generally, best shown in FIG. 8) of the second electrode body 242 is fluidly coupled with the irrigation channel 272 (hidden in FIGS. 11A and 11B, but shown, for example, in FIG. 10) that is otherwise positioned between the second tubular member 190 and the second electrode body 242. The distal cup 248 is configured to direct fluid F from the outlet end 278 (identified generally in FIG. 11A, and shown in greater detail in FIG. 8) of the irrigation channel 272 out a fluid outlet 280 located between the distal cup 248 and the distal end of the second tubular member 190 such as depicted in FIG. 11A. In this configuration, the fluid outlet 280 is advantageously situated between and immediately adjacent bipolar electrode surfaces 232, 244 to provide coupling of the electrical energy and fluid F delivered to tissue T. Further, the outlet end 278 of the irrigation channel 272 is proximally spaced from the electrode surfaces 232, 244 and is radially outside of the second tubular member 190.

During operation, and with additional reference to FIGS. 1, 2A and 2B, the device 110 is coupled to the handpiece 130 by inserting the proximal end region 112 into an opening (not shown) in the handpiece 130. In particular, the hub 180 of the inner shaft assembly 150 is inserted into the opening and can include a proximal engagement member 290 (e.g., including tabs illustrated in FIG. 2A) for coupling with the motor (not shown) of the handpiece 130. Upon insertion of the device 110 into the handpiece 130, the actuator 138 is linked to or engages with the engagement member 206 of the first hub member 202. In one embodiment, the irrigation hub or collar 260 (or other component of the device 110) can include one or more alignment tabs 292 that orient the housing 120 with respect to the handpiece 130. In one particular embodiment, the tabs 282 are arranged such that coupling between the device 110 and the handpiece 130 orients the button 122 perpendicular to a rotational axis of the actuator 138. In the embodiment illustrated in FIG. 1, a right-handed user will have access to the button 122 and the actuator 138 through their right index finger. In similar manner, the device 110 can be rotated 180 degrees prior to insertion into the handpiece 130 such that button 122 faces an opposite direction to that illustrated in FIG. 1. In this orientation, a left-handed user will have access to the button 122 and the actuator 138 through their left index finger. Upon final connection with the handpiece 130, the device 110 may comprise two modes: a cutting or debridement mode and a sealing or hemostasis mode. These two modes may further be mutually exclusive. In an alternative embodiment, the two modes can be performed simultaneously.

As illustrated in FIGS. 11A and 11B, the cutting tip 174 provided by the first tubular member 170 is selectively exposed at the cutting window 194 relative to tissue site T. Upon final assembly, the cutting tip 174 is positioned at the cutting window 194 with the two components being rotatable relative to one another in oscillation or rotation (or both) in order to mechanically cut tissue (e.g., as driven by a motor contained within the handpiece 130 coupled with the power source 132 of FIG. 1). The cutting tip 174 and the cutting window 194 combine to define a cutting implement 300. Hemostasis is achieved via energy delivery to the tissue T through energy delivered to the electrodes 232, 244. In one embodiment, hemostasis is delivered while the cutting implement 300 is not active or cutting. In one embodiment, energy may be advantageously delivered simultaneously with a fluid such as saline to achieve an optimal tissue effect by delivering controlled thermal energy to tissue.

By way of explanation, FIG. 11A illustrates the first tubular member 170 rotated to a position whereby the cutting tip 174 is exposed via the cutting window 194 and away from the tissue site T. Upon partial rotation of the second tubular member 190 relative to the first tubular member 170 as illustrated in FIG. 11B, or vice-versa, less of the cutting tip 174 is exposed at the cutting window 194 and the orientation of the cutting window 194 approaches the tissue site T. In some positions, the second tubular member 190 and the second electrode body 242 are rotated such that the central lumen 172 (best seen in FIG. 3) of the first tubular member 170 is closed relative to the cutting window 194. Regardless, the second tubular member 190 and the second electrode body 242 are rotatable in tandem with respect to the first tubular member 170 in either direction a full 360 degrees through operation of the actuator 138 (FIG. 1). As such, operation of the actuator 138 can rotate the second tubular member 190 and the second electrode body 242 from FIG. 11B to the position of FIG. 11A in either direction as desired so as to face the tissue site T of interest.

Specific surgical techniques facilitated by the surgical cutting instruments described herein can be conducted in connection with features discussed above. During use, a hand (not shown) of a user (not shown) is employed to grasp the handpiece 130 (FIG. 1). In this regard, and in one embodiment, the handpiece 130 forms an exterior contour adapted to ergonomically fit within a user's hand, such as by grasping the handpiece 130. Regardless, the user then deploys the cutting implement 300, manipulating the handpiece 130 to deploy the cutting implement 300 to the target site T. Following initial deployment to the target site T, the cutting window 194 has a first spatial orientation relative to the target site T as indicated by the orientation of the cutting window 194 relative to target site T. More particularly, with the orientation of FIG. 11A, the cutting window 194 exposes the cutting tip 174. Further, the handpiece 130, can be generally described as defining an upright orientation as illustrated in FIG. 1 when naturally grasped by the user's hand, with the handpiece 130 positioned within the user's palm, such that the actuator 138 is proximate the user's thumb or index finger (not shown). In addition, the button 122 can be in close proximity to the actuator 138 such that the user can easily switch back and forth by controlling spatial orientation of the cutting window 194 and delivering RF energy through operation of the button 122.

An example surgical procedure may then require removal of tissue and/or hemostasis of the tissue T in a direction not directly facing or adjacent the cutting window 194. In the orientation of FIG. 11A, the cutting window 194 is away from the tissue site T, requiring movement of the cutting window 194 to allow either the cutting tip 174 or the electrodes 232, 244 to interact with the tissue T. To accomplish alteration of the spatial orientation of the cutting window 224, and with additional reference to FIGS. 1 and 2B, the user (not shown) rotates the actuator 138 in a desired direction. In particular, the user's thumb (not shown) and/or index finger (not shown) of the hand that is otherwise grasping the handpiece 130 is used to rotate the actuator 138. Rotation of the actuator 138 is translated to the first hub member 202. Rotation of the first hub member 202, in turn, causes the second tubular member 190, and thus the cutting window 224, to rotate relative to the tissue site T, the housing 120, the cutting tip 208 and the handpiece 130. Rotation of the actuator 138 continues until the cutting window 194 assumes the second spatial orientation shown in FIG. 11B. Notably, a rotational orientation of the handpiece 130 need not change when translating the cutting window 194 from the spatial orientation of FIG. 11A to the spatial orientation of FIG. 11B or any other orientation relative to the central axis A to face the tissue site T. That is to say, the cutting window 194 can be rotated to face any direction about the axis A.

Transition of the cutting window 194 from the spatial orientation of FIG. 11A to the spatial orientation of FIG. 11 (or other orientation as desired throughout a full 360 degree rotation about the central axis A) is accomplished, in one embodiment, with only a single hand of the user. The device 110 is configured such that the cutting window 194 can be spatially rotated relative to the handpiece 130 without requiring both hands of the user to otherwise grasp the handpiece 130 at two discrete locations and apply a twisting or torque-generating motion. In one embodiment, the single-handed cutting window rotation is accomplished by configuring the actuator 138 such that a movement axis of the actuator 138 is off-set from the central axis A, which is coaxial with a major axis of the first hub member 202. That is to say, the actuator 138 moves (e.g. rotates) about an axis or plane that is not co-axial with the central axis A of the first hub member 202; instead, movement of the actuator 138 is translated into rotation of the first hub member 202 about the central axis A. In one embodiment, the rotational axis of the actuator 138 is perpendicular to the central axis A. With this approach, then, the actuator 138 can be located at any desired position relative to the handpiece 130 so as to promote single-handed operation.

During delivery of electrical energy in hemostasis mode, in some embodiments fluid can be provided to the distal end region 114 through the cutting window 194, the fluid outlet 280, or both. Fluid delivered to the distal end region 114 interacts with the electrodes 232, 244. In this manner, the electrodes 232, 244 can advantageously provide Transcollation® sealing of tissue when used with the Transcollation® sealing energy supplied by the Aquamantys System, available from the Advanced Energy Division of Medtronic, Inc. With respect to "wet" RF coagulation technology, the technology for sealing tissue described in U.S. Pat. Nos. 6,558,385; 6,702,810, 6,953,461; 7,115,139, 7,311,708; 7,537,595; 7,645,277; 7,811,282; 7,998,140; 8,048,070; 8,083,736; and 8,361,068 (the entire contents of each of which is incorporated by reference) describe bipolar coagulation systems believed suitable for use with the device 110. Other systems for providing a source of energy are also contemplated.

Figure 12A:
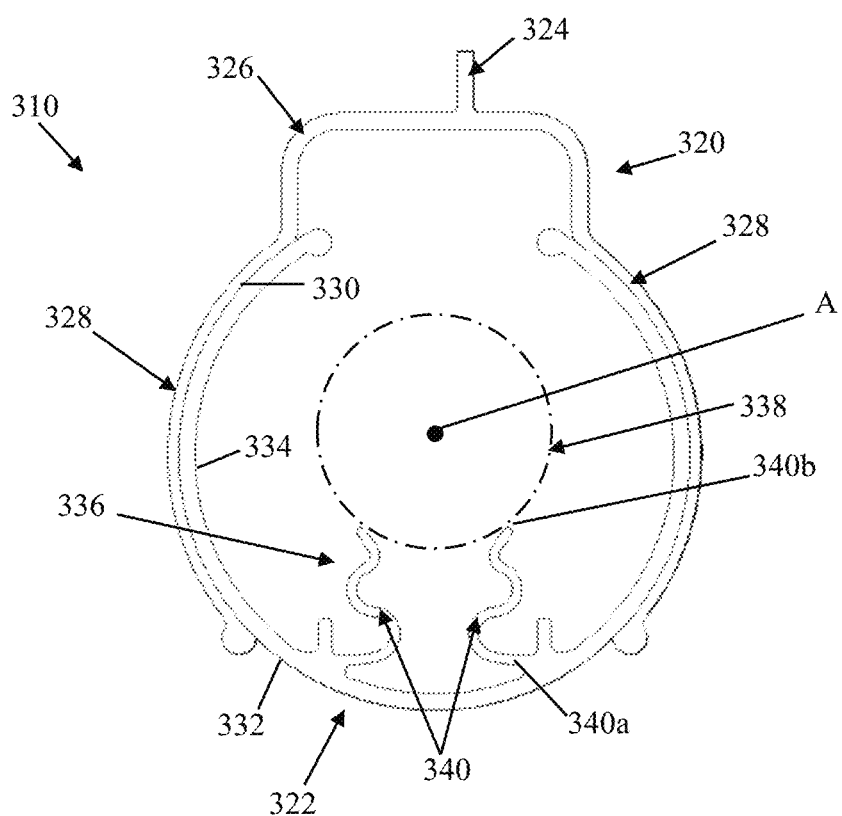
FIGS. 12A and 12B are plan views of first and second rotary electrical connection assemblies, respectively, useful with the device of FIG. 2A.
Figure 12B:
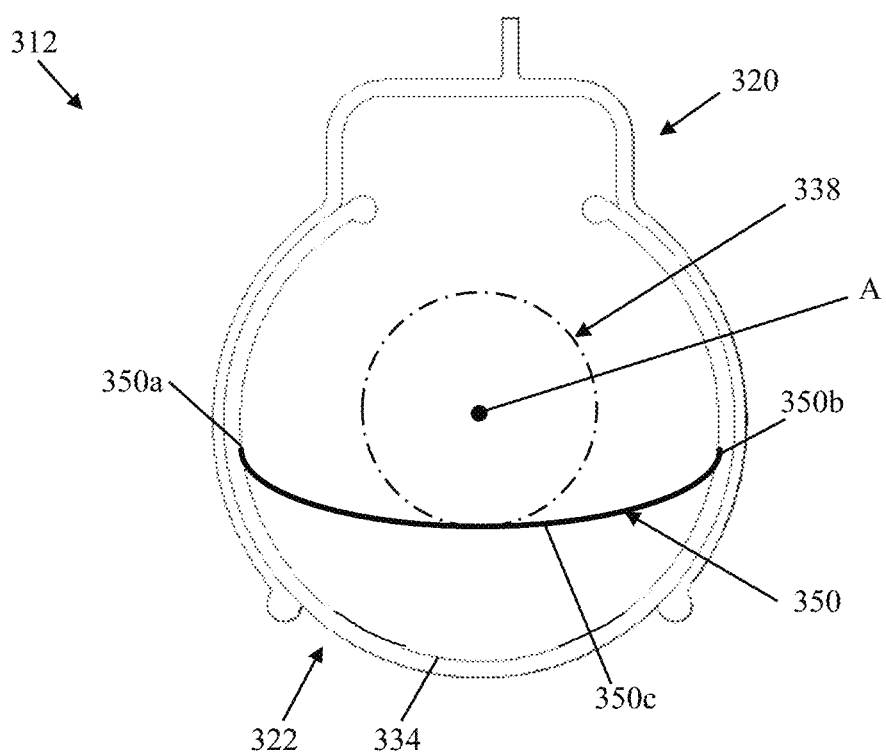

FIGS. 12A and 12B illustrate example rotary electrical connection assemblies 310 and 312, respectively, which allow the device 110 (FIG. 1) to provide 360 degree rotation of the cutting window 194 (FIG. 11A) with respect to the housing 130 (FIG. 1) while still providing electrical energy to the distal region 114 (FIG. 1). Either of the assemblies 310, 312 can be used as the rotary electrical connection assemblies 160, 162 discussed above with respect to FIG. 5. With reference to the first assembly 310 illustrated in FIG. 12A, the assembly 310 includes an outer, stationary connector 320 and an inner, rotating connector 322. The inner connector 322 is connected to the second hub member 204 (FIG. 4) to rotate therewith (e.g., a press-fit attachment), while the outer connector 320 is held stationary upon rotation of the second hub member 204 about the central axis A. The outer connector 320 and the inner connector 322 can be formed of material exhibiting suitable electrical conductive properties, such as brass. The outer stationary connector 320, in one embodiment, is a unitary body that includes an extension 324, a bridge 326 coupled with the extension 324 and opposed arcuate arms 328 extending from opposite sides of the bridge 326. The extension 324 is configured to connect to the PCB 224 (FIG. 2B). Electrical energy provided to the extension 324 is carried by the bridge 326 to each of the arms 328.

The arms 328 define an inner engagement surface 330 that is in contact with the inner connector 322, in particular an outer, first surface 332 of the inner connector 322. An inner, second surface 334 of the inner connector 322 is opposite first surface 332. An inner extension member 336 (referenced generally) extends inwardly toward axis A to connect with an arcuate connecting surface 338 (drawn in phantom) associated with or provide by a separate component of the device 110 (FIG. 1). In one example, the arcuate surface 338 is provided by the second tubular member 190 (FIG. 2B) or the second electrode body 242 (FIG. 2B). The extension member 336 exhibits resilient properties and defines a natural position and a deflected position in order to engage and capture the arcuate surface 338. In the illustrated embodiment, the extension member 336 includes a pair of opposed tabs 340 extending from the second surface 334. Each of the tabs 340 includes a first end 340a connected with the second surface 334 and a second end 340b opposite the first end 340a. Upon coupling of the extension member 336 with the arcuate surface 338, the second ends 340b of each of the tabs 340 deflect away from the rotational axis A. The resilient properties of the extension member 336 maintain contact with the arcuate surface 338 upon final assembly.

The assembly 312 illustrated in FIG. 12B is similar to the assembly 310, with similar elements similarly numbered. In contrast to the assembly 310 of FIG. 12A, the assembly 312 includes an extension member 350 that extends from a first end 350a connected to inner surface 334 to a second end 350b that is connected to inner surface 334 at a different position. An intermediate portion 350c of the extension member 350 transitions from a natural position to a deflected position when coupled with the arcuate surface 338. Due to resilient properties of the extension member 350, the intermediate portion 250c maintains electrical contact with the arcuate surface 338 upon final assembly.

Figure 13A:
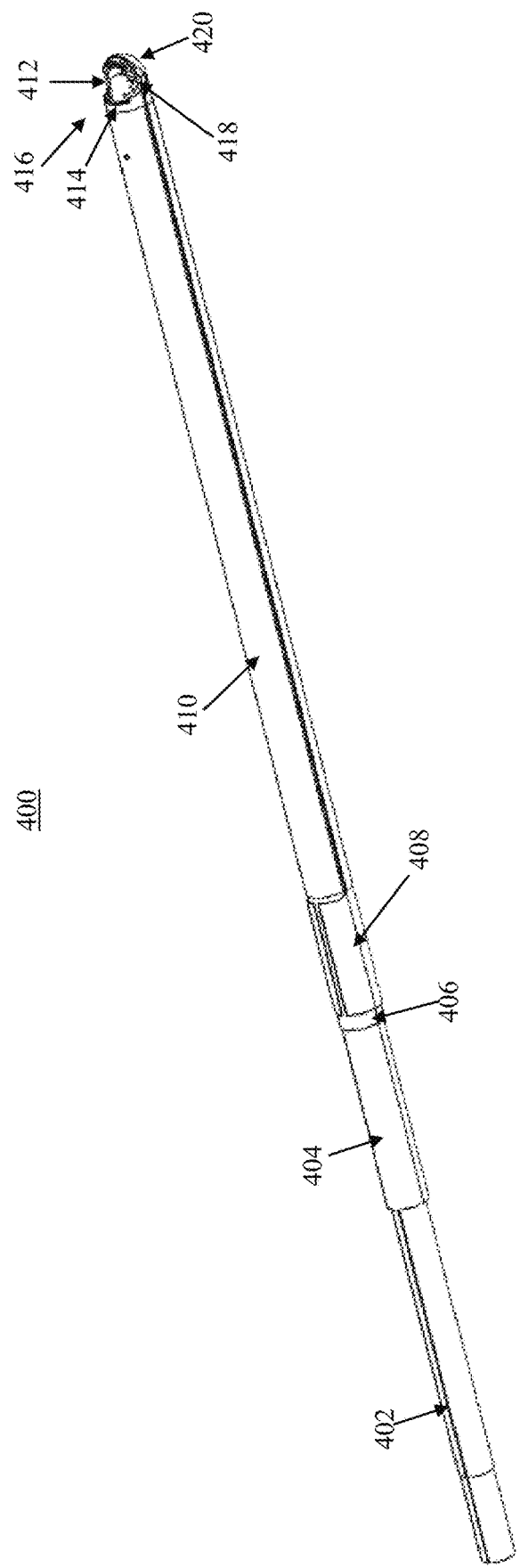
FIG. 13A is a perspective view of a portion of another bipolar electrical surgical device in accordance with principles of the present disclosure.
Figure 13B:
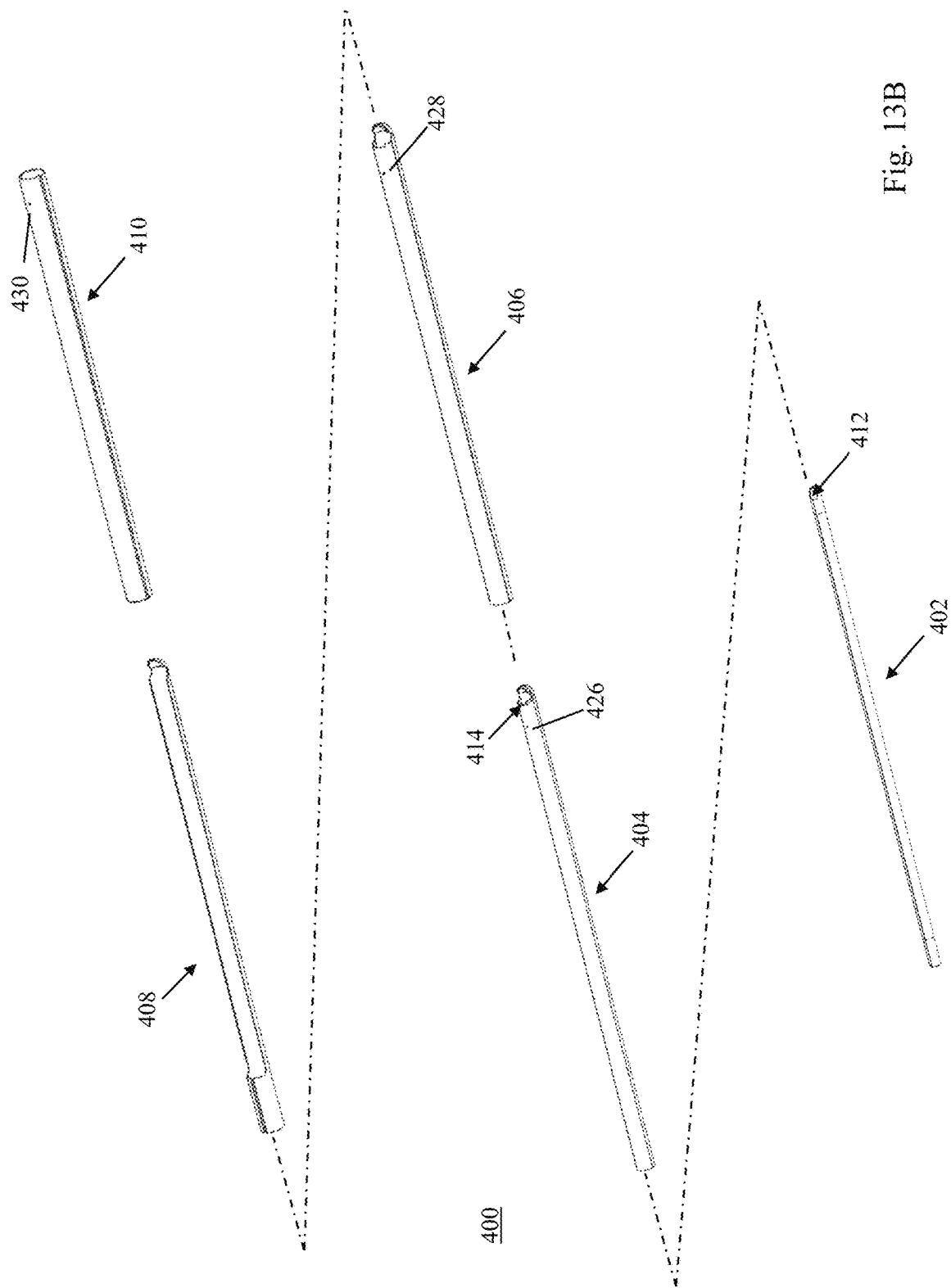
FIG. 13B is an exploded view of the device of FIG. 13A.

The bipolar electrical surgical devices of the present disclosure can incorporate other irrigation delivery constructions differing from the embodiments above. For example, FIGS. 13A and 13B illustrate portions of another electrical surgical device 400 in accordance with principles of the present disclosure. In particular, blade and electrode assembly components of the device 400 are shown and described below. For ease of explanation, various other components of the device 400 are omitted from the views; for example, the device 400 can include one or more of the various housings, hubs and electrical connections components described above with respect to the device 110 (FIG. 2A), or equivalent components or mechanisms. With this in mind, the device 400 includes an inner shaft or tubular member 402, an outer shaft or tubular member 404, an electrical insulator 406, a second electrode body or cap 408 and an insulating layer 410. In general terms, and akin to the embodiments above, the inner shaft 402 is rotatably disposed within the outer shaft 404 and forms a cutting tip 412. The cutting tip 412 is selectively exposed at a cutting window 414 of the outer shaft 404. The cutting tip 412 and the cutting window 414 combine to define a cutting implement 416. The electrical insulator 406 covers a majority of an exterior of the outer shaft 404. The outer shaft 404 is formed of an electrically conductive material and thus can serve as a first electrode body of the device 400. A distal portion of the outer shaft 404 is free of the electrical insulator 406, defining a first electrode surface 418. The second electrode body 408 receives the outer shaft 404 (coated with the electrical insulator 406). The insulating layer 410 covers a majority of an exterior of the second electrode body 408, optionally securing the second electrode body 408 to the outer shaft 404 (e.g., via heat shrink process). A distal region of the second electrode body 408 is free of the insulating layer 410, defining a second electrode surface 420.

The device 400 operates in a manner highly akin to the device 110 (FIG. 2A) as described above, with the inner shaft 402 powered to rotate or oscillate relative to the outer shaft 404 to perform tissue cutting, dissection, etc., at the cutting implement 416. Further, the electrode surfaces 418, 420 can be operated as bipolar electrodes as described above. In addition, the device 400 is configured to provide irrigation in a region of the electrode surfaces 418, 420 as described below.

Figure 14A:
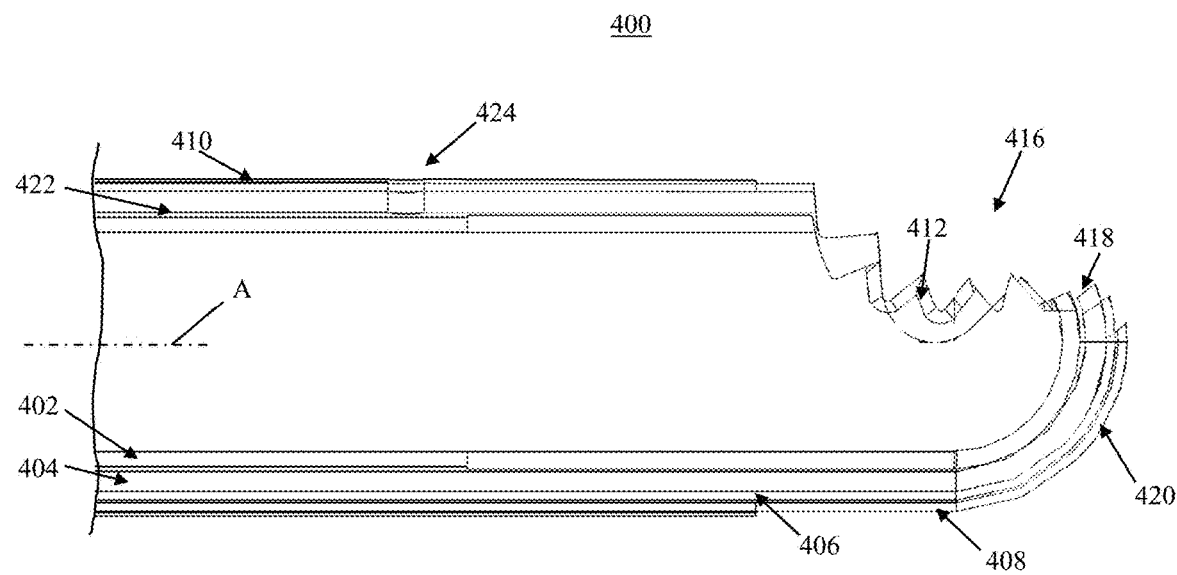
FIG. 14A is an enlarged, longitudinal cross-sectional view of a portion of the device of FIG. 13A.
Figure 14B:
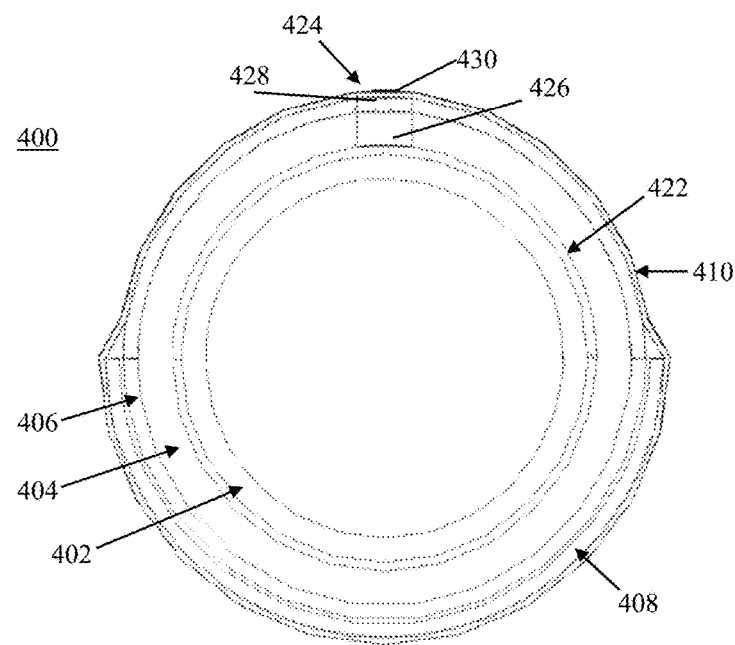
FIG. 14B is an enlarged, transverse cross-sectional view of the device of FIG. 13A.

In particular, and with additional reference to FIGS. 14A and 14B, an outer diameter of the inner shaft 402 is less than an inner diameter of the outer shaft 404 along a substantial portion of the length of the inner and outer shafts 402, 404. The difference in diameter generates an irrigation channel 422 between the inner and outer shafts 402, 404 as identified in FIGS. 14A and 14B. The irrigation channel 422 extends in a direction generally parallel with a central axis A of the inner shaft 402, and can be viewed as being ring shaped, circumscribing an exterior of the inner shaft 402. The irrigation channel 422 terminates at or is fluidly open to at least one fluid outlet or irrigation outlet port 424 (referenced generally in FIGS. 14A and 14B). The outlet port 424 is located or spaced proximal the cutting tip 412 and the first and second electrode surfaces 418, 420, and at least a portion of the irrigation outlet port 424 is radially outside of or beyond the outer shaft 404. In some embodiments, the irrigation outlet port 424 is located opposite the second electrode body 408.

Figure 15:
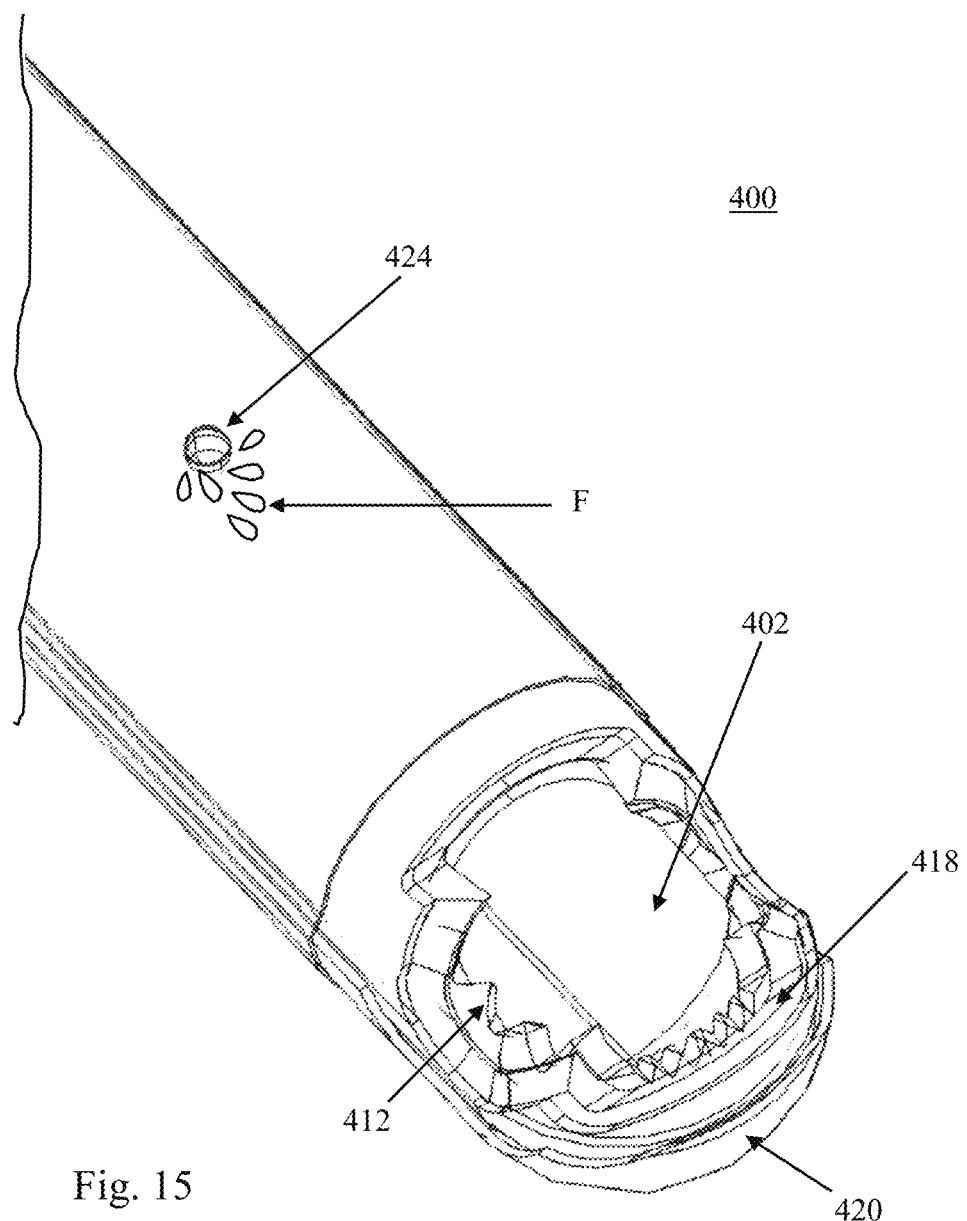
FIG. 15 is an enlarged, perspective view of the device of FIG. 13A, and illustrating delivery of fluid.

The at least one irrigation outlet port 424 can be considered or viewed as a weep hole, and can be formed in various manners. In some embodiments, the irrigation outlet port 424 is collectively defined by aligned holes formed in the outer shaft 404, the electrical insulator 406 and the insulating layer 410. For example, FIG. 13B generally identifies a hole 426 through a wall thickness of the outer shaft 404, a hole 428 through a wall thickness of the electrical insulator 406, and a hole 430 through a wall thickness of the insulating layer 410. Upon final assembly and as shown in FIG. 14B, the holes 426-430 are aligned, establishing a fluidly open connection between the irrigation channel 422 and an exterior of the device 400 (e.g., liquid from irrigation channel 422 can progress through the irrigation outlet port 424 to an exterior of the insulating layer 410) and thus toward the electrode surfaces 418, 420. FIG. 14A further reflects that in some embodiments, an outer diameter of the inner shaft 402 increases distal the irrigation outlet port 424 and approaches the inner diameter of the outer shaft 404; with these optional embodiments, while a fluid seal between the inner and outer shafts 402, 404 may or may not be established, the close dimensional relationship between the inner and outer shafts 402, 404 distal (or downstream of) the irrigation outlet port 424 dictates that at least a majority of the liquid within the irrigation channel 422 will exit or emit via the irrigation outlet port 424. As shown in FIG. 15, then, fluid (e.g., saline) F delivered through the irrigation channel 422 (FIG. 14B) is dispensed to an exterior of the device 400 via the irrigation outlet port 424 and can progress into contact with the electrode surfaces 418, 420 to promote operation thereof in a bipolar mode as described above. With embodiments in which the device 400 provides suction or aspiration at the cutting tip 412 (e.g., as described above, a lumen of the inner shaft 402 can be connected to a suction source), the saline or other fluid F expressed through the irrigation outlet port 424 will not be immediately or primarily aspirated from the treatment site.

The irrigation delivery construction of the device 400, and in particular the irrigation channel 422 and irrigation outlet port(s) 424, can be implemented into the device 400 in a relatively low cost manner. In some embodiments, it has surprisingly been found that by emitting saline (or other fluid) at a location proximally spaced from the cutting tip 412 (or other location of suction), electrical performance of the electrode surfaces 418, 420 (e.g., cautery performance) is greatly improved as compared to arrangements in which the saline (or other fluid) is emitted from between the inner and outer shaft 402, 404 at or immediately adjacent the cutting tip 412. While the device 400 has been shown as providing one of the irrigation outlet ports 424, in other embodiments, two or more of the irrigation outlet ports 424 can be formed, each fluidly connecting the irrigation channel to an exterior of the device 400. The plurality of irrigation outlet ports 424 can be identical or dissimilar in terms of size and shape, and may or may not be aligned relative to a circumference of the outer shaft 404. Further, while the irrigation outlet port 424 has been described as being collectively formed by various holes formed in the outer shaft 404, electrical insulator 406 and the insulating layer 410, other constructions are also acceptable. For example, the insulating layer 410 can be formed of a porous material such that the distinct hole 430 need not necessarily be formed through the insulating layer.

Figure 16:
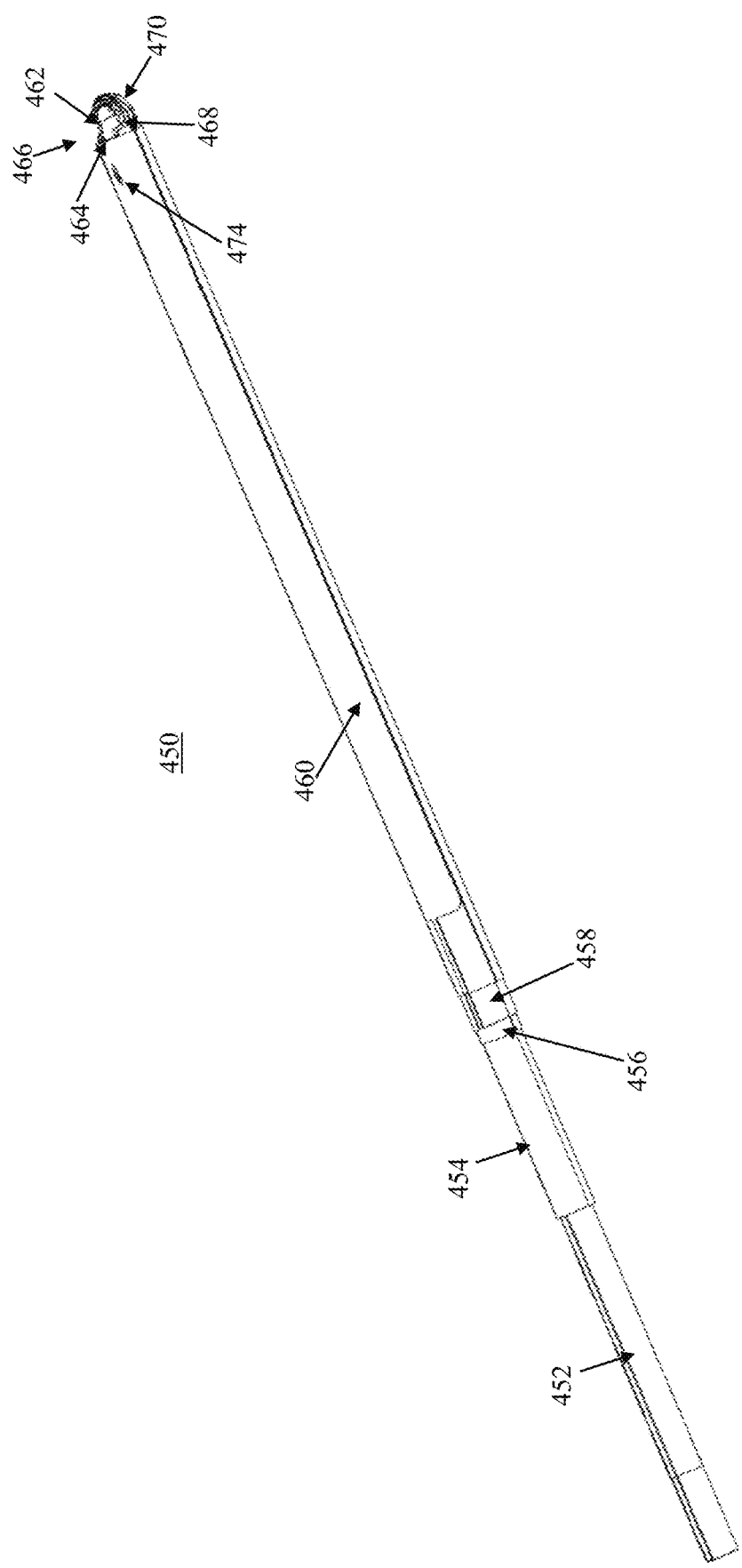
FIG. 16 is a perspective view of a portion of another bipolar electrical surgical device in accordance with principles of the present disclosure.

Portions of another electrical surgical device 450 in accordance with principles of the present disclosure are shown in FIG. 16. In particular, blade and electrode assembly components of the device 450 are shown and described below. For ease of explanation, various other components of the device 450 are omitted from the views; for example, the device 450 can include one or more of the various housings, hubs and electrical connections components described above with respect to the device 110 (FIG. 2A), or equivalent components or mechanisms. With this in mind, the device 450 can be highly akin to the device 400 (FIG. 13A) described above and includes an inner shaft or tubular member 452, an outer shaft or tubular member 454, an electrical insulator 456, a second electrode body or cap 458 and an insulating layer 460. In general terms, the inner shaft 452 is rotatably disposed within the outer shaft 454 and forms a cutting tip 462. The cutting tip 462 is selectively exposed at a cutting window 464 of the outer shaft 454. The cutting tip 462 and the cutting window 464 combine to define a cutting implement 466. The electrical insulator 456 covers a majority of an exterior of the outer shaft 454. The outer shaft 454 is formed of an electrically conductive material and thus can serve as a first electrode body of the device 450. A distal portion of the outer shaft 454 is free of the electrical insulator 456, defining a first electrode surface 468. The second electrode body 458 receives the outer shaft 454 (coated with the electrical insulator 456). The insulating layer 460 covers a majority of an exterior of the second electrode body 458, optionally securing the second electrode body 458 to the outer shaft 454 (e.g., via heat shrink process). A distal region of the second electrode body 458 is free of the insulating layer 460, defining a second electrode surface 470.

The device 450 operates in a manner highly akin to the device 110 (FIG. 2A) as described above, with the inner shaft 452 powered to rotate or oscillate relative to the outer shaft 454 to perform tissue cutting, dissection, etc., at the cutting implement 466. Further, the electrode surfaces 468, 470 can be operated as bipolar electrodes as described above. In addition, the device 450 is configured to provide irrigation in a region of the electrode surfaces 468, 470 as described below.

Figure 17:
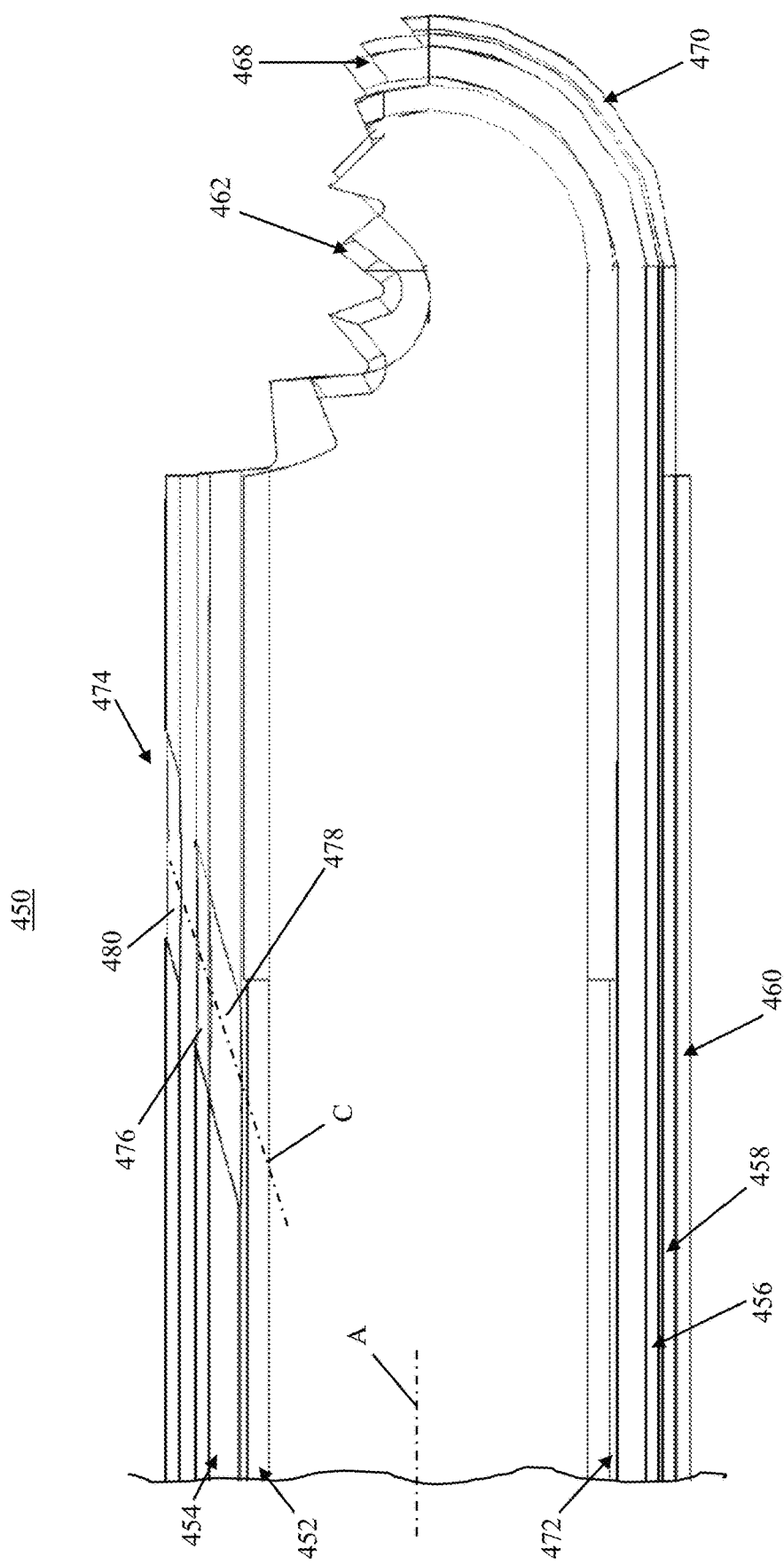
FIG. 17 is an enlarged, longitudinal cross-sectional view of a portion of the device of FIG. 16.

In particular, and with additional reference to FIG. 17, an outer diameter of the inner shaft 452 is less than an inner diameter of the outer shaft 454 along a substantial portion of the length of the inner and outer shafts 452, 454. The difference in diameter generates an irrigation channel 472 between the inner and outer shafts 452, 454. The irrigation channel 472 extends in a direction generally parallel with a central axis A of the inner shaft 452, and can be viewed as being ring shaped, circumscribing an exterior of the inner shaft 452. The irrigation channel 472 terminates at or is fluidly open to at least one fluid outlet or irrigation outlet port 474 (referenced generally in FIGS. 16 and 17). The irrigation outlet port 474 is located or spaced proximal the cutting tip 462 and the first and second electrode surfaces 468, 470, and at least a portion of the irrigation outlet port 474 is radially outside of or beyond the outer shaft 454. In some embodiments, the irrigation outlet port 474 is located opposite the second electrode body 468.

Figure 18:
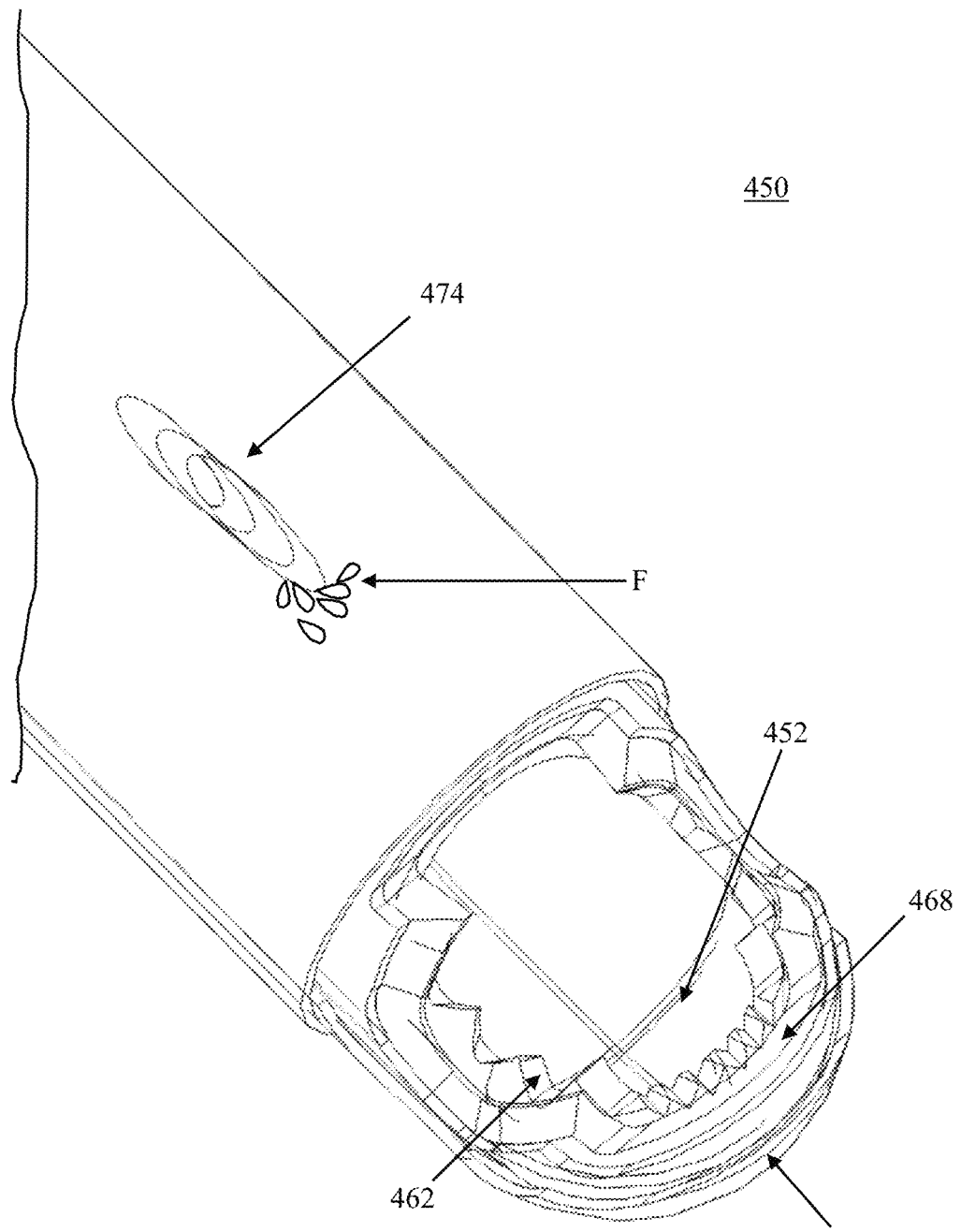
FIG. 18 is an enlarged, perspective view of a portion of the device of FIG. 16, and illustrating delivery of fluid.

The at least one irrigation outlet port 474 can be considered or viewed as a weep hole, and can be formed in various manners. In some embodiments, the irrigation outlet port 474 is collectively defined by aligned holes formed in the outer shaft 454, the electrical insulator 456 and the insulating layer 460. For example, FIG. 17 generally identifies a hole 476 through a wall thickness of the outer shaft 454, a hole 478 through a wall thickness of the electrical insulator 456, and a hole 480 through a wall thickness of the insulating layer 460. Upon final assembly, the holes 476-480 are aligned, establishing a fluidly open connection between the irrigation channel 472 and an exterior of the device 450 (e.g., liquid from irrigation channel 472 can progress through the irrigation outlet port 474 to an exterior of the insulating layer 460) and thus toward the electrode surfaces 468, 470. With the embodiment of FIGS. 16 and 17, the holes 476-480, and thus the irrigation outlet port 474 as a whole, are formed a non-perpendicular angle relative to the central axis A. With this construction, the irrigation outlet port 474 establishes a generally distal flow direction to fluid from the irrigation channel 472. Stated otherwise a centerline C of the irrigation outlet port 474 in non-perpendicular with respect to the central axis A, with a center of the hole 480 in the insulating layer 460 being distal a center of the hole 476 in the outer shaft 454. This directional component encourages fluid exiting the irrigation outlet port 474 to flow in a direction of the electrode surfaces 468, 470. FIG. 17 further reflects that in some embodiments, an outer diameter of the inner shaft 452 increases distal the irrigation outlet port 474 and approaches the inner diameter of the outer shaft 454; with these optional embodiments, while a fluid seal between the inner and outer shafts 452, 454 may or may not be established, the close dimensional relationship between the inner and outer shafts 452, 454 distal (or downstream of) the irrigation outlet port 474 dictates that at least a majority of the liquid within the irrigation channel 472 will exit or emit via the irrigation outlet port 474. As shown in FIG. 18, then, fluid (e.g., saline) F delivered through the irrigation channel 472 (FIG. 16) is dispensed to an exterior of the device 450 via the irrigation outlet port 474 and can progress into contact with the electrode surfaces 468, 470 to promote operation thereof in a bipolar mode as described above. With embodiments in which the device 450 provides suction or aspiration at the cutting tip 462 (e.g., as described above, a lumen of the inner shaft 452 can be connected to a suction source), the saline or other fluid F expressed through the irrigation outlet port 474 will not be immediately or primarily aspirated from the treatment site.

The irrigation delivery construction of the device 450, and in particular the irrigation channel 472 and irrigation outlet port(s) 474, can be implemented into the device 450 in a relatively low cost manner. In some embodiments, it has surprisingly been found that by emitting saline (or other fluid) at a location proximally spaced from the cutting tip 462 (or other location of suction), electrical performance of the electrode surfaces 468, 470 (e.g., cautery performance) is greatly improved as compared to arrangements in which the saline (or other fluid) is emitted from between the inner and outer shaft 452, 454 at or immediately adjacent the cutting tip 462. Directionality or control over the fluid F exiting the irrigation outlet port 474 is providing without requiring an additional channel or tube. While the device 450 has been shown as providing one of the irrigation outlet ports 474, in other embodiments, two or more of the irrigation outlet ports 474 can be formed, each fluidly connecting the irrigation channel to an exterior of the device 450. The irrigation outlet port(s) 474 can be configured to establish low pressure flow or a jet to overcome gravity in an upright orientation of the device 450.

Portions of another electrical surgical device 500 in accordance with principles of the present disclosure are shown in FIGS. 19A and 19B. In particular, blade and electrode assembly components of the device 500 are shown and described below. For ease of explanation, various other components of the device 500 are omitted from the views; for example, the device 500 can include one or more of the various housings, hubs and electrical connections components described above with respect to the device 110 (FIG. 2A), or equivalent components or mechanisms. With this in mind, the device 500 can be highly similar to the device 400 (FIG. 13A) described above and includes the inner shaft or tubular member 402, the outer shaft or tubular member 404, the electrical insulator 406, the second electrode body or cap 408 and the insulating layer 410. The cutting tip 412 and the cutting window 414 combine to define the cutting implement 416. The first and second electrode surfaces 418, 420 are formed as described above. In addition, the device 500 includes a dispensing conduit 502 as described below.

Figure 20A:
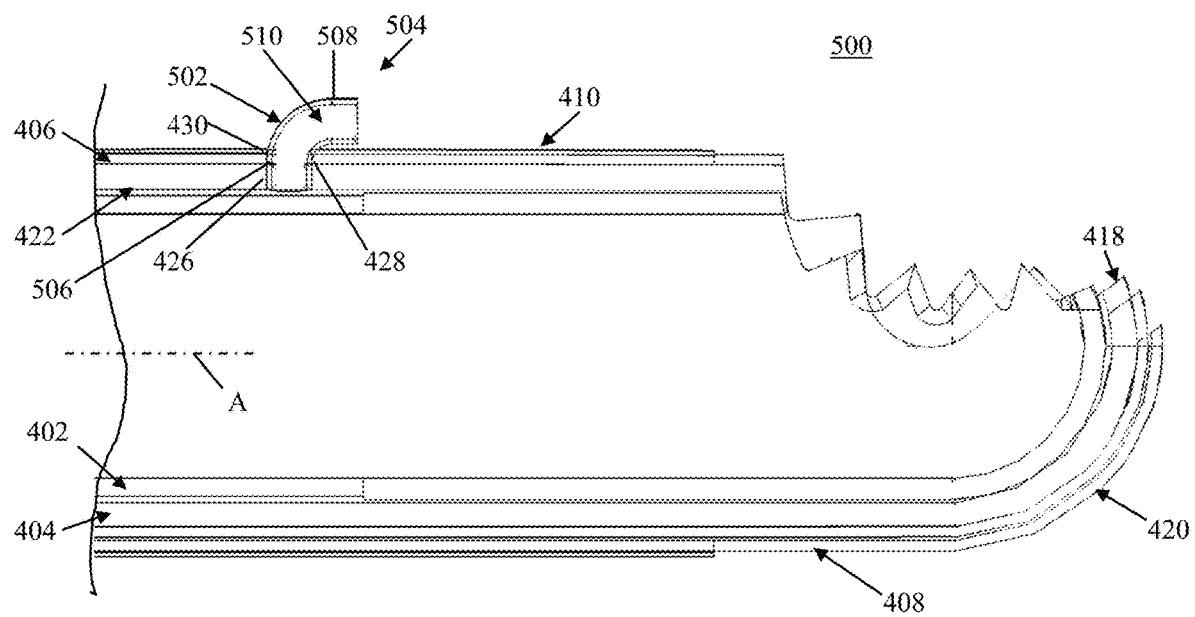
FIG. 20A is an enlarged, longitudinal cross-sectional view of a portion of the device of FIG. 19A.
Figure 20B:
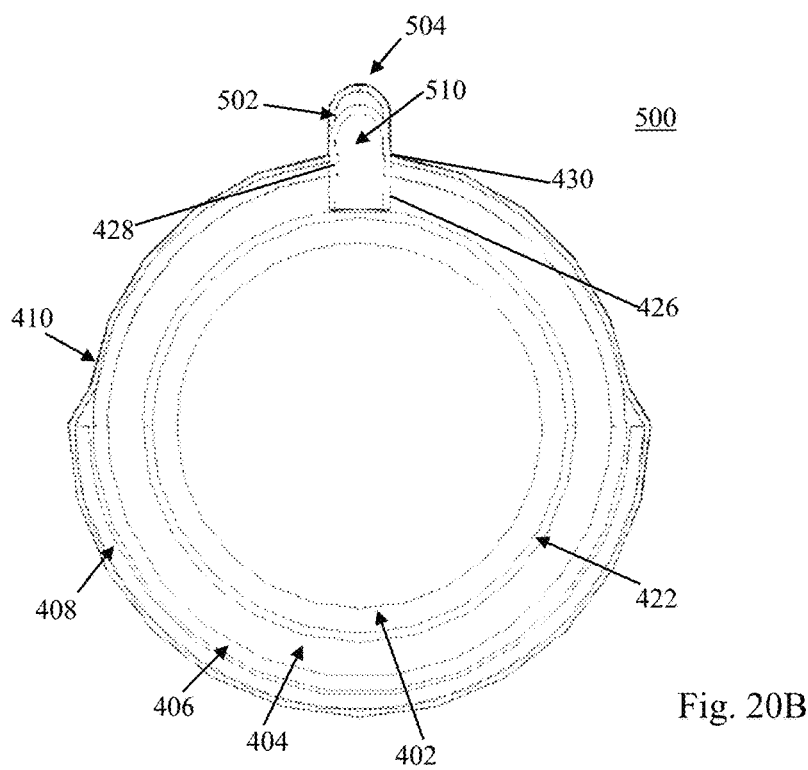
FIG. 20B is an enlarged, transverse cross-sectional view of the device of FIG. 19A.
Figure 21:
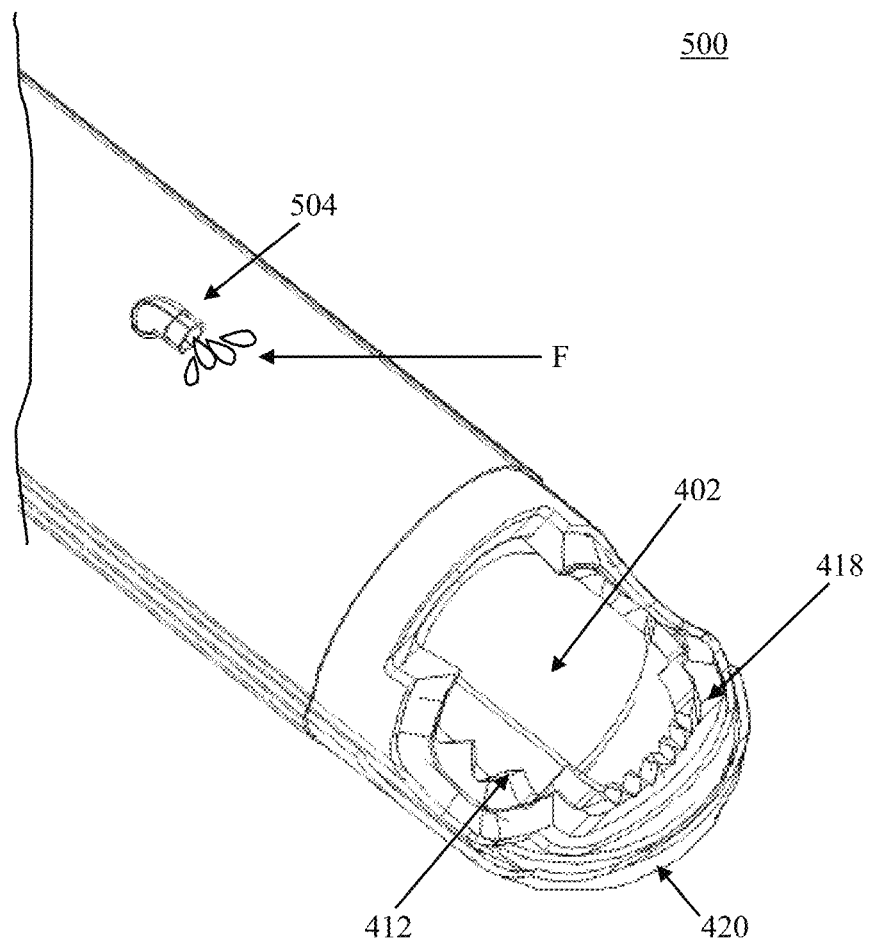
FIG. 21 is an enlarged, perspective view of a portion of the device of FIG. 19A, and illustrating delivery of fluid.

The conduit 502 is assembled to one or more of the outer shaft 404, the electrical insulator 406 and/or the insulating layer 410, and forms part of an irrigation outlet port 504 (identified generally in FIGS. 19A and 19B). In particular, and with additional reference to FIGS. 20A and 20B, the irrigation channel 422 is defined between the inner and outer shafts 402, 404 as described above. The conduit 502 includes or defines a base section 506 and a head section 508. A lumen 510 extends continuously through the conduit 502. The base section 506 is disposed within or fluid open to the holes 426-430 formed in the outer shaft 404, the electrical insulator 406, and the insulating layer 410, respectively. The head section 508 is maintained external the insulating layer 410, with a bend in the conduit 502 arranging the head section 508 to extend in a generally distal direction. Thus, the conduit 502 is configured to direct fluid flow from the irrigation channel 422 (via the lumen 510) in a distal direction, generally toward the electrode surfaces 418, 420. As shown in FIG. 21, the so-directed fluid (e.g., saline) flow F exits the irrigation outlet port 504 and is caused to flow in a direction of the electrode surfaces 418, 420 to promote operation thereof in a bipolar mode as described above. As with other embodiments, then, the irrigation outlet port 504 is proximally spaced from the electrode surfaces 418, 420 and the cutting tip 412, and is radially outside of the outer shaft 404 (FIG. 20A). With embodiments in which the device 500 provides suction or aspiration at the cutting tip 412, the saline or other fluid F expressed from the irrigation outlet port 504 will not be immediately or primarily aspirated from the treatment site.

The irrigation delivery construction of the device 500, and in particular the irrigation channel 422 (FIG. 20A) and irrigation outlet port(s) 504, can be implemented into the device 500 in a relatively low cost manner. In some embodiments, it has surprisingly been found that by emitting saline (or other fluid) at a location proximally spaced from the cutting tip 412 (or other location of suction), electrical performance of the electrode surfaces 418, 420 (e.g., cautery performance) is greatly improved as compared to arrangements in which the saline (or other fluid) is emitted from between the inner and outer shaft 402, 404 at or immediately adjacent the cutting tip 412. Distinct directionality or control over the fluid F exiting the irrigation outlet port 504 is provided. While the device 500 has been shown as providing one of the irrigation outlet ports 504, in other embodiments, two or more of the irrigation outlet ports 504 can be formed, each fluidly connecting the irrigation channel 422 to an exterior of the device 500. The irrigation outlet port(s) 504 can be configured to establish low pressure flow or a jet to overcome gravity in an upright orientation of the device 500.

Figure 22:
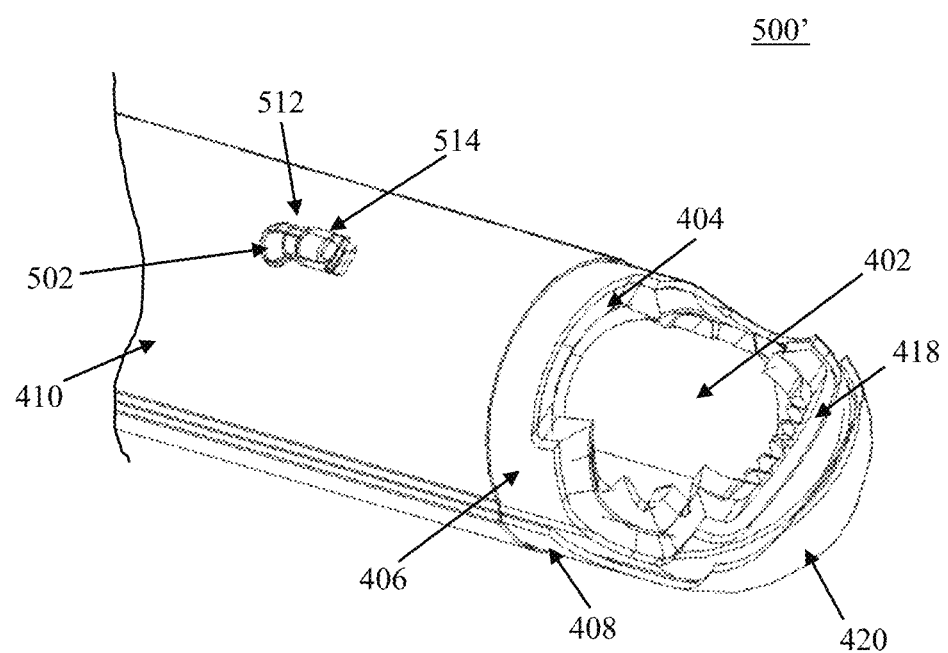
FIG. 22 is an enlarged, perspective view of a portion of another bipolar electrical surgical device in accordance with principles of the present disclosure.

Portions of another electrical surgical device 500' in accordance with principles of the present disclosure are shown in FIG. 22. The device 500' can be highly akin to the device 500 (FIG. 19A) described above, and includes the inner shaft or tubular member 402, the outer shaft or tubular member 404, the electrical insulator 406, the second electrode body or cap 408 and the insulating layer 410. The device 500' further includes the conduit 502 as previously described, fluidly connected to the irrigation channel 422 (hidden in FIG. 22, but shown, for example, in FIG. 20A). With the embodiment of FIG. 22, an irrigation outlet port 512 is provided, and includes the conduit 502 and a nozzle 514. The nozzle 514 is coupled to the conduit 502 and is fluidly open to the lumen 510 (hidden in FIG. 22, but shown, for example, in FIG. 20A). The nozzle 514 can assume various forms, and in some embodiments is configured to generate a mist-like pattern into fluid (not shown) emitted from the irrigation outlet port 512 in a direction of the electrode surfaces 418, 420.

Portions of another electrical surgical device 520 in accordance with principles of the present disclosure are shown in FIGS. 23A and 23B. In particular, blade and electrode assembly components of the device 520 are shown and described below. For ease of explanation, various other components of the device 520 are omitted from the views; for example, the device 520 can include one or more of the various housings, hubs and electrical connections components described above with respect to the device 110 (FIG. 2A), or equivalent components or mechanisms. With this in mind, the device 520 can be highly similar to the device 400 (FIG. 13A) described above and includes the inner shaft or tubular member 402, the outer shaft or tubular member 404, the electrical insulator 406, the second electrode body or cap 408 and the insulating layer 410. The cutting tip 412 and the cutting window 414 combine to define the cutting implement 416. The first and second electrode surfaces 418, 420 are formed as described above. In addition, the device 520 includes a deflector 522 as described below.

Figure 24A:
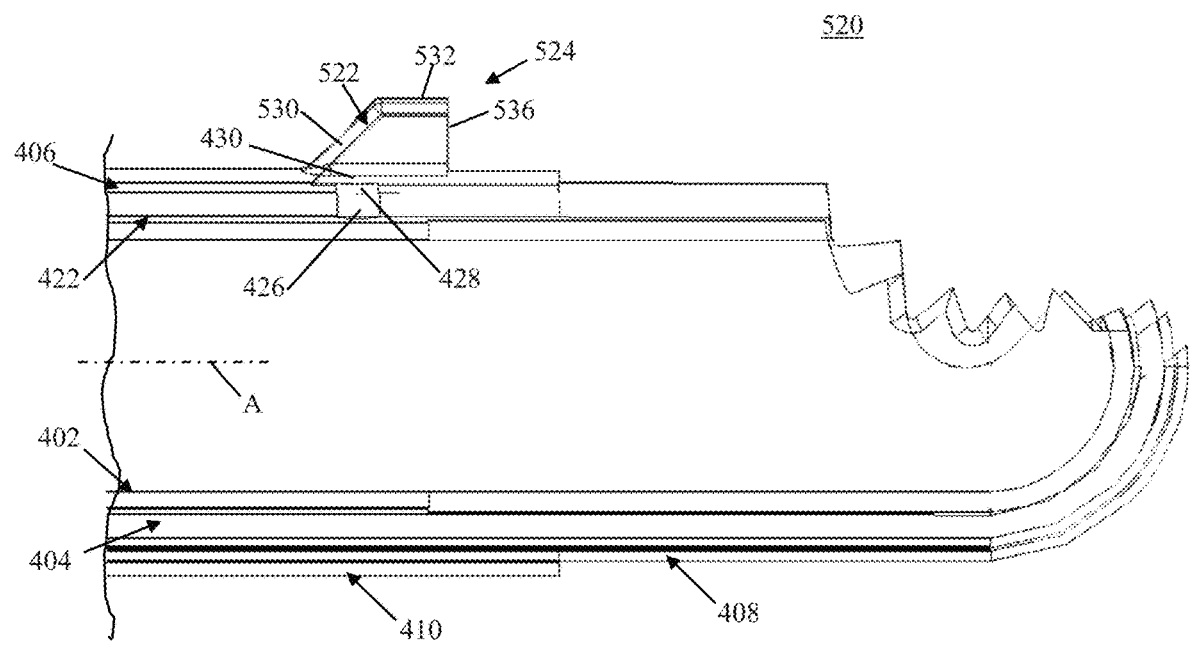
FIG. 24A is an enlarged, longitudinal cross-sectional view of a portion of the device of FIG. 23A.
Figure 24B:
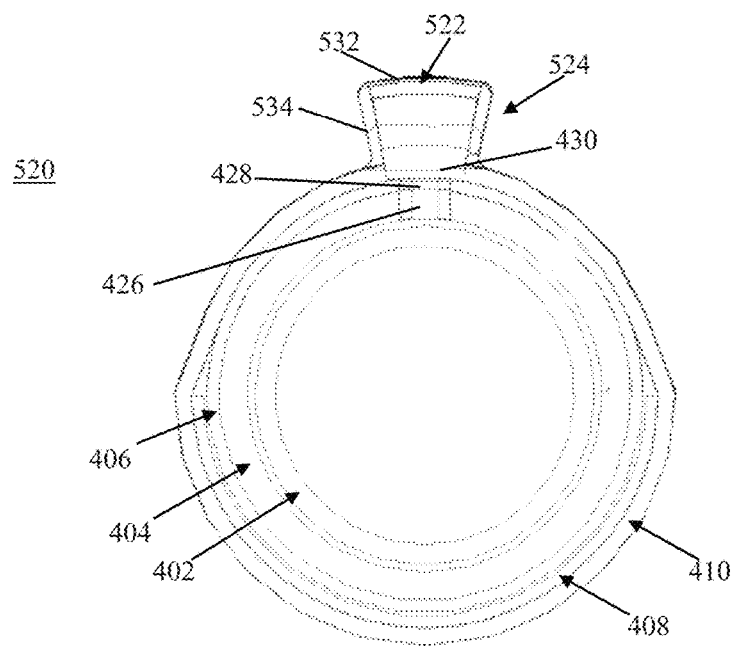
FIG. 24B is an enlarged, transverse cross-sectional view of the device of FIG. 23A.
Figure 25:
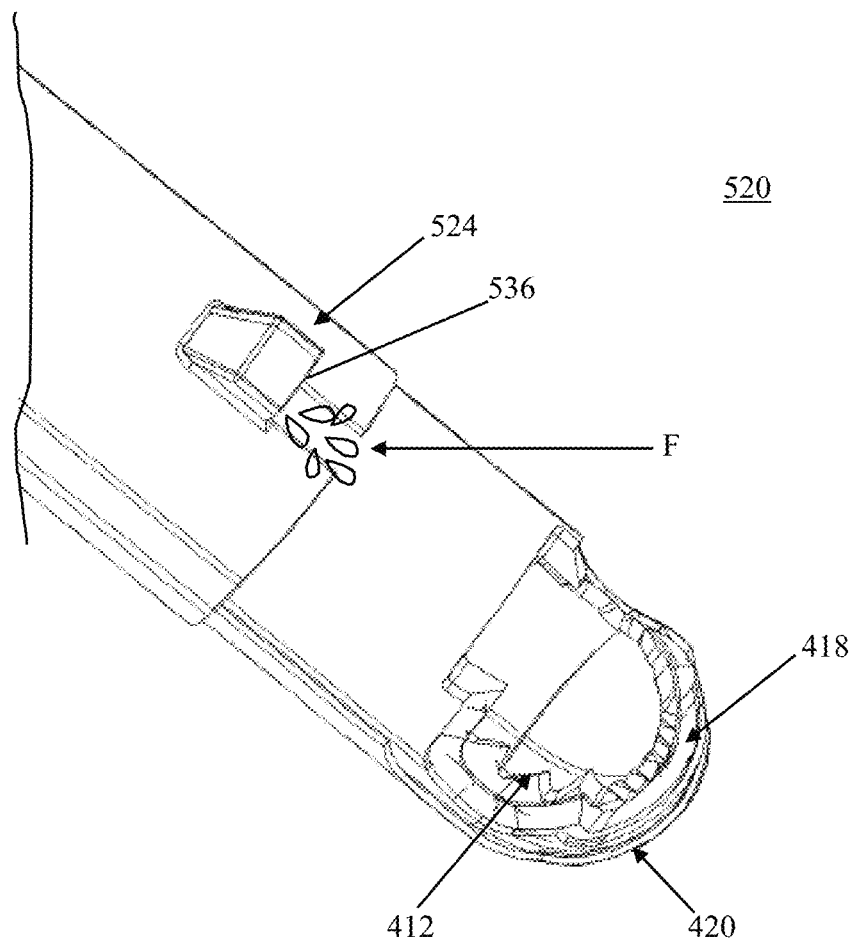
FIG. 25 is an enlarged, perspective view of a portion of the device of FIG. 23A, and illustrating delivery of fluid.

The deflector 522 is formed by or assembled to the insulating layer 410, and forms part of an irrigation outlet port 524 (identified generally in FIGS. 23A and 23B). In particular, and with reference to FIGS. 24A and 24B, the irrigation channel 422 is defined between the inner and outer shafts 402, 404 as described above. Further, the aligned holes 426-430 are formed in the outer shaft 404, the electrical insulator 406, and the insulating layer 410, respectively, as described above and form part of the irrigation outlet port 504. As best shown in FIG. 23B, the hole 430 in the insulating layer 430 can have an elongated or slot-like shape, optionally extending to a distal end of the insulating layer. The deflector 522 is located over the hole 430 in the insulating layer 410 and thus over the hole 428 in the electrical insulator 406, and is configured to deflect or direct fluid flow exiting the insulating layer hole 430 (or the electrical insulator hole 406) in a distal direction, generally toward the electrode surfaces 418, 420. For example, the deflector 522 can include or define a trailing wall 530 and an upper wall 532. The trailing wall 530 extends from the insulating layer 410 from a location proximal the insulating layer hole 430 (and the electrical isolator hole 428), projecting generally over the insulating layer hole 430. The upper wall 532 extends from the trailing wall 530 and is spaced from the insulating layer 410 and the electrical insulator 406. A major plane of the upper wall 532 can be substantially parallel with the central axis A, and one or more side walls 534 can also be included. Regardless, the deflector 522 defines an open side 536. Liquid flow exiting the electrical insulator hole 428 and/or the isolation layer hole 430 impinges upon the deflector walls 530-534 and is directed toward the open side 536. As shown in FIG. 25, the so-directed fluid (e.g., saline) flow F exits the irrigation outlet port 524 via the open side 536 and is caused to flow in a direction of the electrode surfaces 418, 420 to promote operation thereof in a bipolar mode as described above. As with other embodiments, then, the irrigation outlet port 524 is proximally spaced from the electrode surfaces 418, 420 and the cutting tip 412, and is radially outside of the outer shaft 404 (FIG. 24A). With embodiments in which the device 520 provides suction or aspiration at the cutting tip 412, the saline or other fluid F expressed from the irrigation outlet port 524 will not be immediately or primarily aspirated from the treatment site.

The irrigation delivery construction of the device 520, and in particular the irrigation channel 422 and irrigation outlet port(s) 524, can be implemented into the device 520 in a relatively low cost manner. In some embodiments, it has surprisingly been found that by emitting saline (or other fluid) at a location proximally spaced from the cutting tip 412 (or other location of suction), electrical performance of the electrode surfaces 418, 420 (e.g., cautery performance) is greatly improved as compared to arrangements in which the saline (or other fluid) is emitted from between the inner and outer shaft 402, 404 at or immediately adjacent the cutting tip 412. Distinct directionality or control over the fluid F exiting the irrigation outlet port 524 is provided. While the device 520 has been shown as providing one of the irrigation outlet ports 524, in other embodiments, two or more of the irrigation outlet ports 524 can be formed, each fluidly connecting the irrigation channel 422 to an exterior of the device 520. The irrigation outlet port(s) 524 can be configured to establish low pressure flow or a jet to overcome gravity in an upright orientation of the device 520.

Portions of another electrical surgical device 540 in accordance with principles of the present disclosure are shown in FIGS. 26A-26C. In particular, blade and electrode assembly components of the device 540 are shown and described below. For ease of explanation, various other components of the device 540 are omitted from the views; for example, the device 540 can include one or more of the various housings, hubs and electrical connections components described above with respect to the device 110 (FIG. 2A), or equivalent components or mechanisms. With this in mind, the device 540 includes an inner shaft or tubular member 542, an outer shaft or tubular member 544, an electrical insulator 546, a second electrode body or cap 548 and an insulating layer 550. In general terms, and akin to the embodiments above, the inner shaft 542 is rotatably disposed within the outer shaft 544 and forms a cutting tip 552. The cutting tip 552 is selectively exposed at a cutting window 554 of the outer shaft 544. The cutting tip 542 and the cutting window 544 combine to define a cutting implement 556. The electrical insulator 546 covers a majority of an exterior of the outer shaft 544. The outer shaft 544 is formed of an electrically conductive material and thus can serve as a first electrode body of the device 540. A distal portion of the outer shaft 544 is free of the electrical insulator 546, defining a first electrode surface 558. The second electrode body 548 receives the outer shaft 544 (coated with the electrical insulator 546). The insulating layer 550 covers a majority of an exterior of the second electrode body 548, optionally securing the second electrode body 548 to the outer shaft 544 (e.g., via heat shrink process). A distal region of the second electrode body 548 is free of the insulating layer 550, defining a second electrode surface 560.

The device 540 operates in a manner highly akin to the device 110 (FIG. 2A) as described above, with the inner shaft 542 powered to rotate or oscillate relative to the outer shaft 544 to perform tissue cutting, dissection, etc., at the cutting implement 556. Further, the electrode surfaces 558, 560 can be operated as bipolar electrodes as described above. In addition, the device 540 is configured to provide irrigation in a region of the electrode surfaces 558, 560 as described below.

Figure 27A:
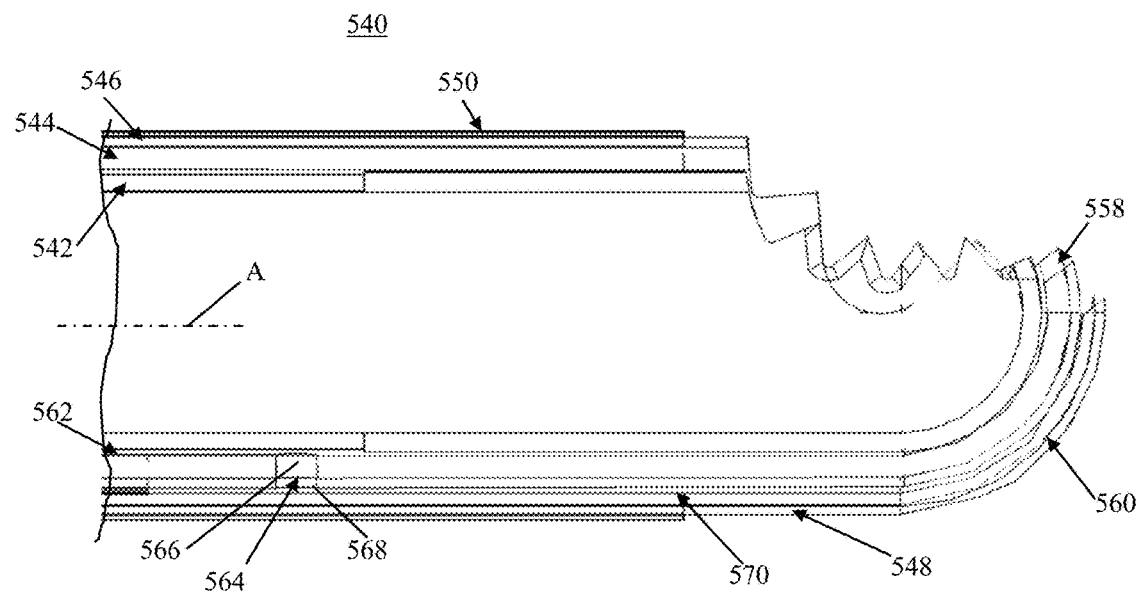
FIG. 27A is an enlarged, longitudinal cross-sectional view of a portion of the device of FIG. 26A.
Figure 27B:
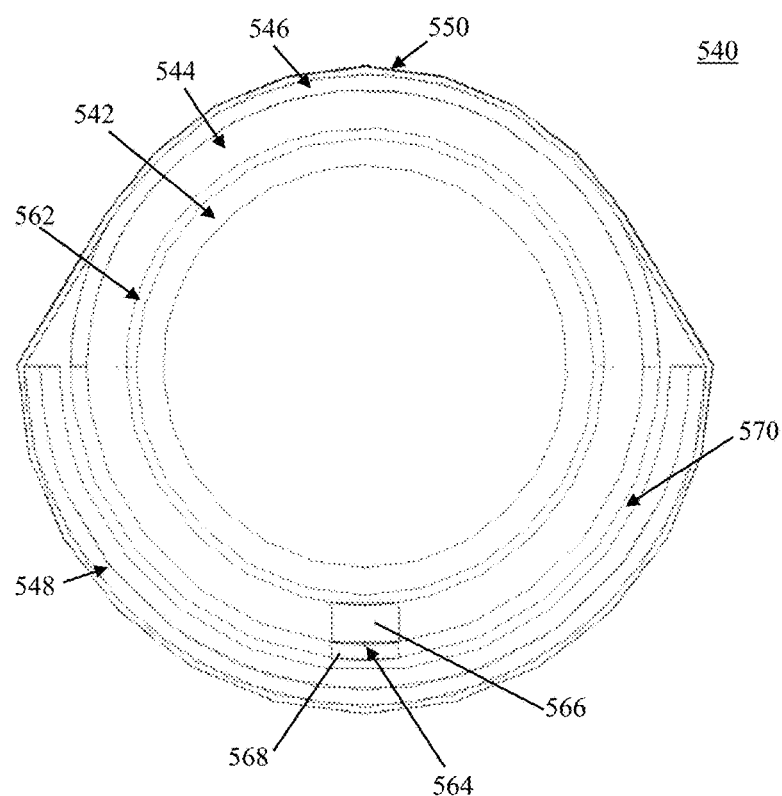
FIG. 27B is an enlarged, transverse cross-sectional view of the device of FIG. 26A.

In particular, and with additional reference to FIGS. 27A and 27B, an outer diameter of the inner shaft 542 is less than an inner diameter of the outer shaft 544 along a substantial portion of the length of the inner and outer shafts 542, 544. The difference in diameter generates an irrigation channel 562 between the inner and outer shafts 542, 544. The irrigation channel 562 extends in a direction generally parallel with a central axis A of the inner shaft 542, and can be viewed as being ring shaped, circumscribing an exterior of the inner shaft 542. The irrigation channel 562 terminates at or is fluidly open to at least one fluid outlet or irrigation outlet port 564 (referenced generally in FIGS. 27A and 27B). The irrigation outlet port 564 is located or spaced proximal the cutting tip 552 and the first and second electrode surfaces 558, 560, and at least a portion of the irrigation outlet port 564 is radially outside of or beyond the outer shaft 544. In some embodiments, the irrigation outlet port 564 is located proximate or "faces" the second electrode body 548 (referenced generally in FIGS. 27A and 27B).

The at least one irrigation outlet port 564 can be considered or viewed as a weep hole, and can be formed in various manners. In some embodiments, the irrigation outlet port 564 is collectively defined by aligned holes formed in the outer shaft 544 and the electrical insulator 546. For example, FIG. 26C generally identifies a hole 566 through a wall thickness of the outer shaft 544, and a hole 568 through a wall thickness of the electrical insulator 546. Upon final assembly and as shown in FIGS. 27A and 27B, the holes 566, 568 are aligned, establishing a fluidly open connection from the irrigation channel 562.

Figure 28:
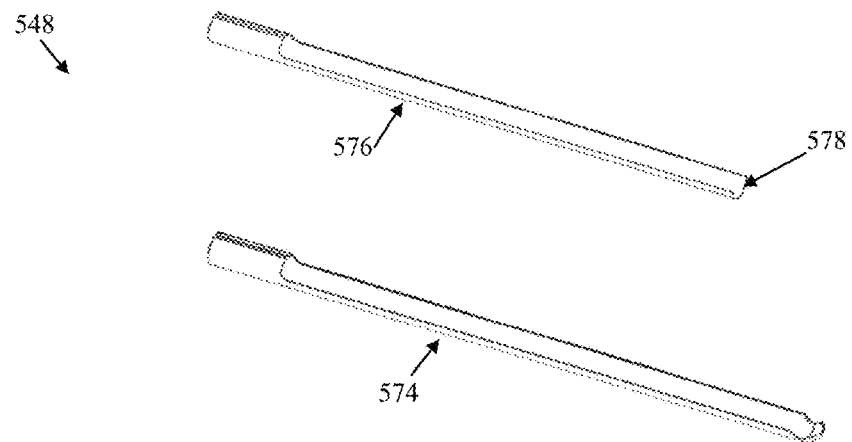
FIG. 28 is an exploded, perspective view of an electrode body component of the device of FIG. 26A.
Figure 29:
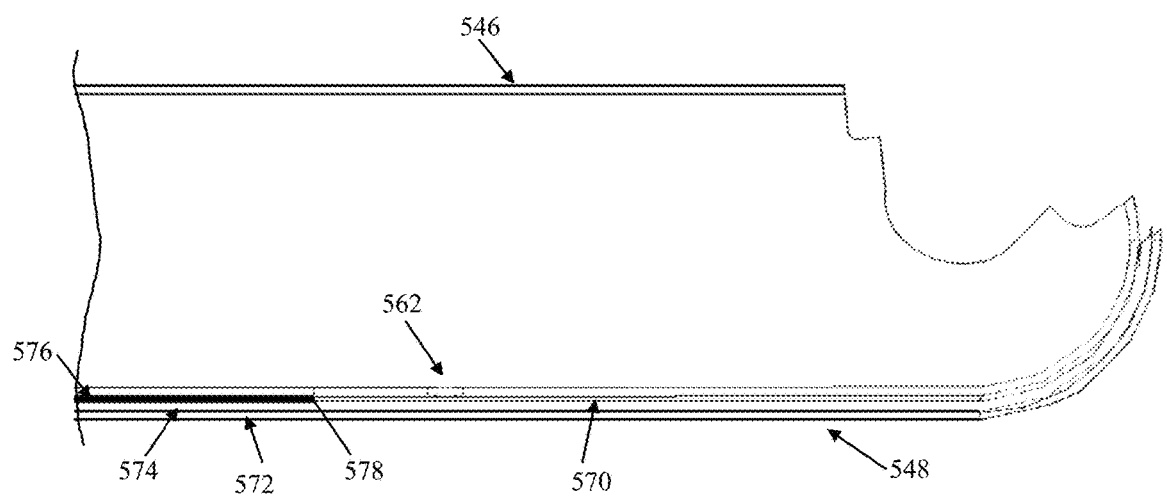
FIG. 29 is an enlarged, longitudinal cross-sectional view of the electrode body of FIG. 28 assembled to an electrical isolator component of the device of FIG. 26A.

Fluid flow from the irrigation outlet port 564 toward the electrode surfaces 558, 560 can be promoted by a gap 570 between the electrical insulator 546 and the second electrode body 548. In some embodiments, the second electrode body 548 can have a multi-layer construction that forms the gap 570 and provides desired electrical isolation from liquid exiting the irrigation outlet port 564. For example, liquid along the irrigation channel 562 will be in contact with the outer shaft 542; when the outer shaft 542 is energized (to energize the first electrode surface 558) and the second electrode body 548 is energized (to energize the second electrode surface 560), electrical isolation at the second electrode body 548 is desirable to prevent the liquid from causing an electrical short between the outer shaft 542 and the second electrode body 548. With this in mind, and with reference to FIG. 28, the second electrode body 548 can include an outer layer 572, and intermediate layer 574 and an inner layer 576. The outer layer 572 is formed of an electrically conductive material (e.g., metal), and serves to provide the second electrode surface 560. The intermediate and inner layers 574, 576 are formed of electrically non-conductive or insulative materials. A size and shape of the intermediate layer 576 corresponds with the size and shape of the outer layer 572. While a shape of the inner layer 576 generally corresponds that of the intermediate layer 574, a longitudinal length of the inner layer 576 is less than a length of the intermediate layer 574. More particularly, the inner layer 576 terminates at a distal end 578. As shown in FIG. 29 (otherwise illustrate the electrical insulator 546 and the second electrode body 548 in isolation), the distal end 578 of the inner layer 576 is located upstream of the irrigation outlet port 562. With this construction, a width of the gap 570 corresponds with a thickness of the inner layer 576. In other words, the inner layer 576 serves as a spacer to create the gap of fluid channel 570 and as a stop to prevent fluid from flowing backward. The intermediate layer 574 provides electrical isolation for the outer layer 572. The second electrode body 548 can be constructed in various manners, such as by coating an entire inner surface of the outer layer 572 with a non-conductive material to form the intermediate layer 574; the distal region of this so-formed part is then masked and a second coat of the non-conductive material is applied to generate the inner layer 576. Other constructions are also acceptable, and can include providing the intermediate and inner layers 574, 576 as a single or homogenous structure.

Figure 30:
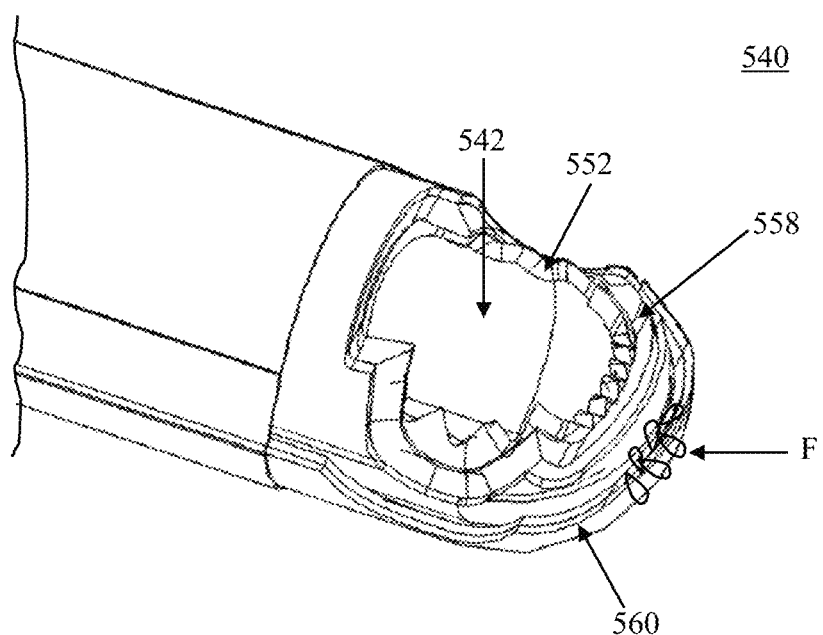
FIG. 30 is an enlarged, perspective view of a portion of the device of FIG. 26A, and illustrating delivery of fluid.

As shown in FIG. 30, fluid (e.g., saline) F delivered through the irrigation channel 562 (FIG. 27B) is dispensed to an exterior of the device 540 via the irrigation outlet port 564 (FIG. 27B) and the gap 570 (FIG. 27B) and can progress into contact with the electrode surfaces 558, 560 to promote operation thereof in a bipolar mode as described above. With embodiments in which the device 550 provides suction or aspiration at the cutting tip 552 (e.g., as described above, a lumen of the inner shaft 542 can be connected to a suction source), the saline or other fluid F expressed from the irrigation outlet port 564 will not be immediately or primarily aspirated from the treatment site.

The irrigation delivery construction of the device 540, and in particular the irrigation channel 562 (FIG. 27B) and irrigation outlet port(s) 564 (FIG. 27B), can be implemented into the device 540 in a relatively low cost manner, utilizing the second electrode body 548 to direct fluid flow to an optimum location. While the device 540 has been shown as providing one of the irrigation outlet ports 564, in other embodiments, two or more of the irrigation outlet ports 564 can be formed, each fluidly connecting the irrigation channel 562 to an exterior of the device 540. The plurality of irrigation outlet ports 564 can be identical or dissimilar in terms of size and shape, and may or may not be aligned relative to a circumference of the outer shaft 544.

Figure 31A:
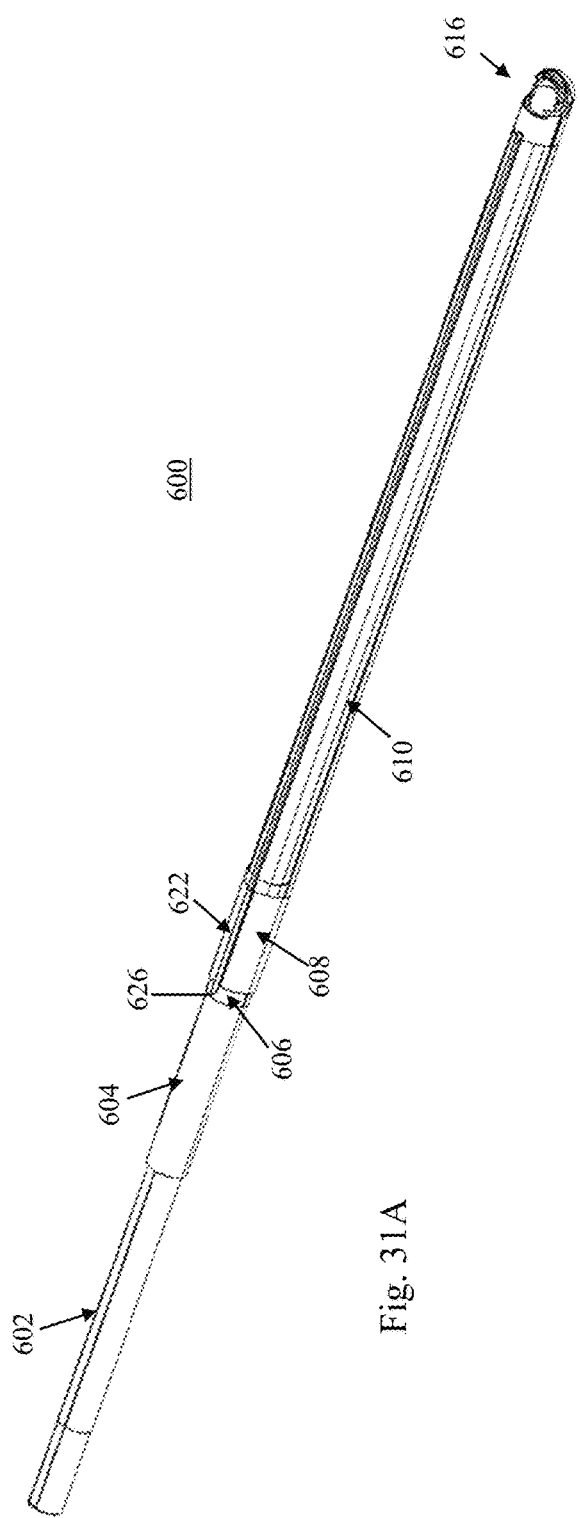
FIG. 31A is a perspective view of a portion of another bipolar electrical surgical device in accordance with principles of the present disclosure.
Figure 31B:
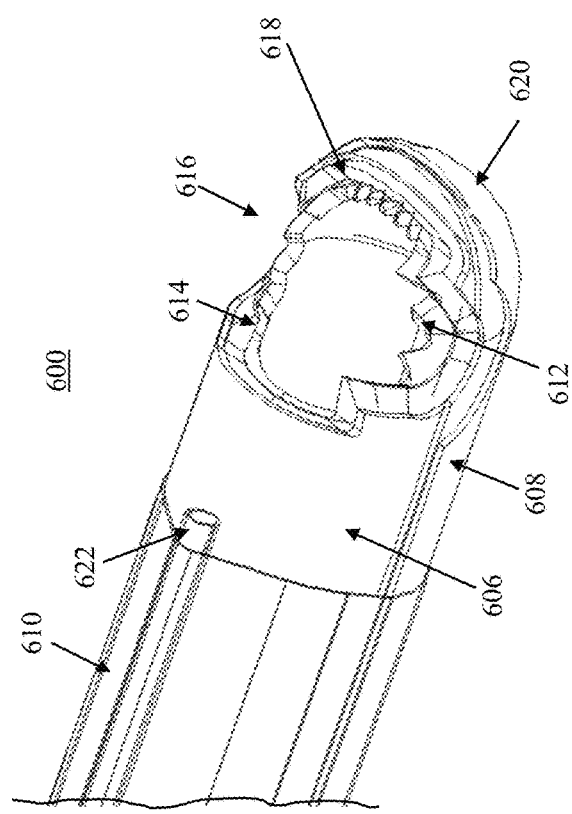
FIG. 31B is an enlarged, perspective view of a portion of the device of FIG. 31A.

Portions of another electrical surgical device 600 in accordance with principles of the present disclosure are shown in FIGS. 31A and 31B. In particular, blade and electrode assembly components of the device 600 are shown and described below. For ease of explanation, various other components of the device 600 are omitted from the views; for example, the device 600 can include one or more of the various housings, hubs and electrical connections components described above with respect to the device 110 (FIG. 2A), or equivalent components or mechanisms. With this in mind, the device 600 can be highly similar to the devices described above and includes an inner shaft or tubular member 602, an outer shaft or tubular member 604, an electrical insulator 606, a second electrode body or cap 608 and an insulating layer 610. The inner shaft 602 is rotatably disposed within the outer shaft 604 and forms a cutting tip 612. The cutting tip 612 is selectively exposed at a cutting window 614 of the outer shaft 604. The cutting tip 612 and the cutting window 614 combine to define a cutting implement 616. The electrical insulator 606 covers a majority of an exterior of the outer shaft 604. The outer shaft 604 is formed of an electrically conductive material and thus can serve as a first electrode body of the device 600. A distal portion of the outer shaft 604 is free of the electrical insulator 606, defining a first electrode surface 618. The second electrode body 608 receives the outer shaft 604

(coated with the electrical insulator 606). The insulating layer 610 covers a majority of an exterior of the second electrode body 608, optionally securing the second electrode body 608 to the outer shaft 604 (e.g., via heat shrink process). A distal region of the second electrode body 608 is free of the insulating layer 610, defining a second electrode surface 620. In addition, the device 600 includes an irrigation tube 622 as described below.

The device 600 operates in a manner highly akin to the device 110 (FIG. 2A) as described above, with the inner shaft 602 powered to rotate or oscillate relative to the outer shaft 604 to perform tissue cutting, dissection, etc., at the cutting implement 616. Further, the electrode surfaces 618, 620 can be operated as bipolar electrodes as described above. In addition, the device 600 is configured to provide irrigation in a region of the electrode surfaces 618, 620 as described below.

Figure 32A:
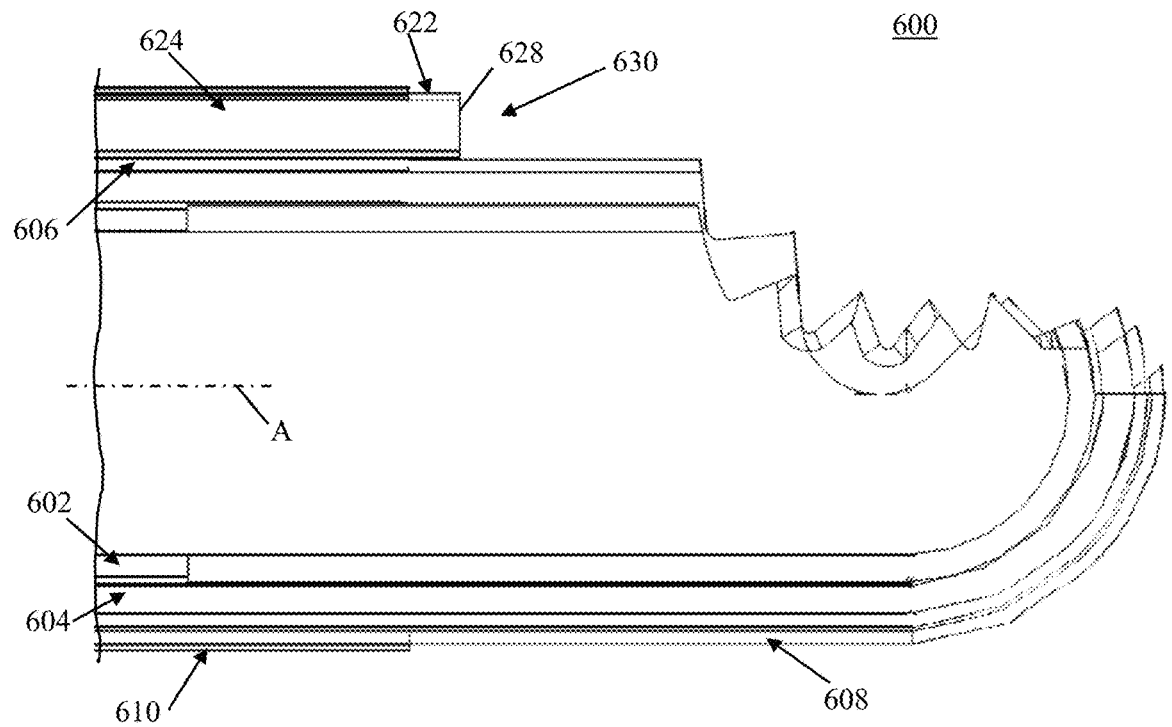
FIG. 32A is an enlarged, longitudinal cross-sectional view of a portion of the device of FIG. 31A.
Figure 32B:
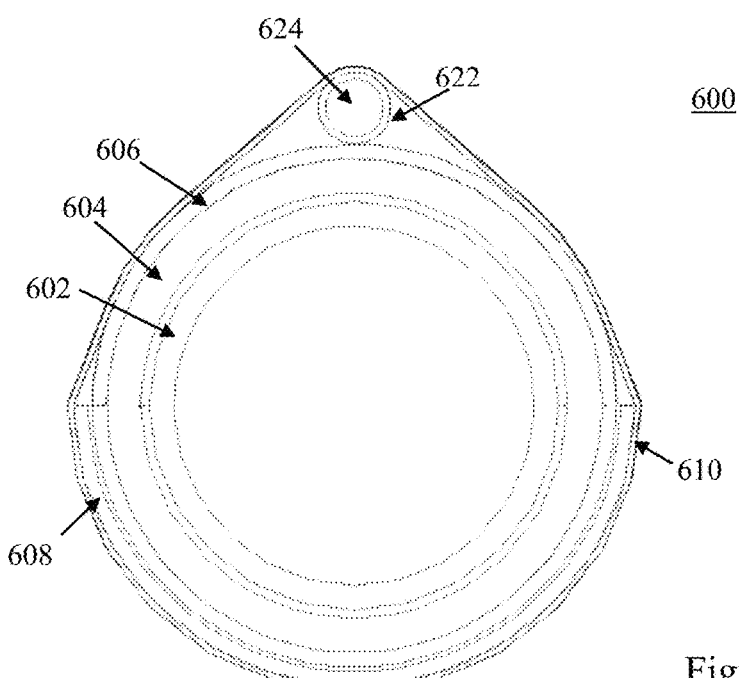
FIG. 32B is an enlarged, transverse cross-sectional view of the device of FIG. 31A.

In particular, and with additional reference to FIGS. 32A and 32B, the irrigation tube 622 defines an irrigation channel 624, and extending from a proximal end 626 (FIG. 31A) to a distal end 628. The proximal end 626 is configured for fluid connection to one or more other components of the device 600 as will be apparent to one of ordinary skill (e.g., the irrigation hubs described above) for connecting a fluid source to the irrigation channel 624. The distal end 628 is open to the irrigation channel 624 and serves as, or as part of, an irrigation outlet port 630 (referenced generally). The irrigation tube 622, and thus the irrigation channel 624 extends in a direction generally parallel with a central axis A of the inner shaft 602. In some embodiments, the irrigation tube 622 is secured relative to the outer shaft 604 by the insulating layer 610 (e.g., heat shrink assembly). The irrigation outlet port 630 is located or spaced proximal the cutting tip 612 and the first and second electrode surfaces 618, 620, and is radially outside of or beyond the outer shaft 604.

Figure 33:
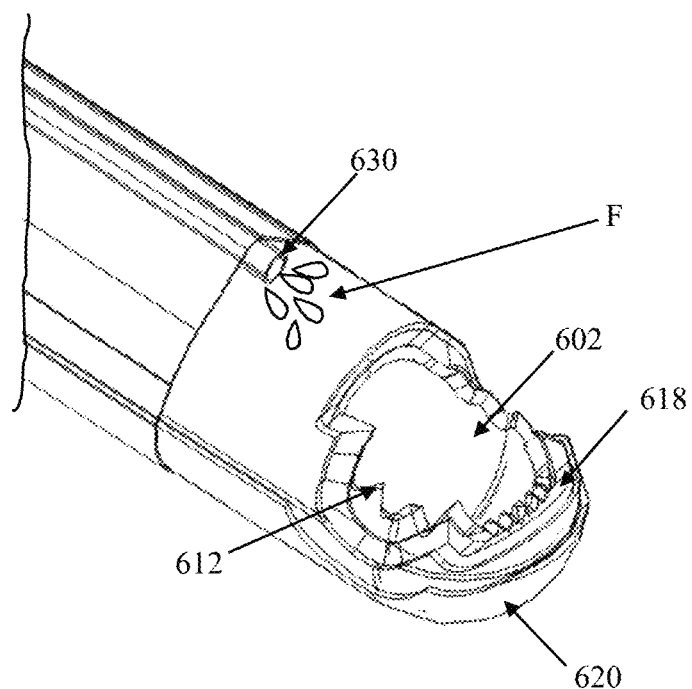
FIG. 33 is an enlarged, perspective view of a portion of the device of FIG. 31A, and illustrating delivery of fluid.

As shown in FIG. 33, fluid (e.g., saline) F delivered through the irrigation channel 624 (FIG. 32A) is dispensed to an exterior of the device 600 via the irrigation outlet port 630 and can progress into contact with the electrode surfaces 618, 620 to promote operation thereof in a bipolar mode as described above. With embodiments in which the device 600 provides suction or aspiration at the cutting tip 612 (e.g., as described above, a lumen of the inner shaft 602 can be connected to a suction source), the saline or other fluid F expressed through the irrigation outlet port 630 will not be immediately or primarily aspirated from the treatment site.

The irrigation delivery construction of the device 600, and in particular the irrigation channel 624 and irrigation outlet port 630, can be implemented into the device 600 in a relatively low cost manner. In some embodiments, it has surprisingly been found that by emitting saline (or other fluid) at a location proximally spaced from the cutting tip 612 (or other location of suction), electrical performance of the electrode surfaces 618, 620 (e.g., cautery performance) is greatly improved as compared to arrangements in which the saline (or other fluid) is emitted from between the inner and outer shafts 602, 604 at or immediately adjacent the cutting tip 612. Distinct directionality or control over the fluid F exiting the irrigation outlet port 630 is provided. The irrigation outlet port 630 can be configured to establish low pressure flow or a jet to overcome gravity in an upright orientation of the device 600.

Figure 34:
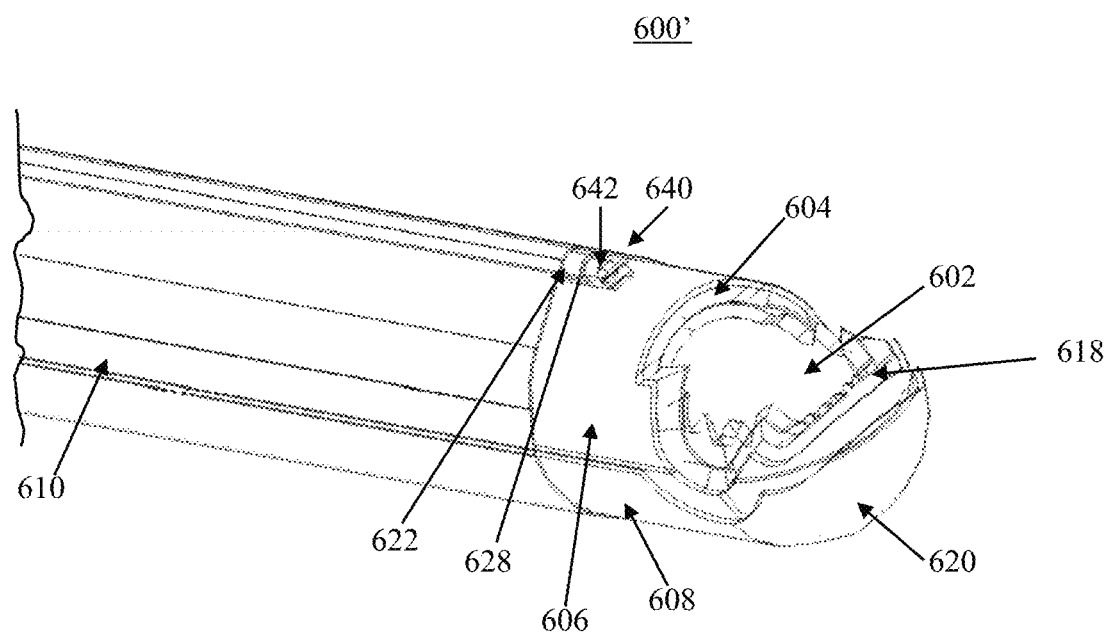
FIG. 34 is an enlarged, perspective view of a portion of another bipolar electrical surgical device in accordance with principles of the present disclosure.

Portions of another electrical surgical device 600' in accordance with principles of the present disclosure are shown in FIG. 34. The device 600' can be highly akin to the device 600 (FIG. 31A) described above, and includes the inner shaft or tubular member 602, the outer shaft or tubular member 604, the electrical insulator 606, the second electrode body or cap 608 and the insulating layer 610. The device 600' further includes the irrigation tube 622 as previously described, forming the irrigation channel 624 (hidden in FIG. 34, but shown, for example, in FIG. 32A). With the embodiment of FIG. 30, an irrigation outlet port 640 is provided at the distal end 628 of the irrigation tube 622, and includes a nozzle 642. The nozzle 642 is coupled to the distal end 628 and is fluidly open to the irrigation channel 624. The nozzle 642 can assume various forms, and in some embodiments is configured to generate a mist-like pattern into fluid (not shown) emitted from the irrigation outlet port 640 in a direction of the electrode surfaces 618, 620.

Figure 35:
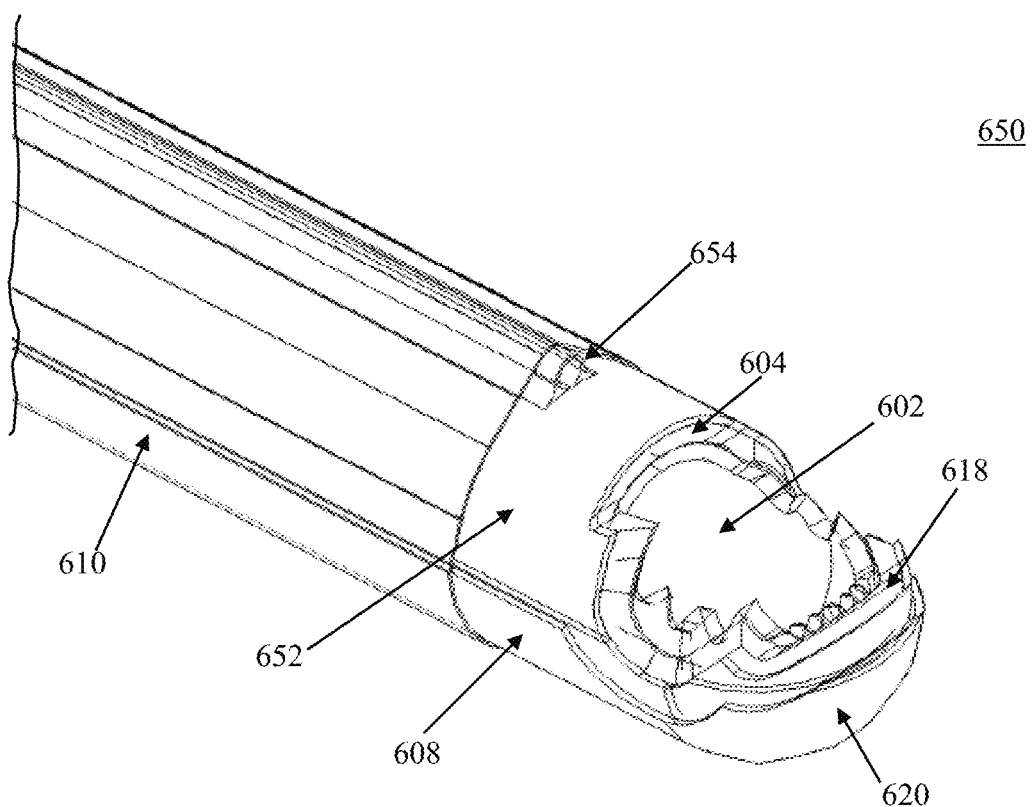
FIG. 35 is an enlarged, perspective view of a portion of another bipolar electrical surgical device in accordance with principles of the present disclosure.

Portions of another electrical surgical device 650 in accordance with principles of the present disclosure are shown in FIG. 35. The device 650 can be akin to the device 600 (FIG. 31A) described above, and includes the inner shaft or tubular member 602, the outer shaft or tubular member 604, the second electrode body or cap 608 and the insulating layer 610 as previously described (including provision of the second electrode surface 620). The device 650 further includes an electrical insulator 652 that is akin to the electrical insulator 606 (FIG. 31A), covering a majority of the outer shaft 604 in a manner defining the first electrode surface 618. In addition, the electrical insulator 652 is configured to provide an irrigation channel (primarily hidden in FIG. 35) and an irrigation outlet port 654 as described below. As compared to the device 600, the electrical insulator 652 replaces the irrigation tube 622 (FIG. 31B).

Figure 36A:
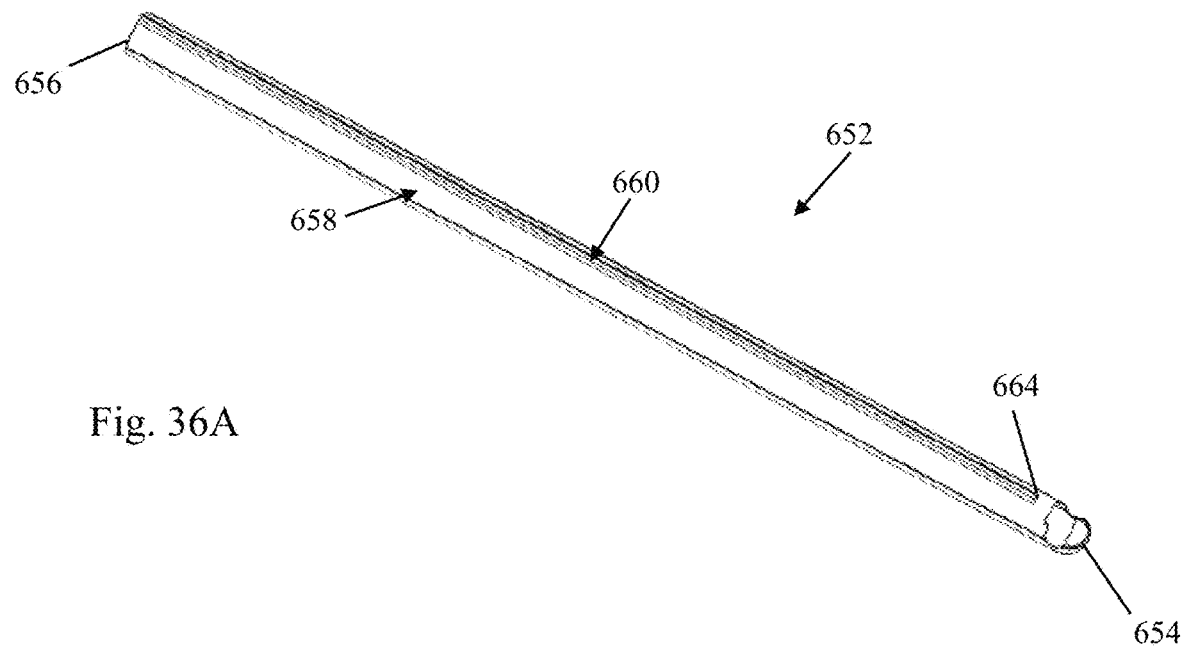
FIG. 36A is a perspective view of an electrical insulator component useful with the device of FIG. 35.
Figure 36B:
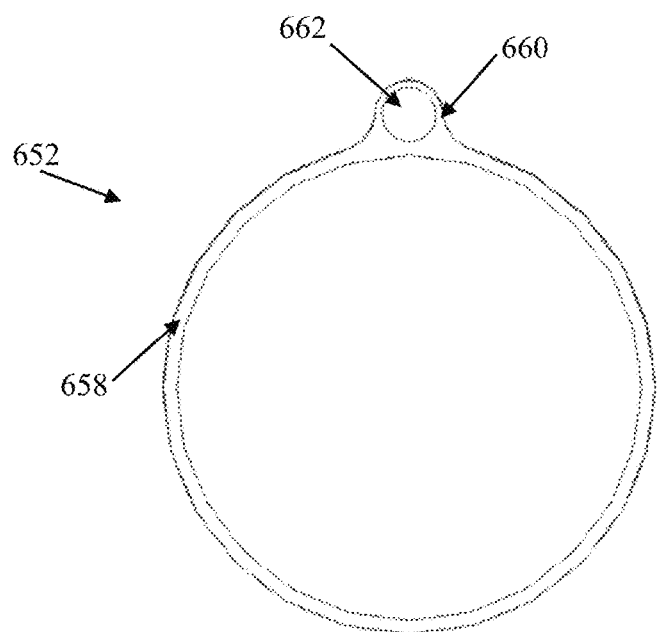
FIG. 36B is an enlarged, transverse cross-sectional view of the electrical insulator of FIG. 36A.

The electrical insulator 652 is shown in greater detail in FIGS. 36A and 36B, and extends between a leading end 654 and a trailing end 656. The electrical insulator 652 includes or is formed to define an insulating region 658 and an irrigation region 660. The insulating region 658 is commensurate with previous embodiments, and corresponds in size and shape with the outer shaft 604 (FIG. 35). For example, the insulating region 658 can be formed by coating a material of the electrical insulator on to an exterior surface of the outer shaft 604. Regardless, the irrigation region 660 is radially off-set from the insulating region 658, and has a tubular shape defining the irrigation channel 662. The irrigation channel 662 is open at the trailing end 656, and is configured for fluid connection to one or more other components of the device 650 (FIG. 35) as will be apparent to one of ordinary skill (e.g., the irrigation hubs described above) for connecting a fluid source to the irrigation channel 662. Further, the irrigation channel 662 is open at a distal end 664 of the irrigation region 660 (with the distal end 664 being proximally spaced from the leading end 654).

Figure 37A:
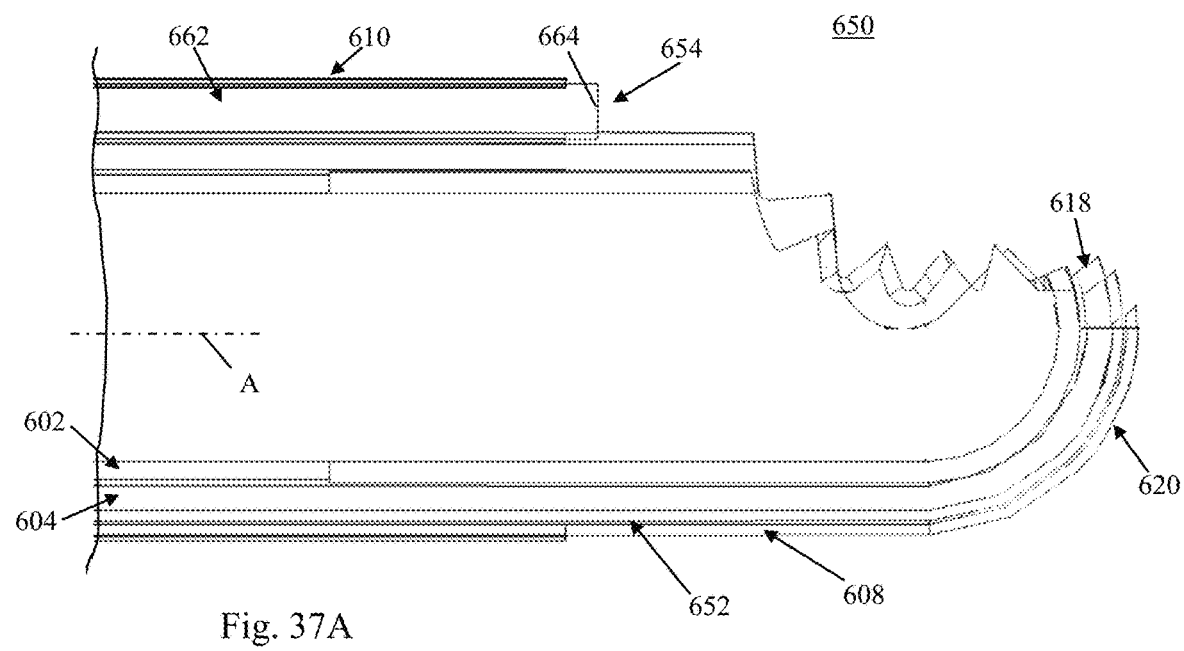
FIG. 37A is an enlarged, longitudinal cross-sectional view of a portion of the device of FIG. 35.
Figure 37B:
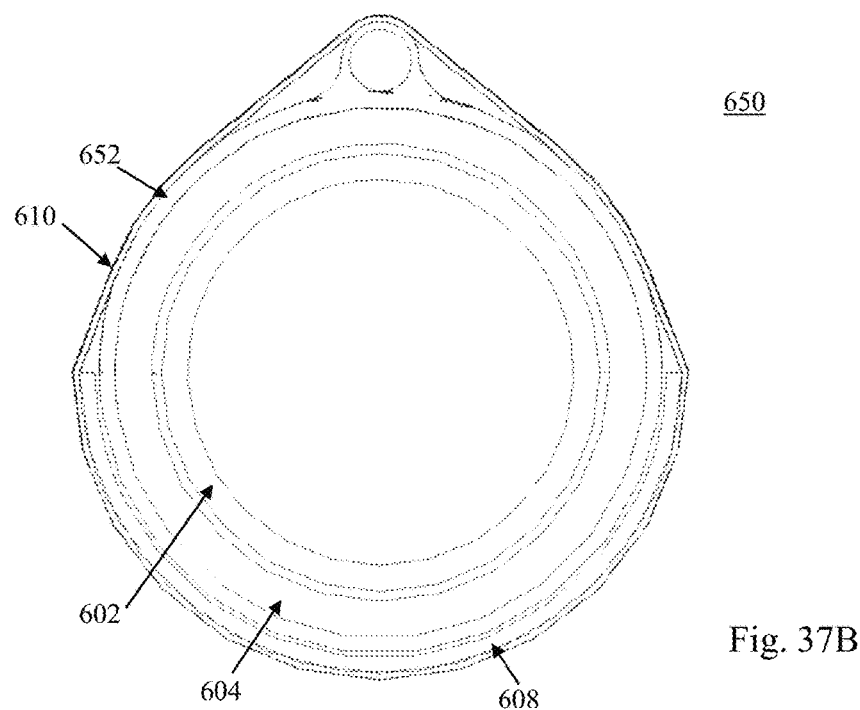
FIG. 37B is an enlarged, transverse cross-sectional view of the device of FIG. 35.

With the above construction, and as shown in FIGS. 37A and 37B, the electrical insulator 652 electrically isolates the outer shaft 604 from the second electrode body 608 except in a region of the first electrode surface 618. The distal end 664 is open to the irrigation channel 662 and serves as, or as part of, the irrigation outlet port 654 (referenced generally). The irrigation channel 662 extends in a direction generally parallel with a central axis A of the inner shaft 602. The irrigation outlet port 654 is located or spaced proximal the cutting tip 612 and the first and second electrode surfaces 618, 620, and is radially outside of or beyond the outer shaft 604.

Figure 38:
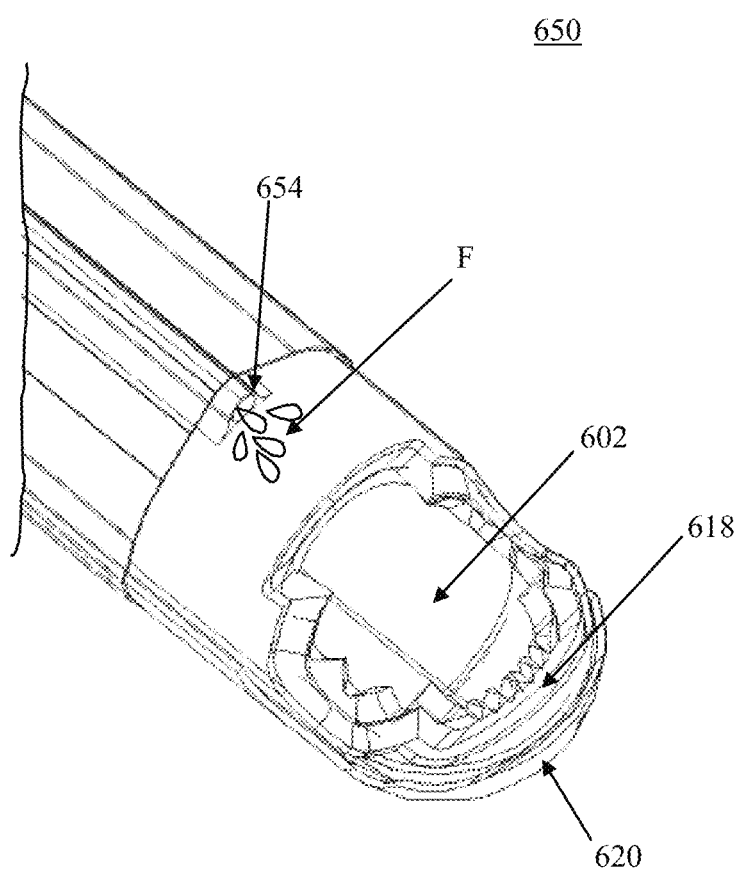
FIG. 38 is an enlarged, perspective view of a portion of the device of FIG. 35, and illustrating delivery of fluid.

As shown in FIG. 38, fluid (e.g., saline) F delivered through the irrigation channel 662 (FIG. 37A) is dispensed to an exterior of the device 650 via the irrigation outlet port 654 and can progress into contact with the electrode surfaces 618, 620 to promote operation thereof in a bipolar mode as described above. With embodiments in which the device 650 provides suction or aspiration at the cutting tip 612 (e.g., as described above, a lumen of the inner shaft 602 can be connected to a suction source), the saline or other fluid F expressed through the irrigation outlet port 654 will not be immediately or primarily aspirated from the treatment site.

The irrigation delivery construction of the device 650, and in particular the irrigation channel 662 (FIG. 37A) and irrigation outlet port 654, can be implemented into the device 650 in a relatively low cost manner. In some embodiments, it has surprisingly been found that by emitting saline (or other fluid) at a location proximally spaced from the cutting tip 612 (or other location of suction), electrical performance of the electrode surfaces 618, 620 (e.g., cautery performance) is greatly improved as compared to arrangements in which the saline (or other fluid) is emitted from between the inner and outer shaft 602, 604 at or immediately adjacent the cutting tip 612. Distinct directionality or control over the fluid F exiting the irrigation outlet port 654 is provided. The irrigation outlet port 654 can be configured to establish low pressure flow or a jet to overcome gravity in an upright orientation of the device 650.

Figure 39A:
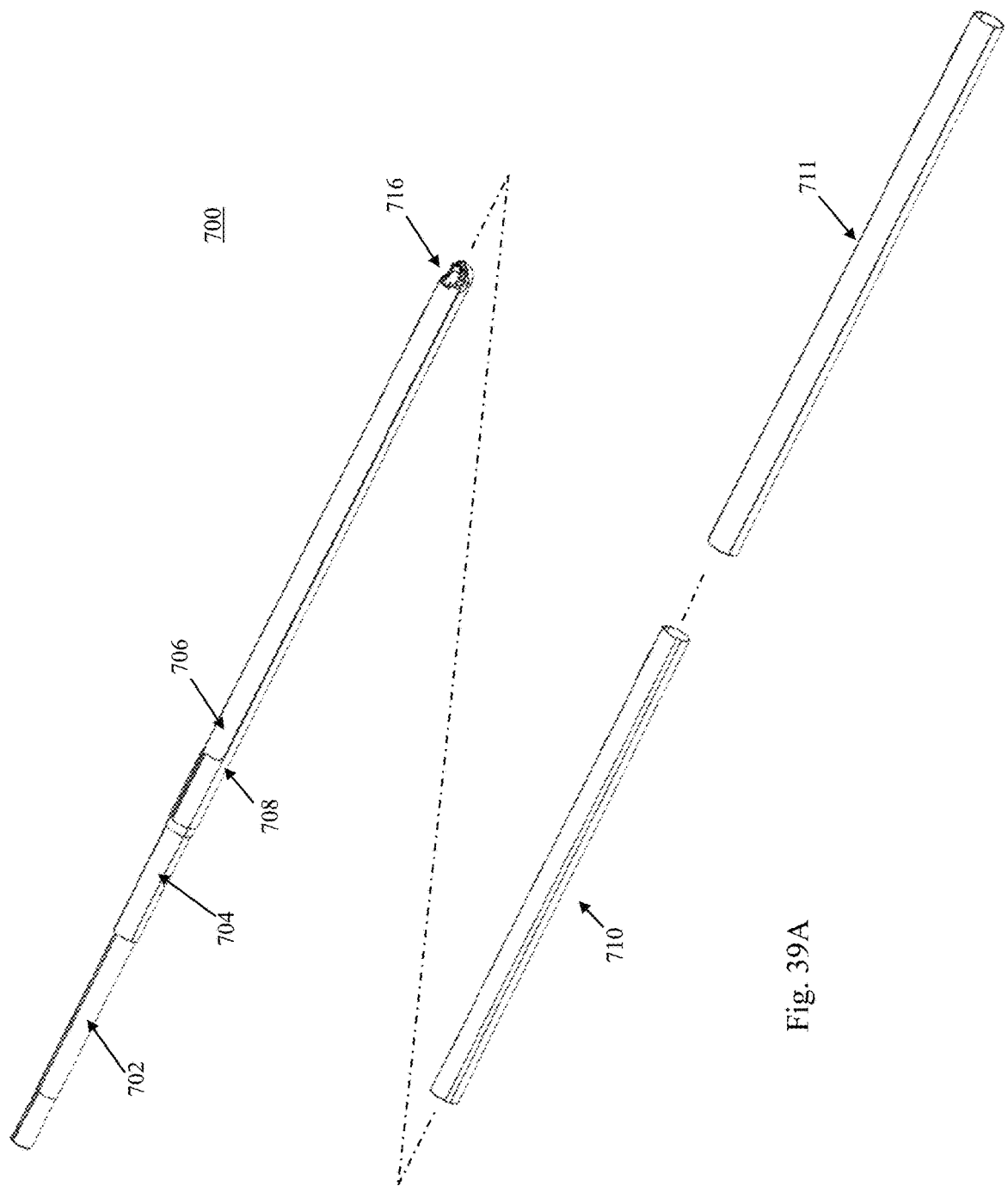
FIG. 39A is an exploded, perspective view of a portion of another bipolar electrical surgical device in accordance with principles of the present disclosure.
Figure 39B:
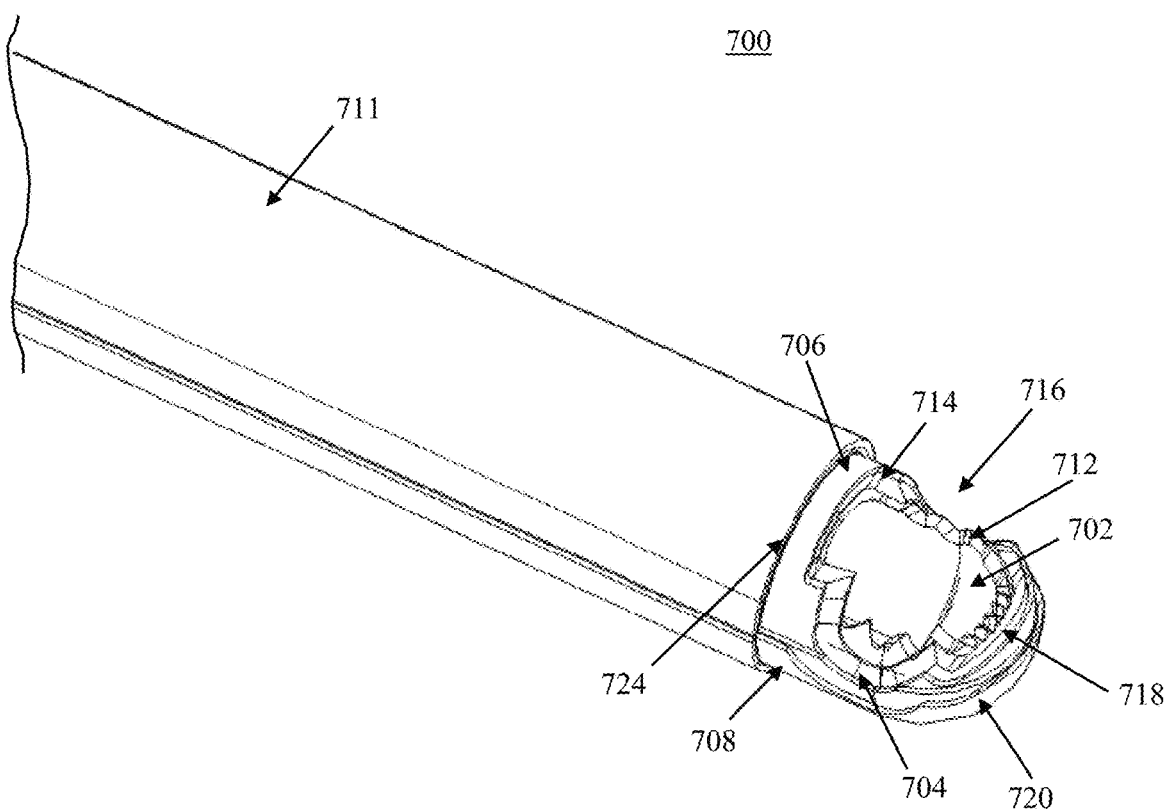
FIG. 39B is an enlarged, perspective view of a portion of the device of FIG. 39A upon final assembly.

Portions of another electrical surgical device 700 in accordance with principles of the present disclosure are shown in FIGS. 39A and 39B. In particular, blade and electrode assembly components of the device 700 are shown and described below. For ease of explanation, various other components of the device 700 are omitted from the views; for example, the device 700 can include one or more of the various housings, hubs and electrical connections components described above with respect to the device 110 (FIG. 2A), or equivalent components or mechanisms. With this in mind, the device 700 includes an inner shaft or tubular member 702, an outer shaft or tubular member 704, an electrical insulator 706, a second electrode body or cap 708, and an insulating layer 710. The components 702-710 can be akin to previous embodiments. Further, the device 700 includes an outer layer 711 for reasons made clear below.

In general terms, and akin to the embodiments above, the inner shaft 702 is rotatably disposed within the outer shaft 704 and forms a cutting tip 712. The cutting tip 712 is selectively exposed at a cutting window 714 of the outer shaft 704. The cutting tip 712 and the cutting window 714 combine to define a cutting implement 716. The electrical insulator 706 covers a majority of an exterior of the outer shaft 704. The outer shaft 704 is formed of an electrically conductive material and thus can serve as a first electrode body of the device 700. A distal portion of the outer shaft 704 is free of the electrical insulator 716, defining a first electrode surface 718. The second electrode body 708 receives the outer shaft 704 (coated with the electrical insulator 706). The insulating layer 710 (hidden in FIG. 39B) covers a majority of an exterior of the second electrode body 708, optionally securing the second electrode body 708 to the outer shaft 704 (e.g., via heat shrink process). A distal region of the second electrode body 708 is free of the insulating layer 710, defining a second electrode surface 720.

The device 700 operates in a manner highly akin to the device 110 (FIG. 2A) as described above, with the inner shaft 702 powered to rotate or oscillate relative to the outer shaft 704 to perform tissue cutting, dissection, etc., at the cutting implement 716. Further, the electrode surfaces 718, 720 can be operated as bipolar electrodes as described above. In addition, the device 700 is configured to provide irrigation in a region of the electrode surfaces 718, 720 as described below.

Figure 40A:
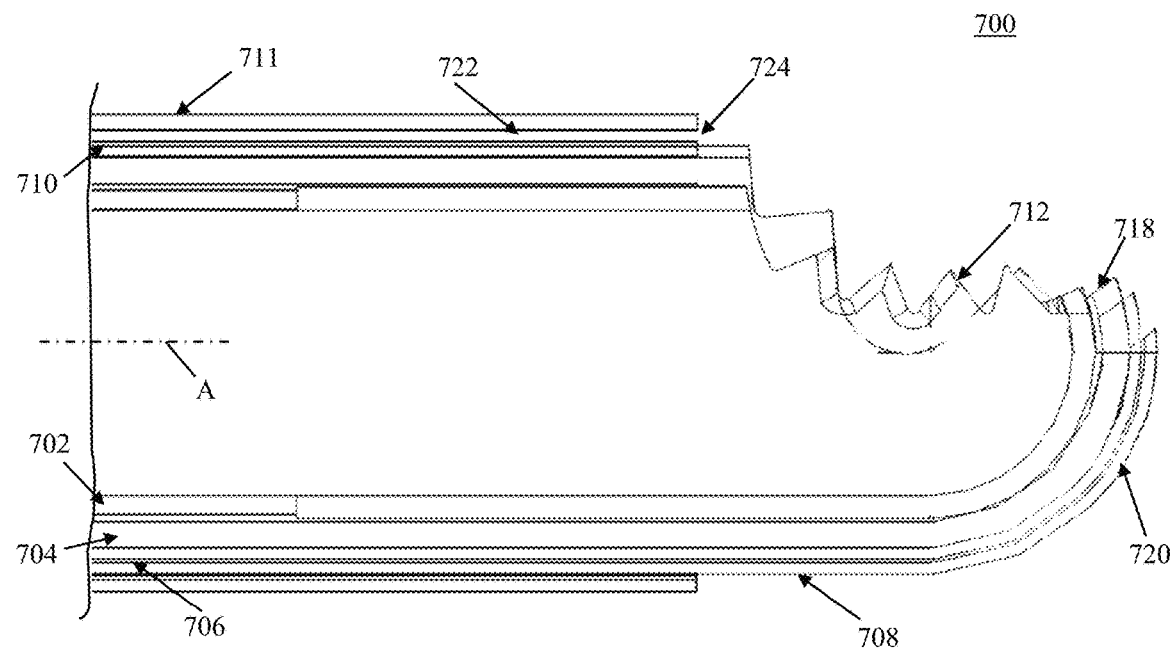
FIG. 40A is an enlarged, longitudinal cross-sectional view of a portion of the device of FIG. 39A.
Figure 40B:
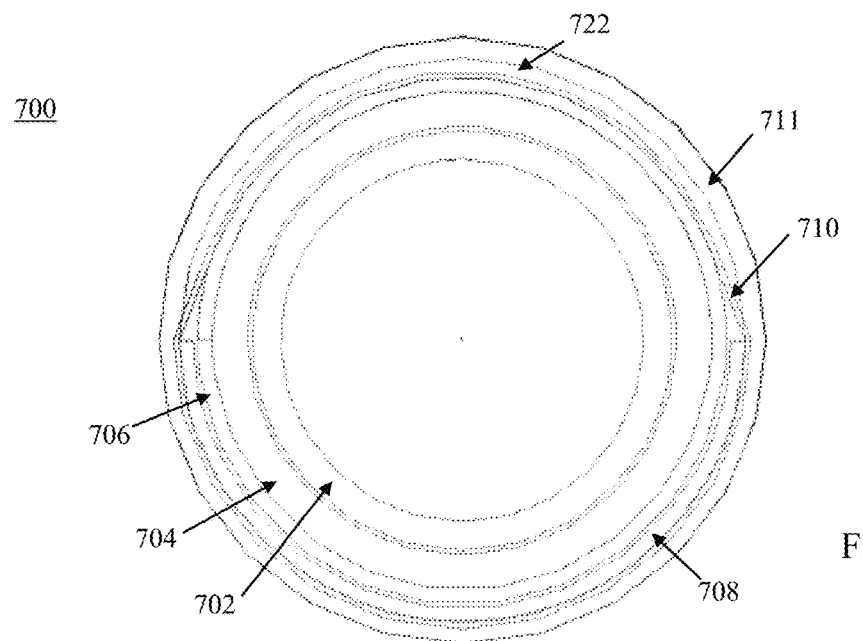
FIG. 40B is an enlarged, transverse cross-sectional view of the device of FIG. 39A.

In particular, and with additional reference to FIGS. 40A and 40B, the outer layer 711 is disposed about the insulating layer 710. An inner diameter or shape of the inner layer 711 is greater than an outer diameter or shape of the insulating layer 710. The difference in diameter or shape generates an irrigation channel 722 between the insulating and outer layers 710, 711. The irrigation channel 722 extends in a direction generally parallel with a central axis A of the inner shaft 702. In some embodiments, the outer layer 711 is formed to maintain the shape illustrated, dictating that the irrigation channel 722 is along a side of the device 700 opposite the second electrode body 708. That is to say, the outer layer 711 can be secured to and flush against the insulating layer 710 in a region corresponding with the second electrode body 708 and is free of (and spaced from) the insulating layer 710 in a region opposite the second electrode body 708 to generate the irrigation channel 722. The irrigation channel 722 terminates at or is fluidly open to at least one fluid outlet or irrigation outlet port 724 (identified in FIGS. 39B and 40A). The irrigation outlet port 724 is located or spaced proximal the cutting tip 712 and the first and second electrode surfaces 718, 720, and is radially outside of or beyond the outer shaft 704. In some embodiments, the irrigation outlet port 724 is opposite the second electrode body 708. Though not visible in the views, the insulation and outer layers 710, 711 are configured to establish an open proximal end for the irrigation channel 722 that is constructed for fluid connection to one or more other components of the device 700 as will be apparent to one of ordinary skill (e.g., the irrigation hubs described above) for connecting a fluid source to the irrigation channel 722.

Figure 41:
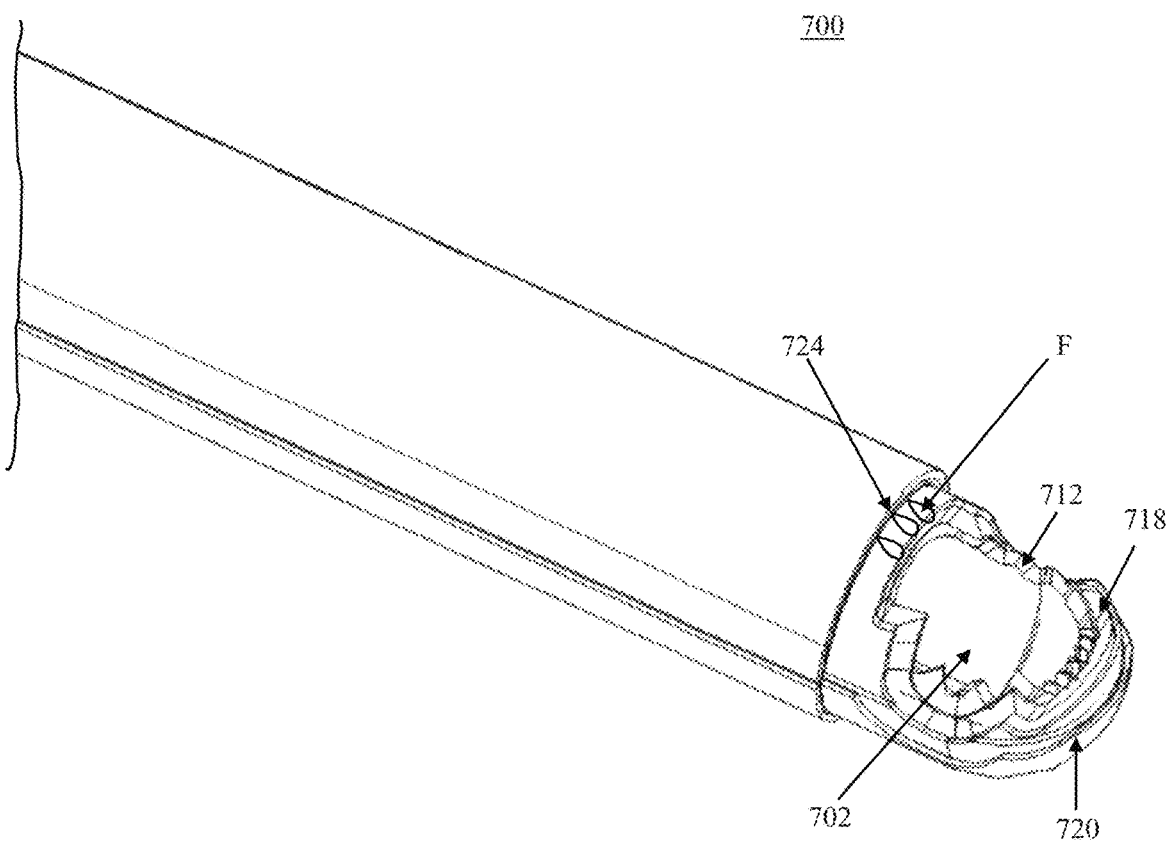
FIG. 41 is an enlarged, perspective view of a portion of the device of FIG. 39A, and illustrating delivery of fluid.

As shown in FIG. 41, fluid (e.g., saline) F delivered through the irrigation channel 722 (FIG. 40B) is dispensed to an exterior of the device 700 via the irrigation outlet port 724, and can progress into contact with the electrode surfaces 718, 720 to promote operation thereof in a bipolar mode as described above. With embodiments in which the device 700 provides suction or aspiration at the cutting tip 712 (e.g., as described above, a lumen of the inner shaft 702 can be connected to a suction source), the saline or other fluid F expressed from the irrigation outlet port 724 will not be immediately or primarily aspirated from the treatment site. Directionality or control over the fluid F exiting the irrigation outlet port 724 is generally provided.

Figure 42A:
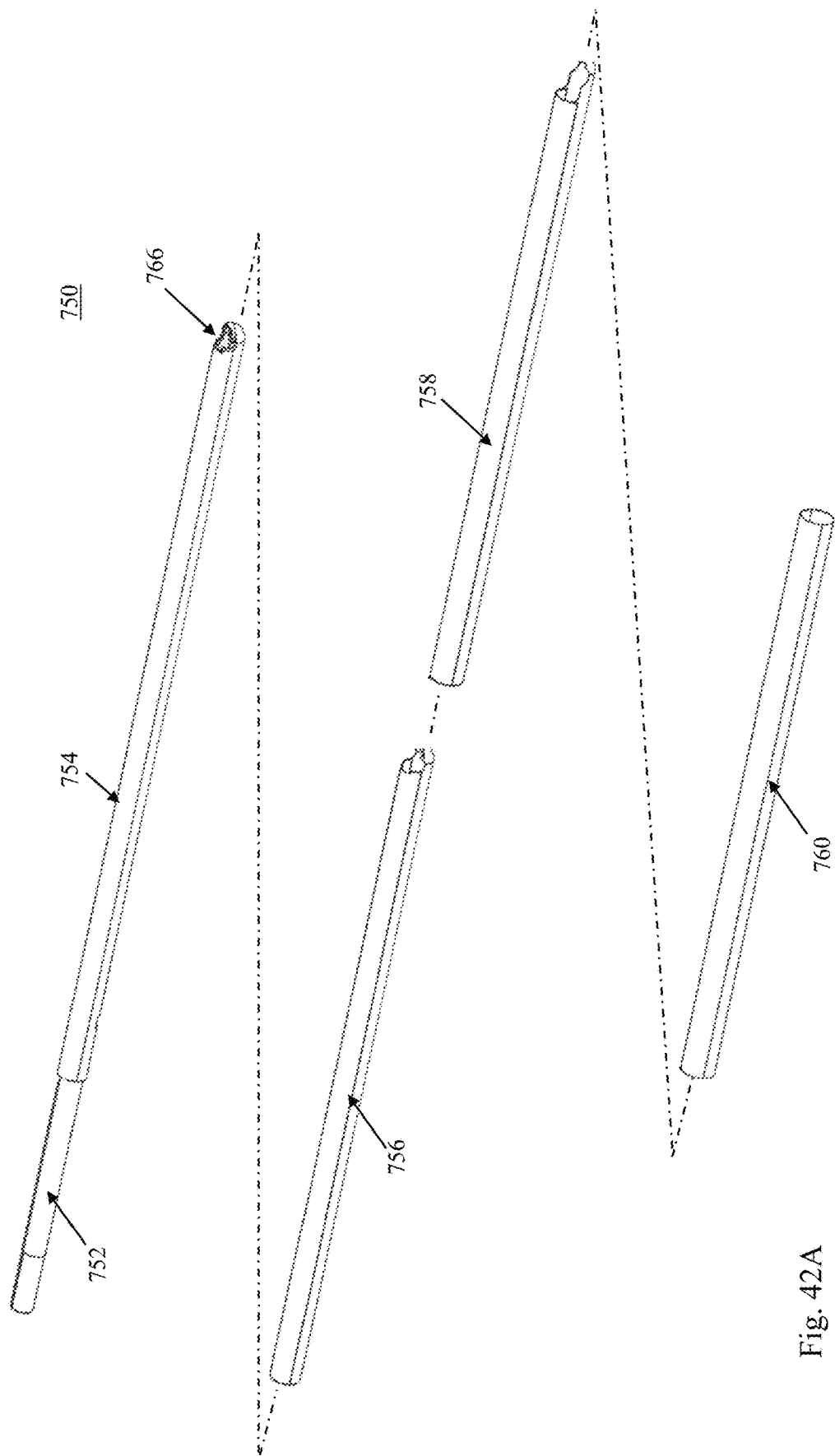
FIG. 42A is an exploded, perspective view of a portion of another bipolar electrical surgical device in accordance with principles of the present disclosure.
Figure 42B:
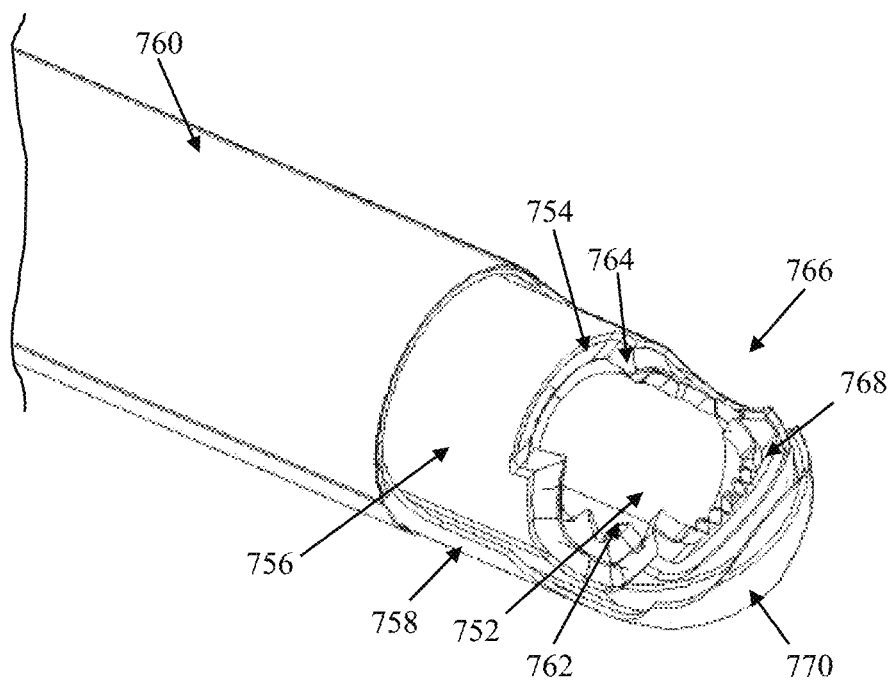
FIG. 42B is an enlarged, perspective view of a portion of the device of FIG. 42A upon final assembly.

Portions of another electrical surgical device 750 in accordance with principles of the present disclosure are shown in FIGS. 42A and 42B. In particular, blade and electrode assembly components of the device 750 are shown and described below. For ease of explanation, various other components of the device 750 are omitted from the views; for example, the device 750 can include one or more of the various housings, hubs and electrical connections components described above with respect to the device 110 (FIG. 2A), or equivalent components or mechanisms. With this in mind, the device 750 includes an inner shaft or tubular member 752, an outer shaft or tubular member 754, an electrical insulator 756, a second electrode body or cap 758, and an insulating layer 760. The inner shaft 752, outer shaft 754, electrical insulator 756 and the insulating layer 760 can have any of the constructions described above. The second electrode body 758 is configured to establish an irrigation channel as described below.

In general terms, and akin to the embodiments above, the inner shaft 752 is rotatably disposed within the outer shaft

754 and forms a cutting tip 762. The cutting tip 762 is selectively exposed at a cutting window 764 of the outer shaft 754. The cutting tip 762 and the cutting window 764 combine to define a cutting implement 766. The electrical insulator 756 covers a majority of an exterior of the outer shaft 754. The outer shaft 754 is formed of an electrically conductive material and thus can serve as a first electrode body of the device 750. A distal portion of the outer shaft 754 is free of the electrical insulator 756, defining a first electrode surface 768. The second electrode body 758 receives the outer shaft 754 (coated with the electrical insulator 756). The insulating layer 760 covers a majority of an exterior of the second electrode body 758, optionally securing the second electrode body 758 to the outer shaft 754 (e.g., via heat shrink process). A distal region of the second electrode body 758 is free of the insulating layer 760, defining a second electrode surface 770.

The device 750 operates in a manner highly akin to the device 110 (FIG. 2A) as described above, with the inner shaft 752 powered to rotate or oscillate relative to the outer shaft 754 to perform tissue cutting, dissection, etc., at the cutting implement 766. Further, the electrode surfaces 768, 770 can be operated as bipolar electrodes as described above. In addition, the device 750 is configured to provide irrigation in a region of the electrode surfaces 768, 770 as described below.

Figure 43A:
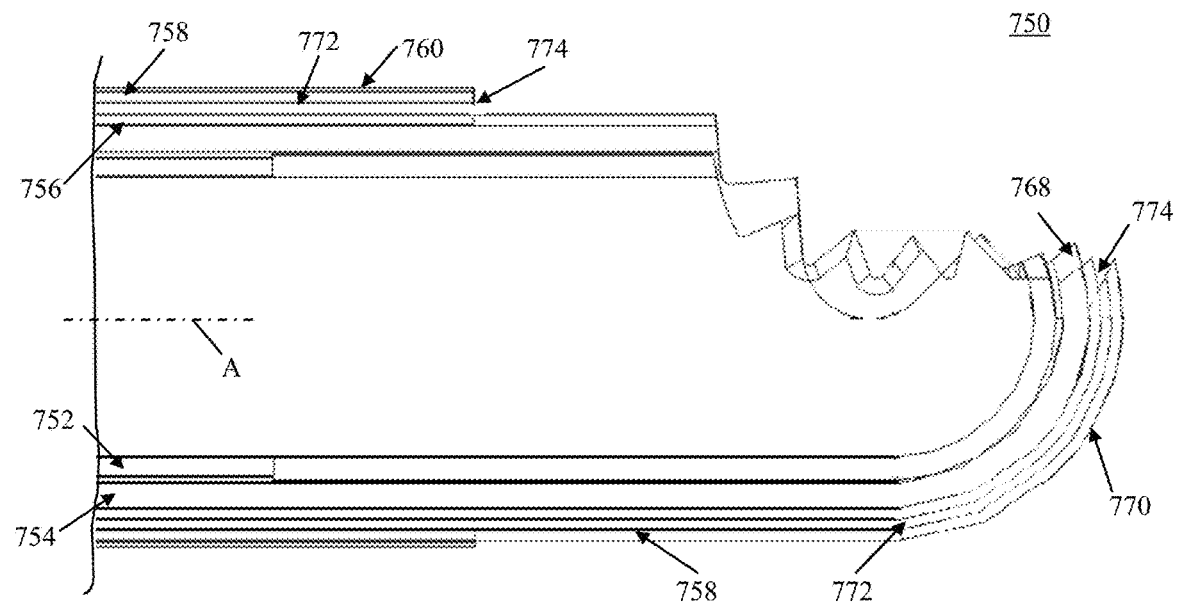
FIG. 43A is an enlarged, longitudinal cross-sectional view of a portion of the device of FIG. 42A.
Figure 43B:
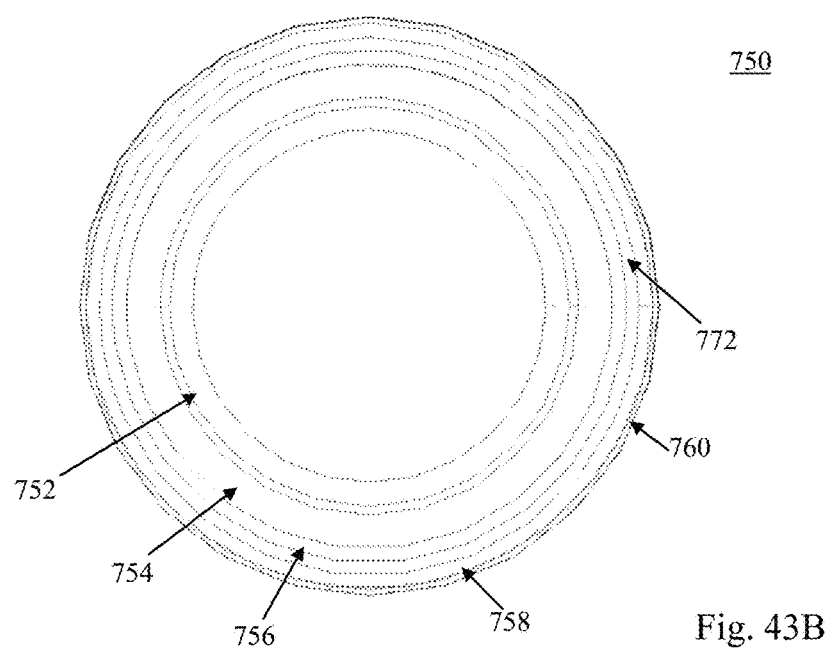
FIG. 43B is an enlarged, transverse cross-sectional view of the device of FIG. 42A.

In particular, and with additional reference to FIGS. 43A and 43B, unlike other embodiments, the second electrode body 758 is cylindrical or ring-shaped (as best reflected in FIG. 42A). While the second electrode body 758 is disposed about the electrical insulator 756 (and the insulating layer 760 is disposed about the second electrode body 758), an inner diameter of the inner layer second electrode body 758 is greater than an outer diameter of the electrical insulator 756. The difference in diameter generates an irrigation channel 772 between the electrical insulator 756 and the second electrode body 758. The irrigation channel 772 extends in a direction generally parallel with a central axis A of the inner shaft 752 and can be viewed as being annular or ring shaped, circumscribing an exterior of the electrical insulator 756. The irrigation channel 772 terminates at or is fluidly open to at an irrigation outlet port 774 (identified in FIG. 43A). At least a portion of the irrigation outlet port 774 is located or spaced proximal the cutting tip 762 and the first and second electrode surfaces 768, 770, and is radially outside of or beyond the outer shaft 754. Though not visible in the views, the electrical insulator 756 and the second electrode body 758 are configured to establish an open proximal end for the irrigation channel 772 that is constructed for fluid connection to one or more other components of the device 750 as will be apparent to one of ordinary skill (e.g., the irrigation hubs described above) for connecting a fluid source to the irrigation channel 772.

Figure 44:
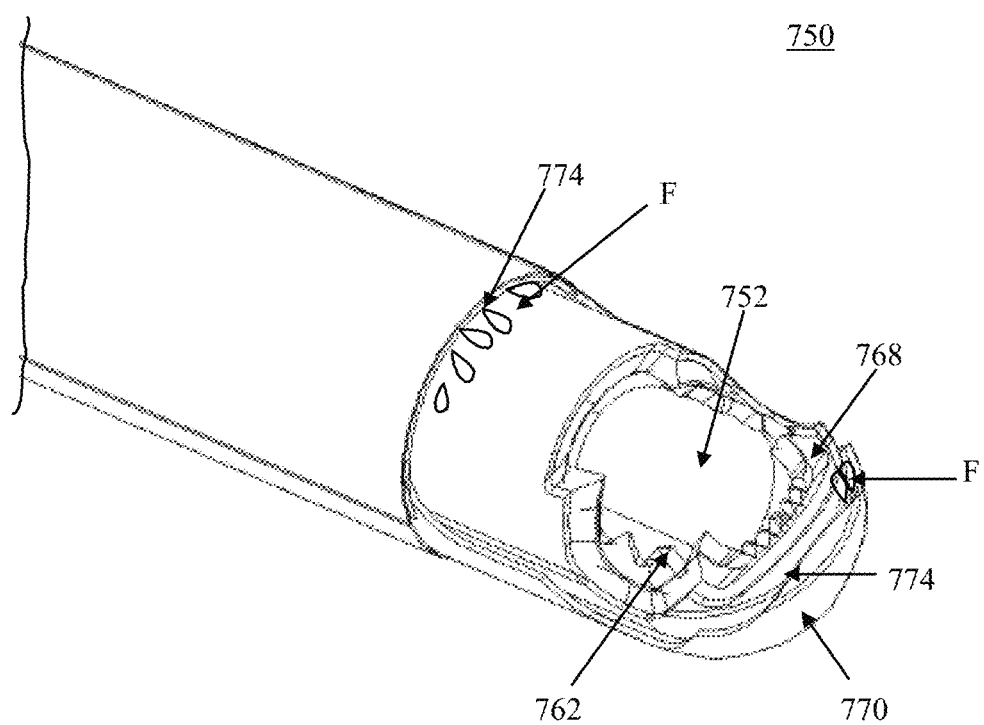
FIG. 44 is an enlarged, perspective view of a portion of the device of FIG. 42A, and illustrating delivery of fluid.
Figure 45B:
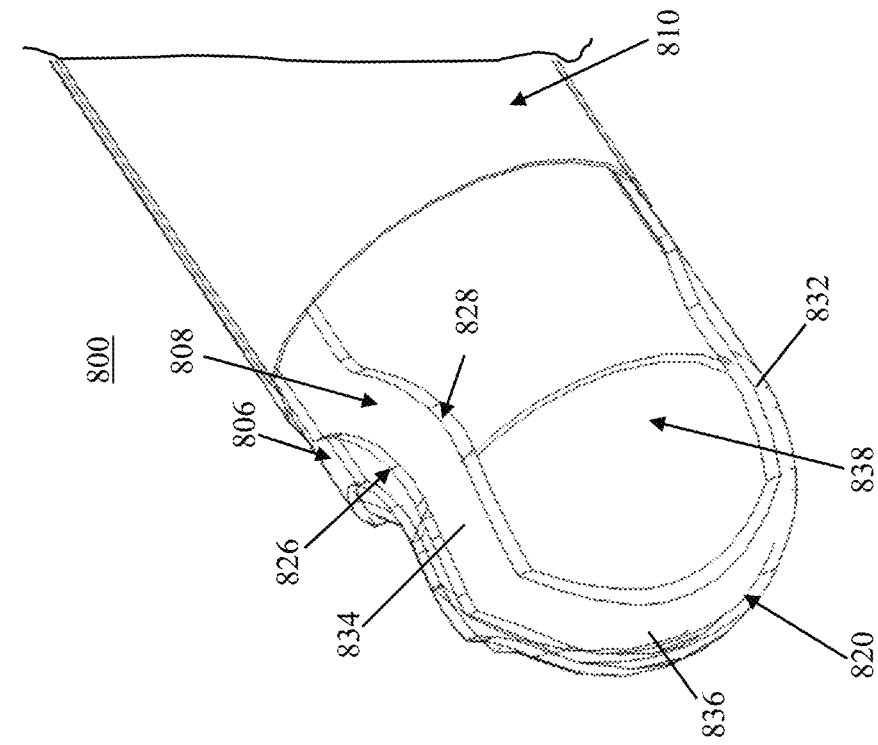
FIG. 45B is a bottom perspective view of the device of FIG. 45A.
Figure 45A:
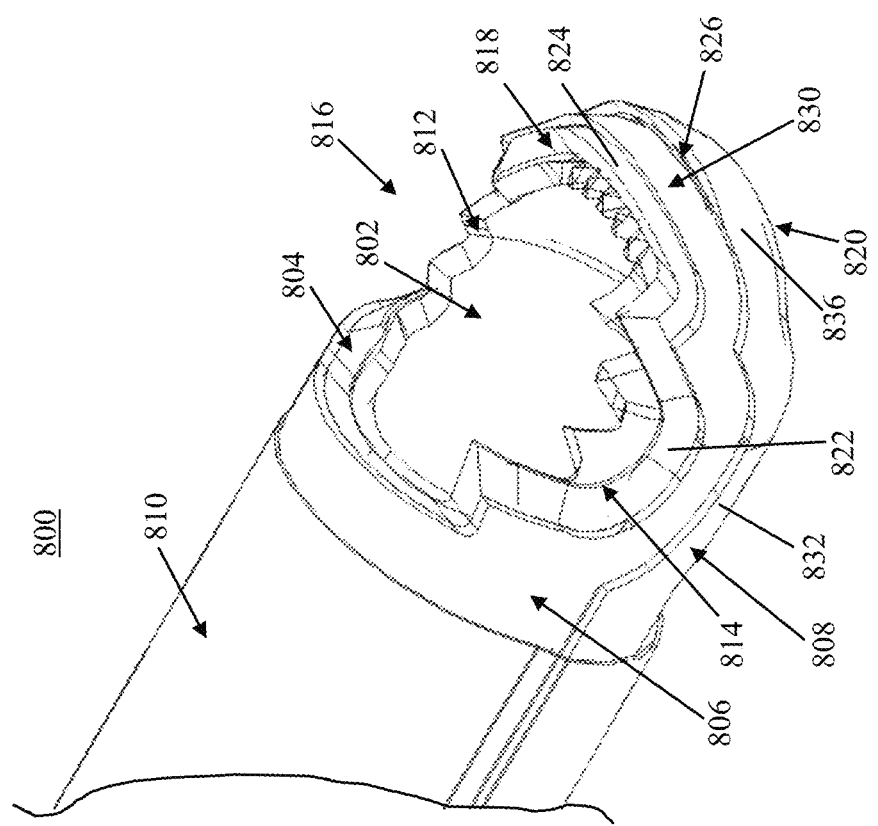
FIG. 45A is an enlarged, top perspective view of a portion of another bipolar electrical surgical device in accordance with principles of the present disclosure.
Figure 45C:
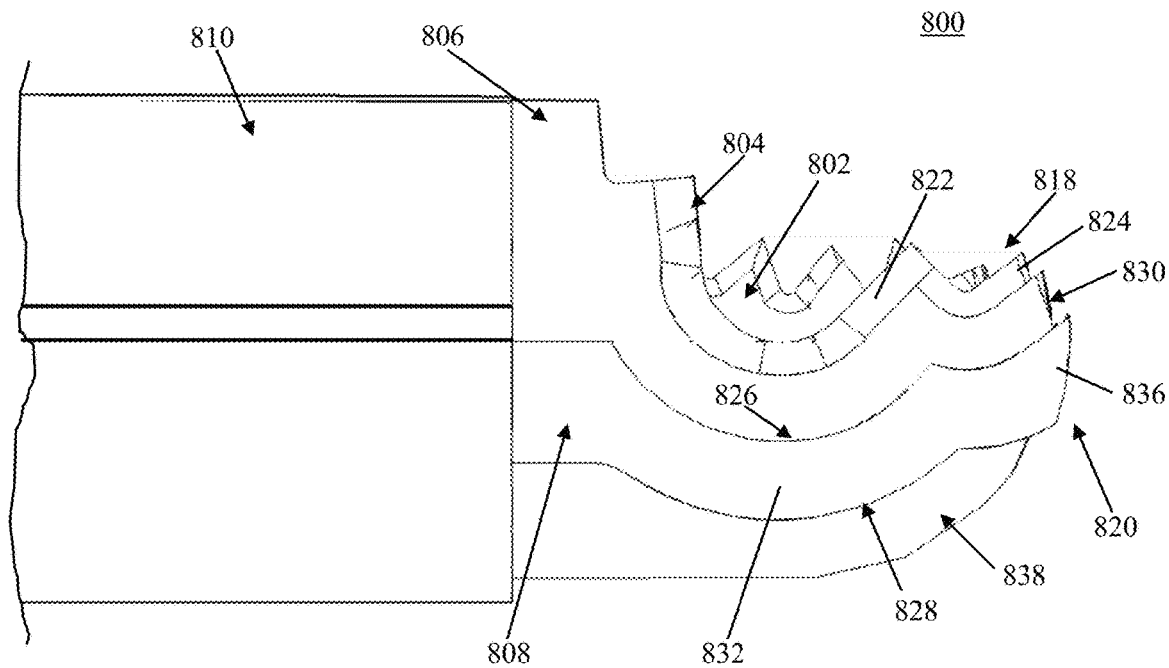
FIG. 45C is an enlarged side view of a portion of the device of FIG. 45A.
Figure 45D:
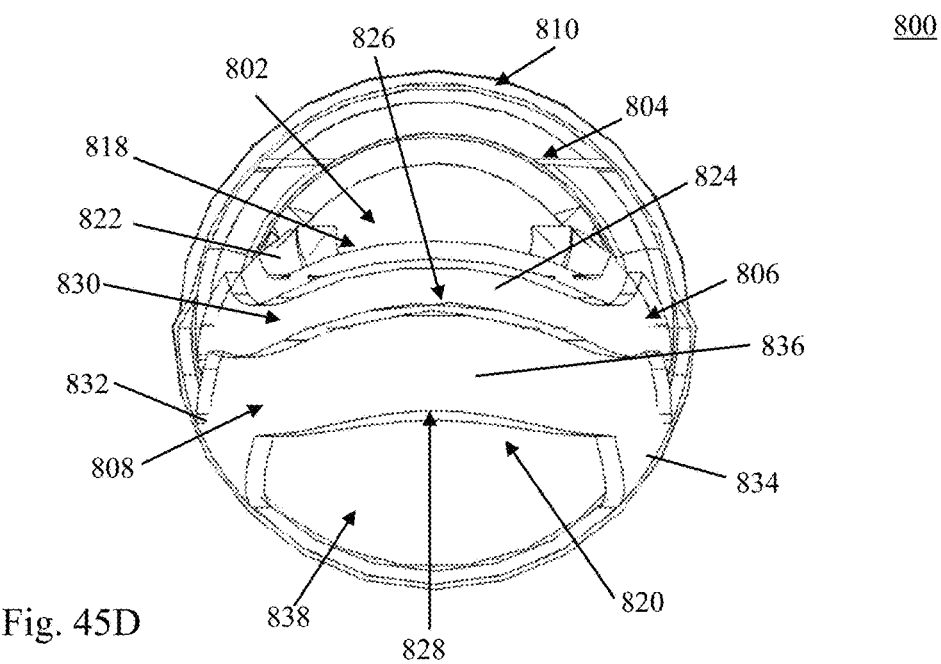
FIG. 45D is an enlarged front view of the device of FIG. 45A.
Figure 46C:
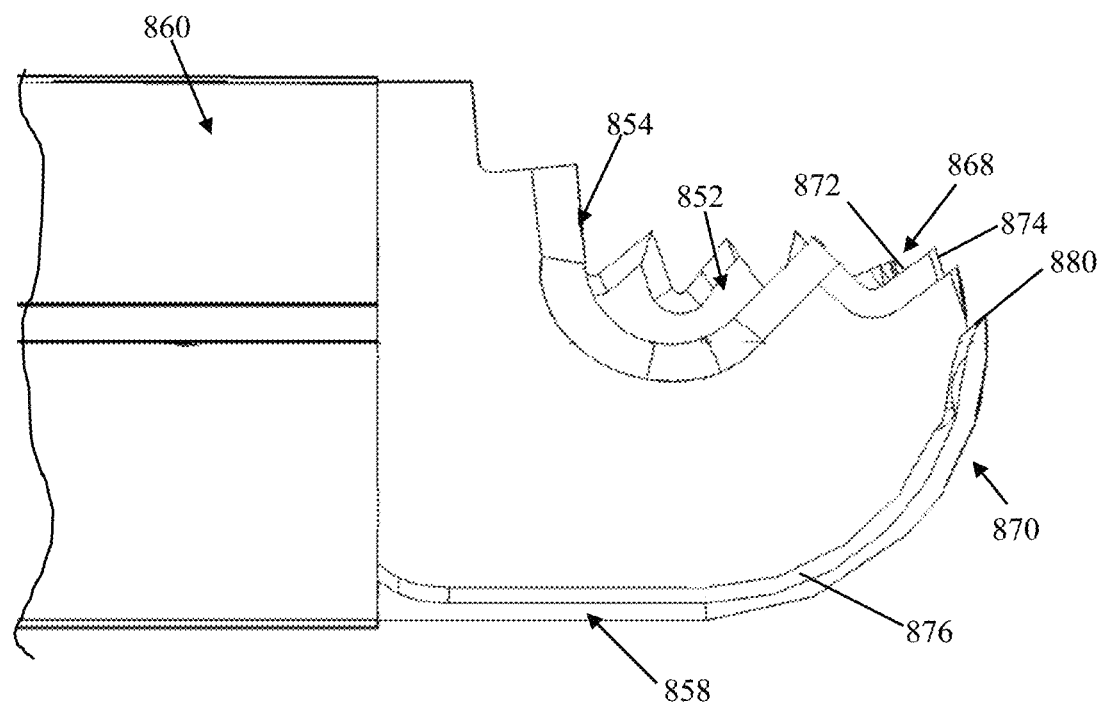
FIG. 46C is an enlarged side view of a portion of the device of FIG. 46A.
Figure 46D:
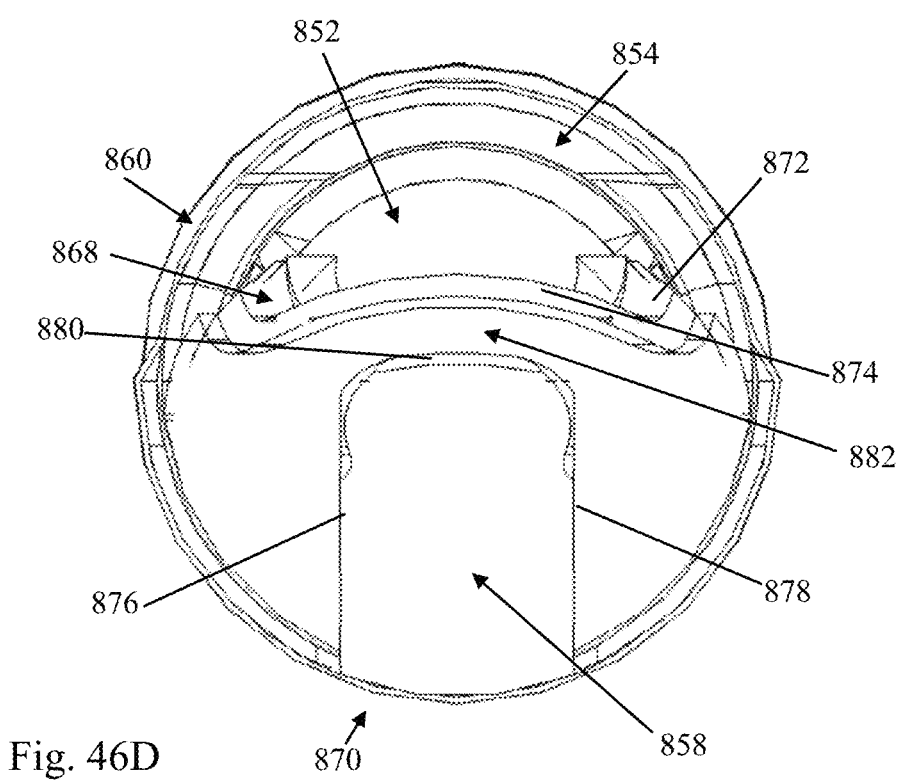
FIG. 46D is an enlarged front view of the device of FIG. 46A.
Figure 47B:
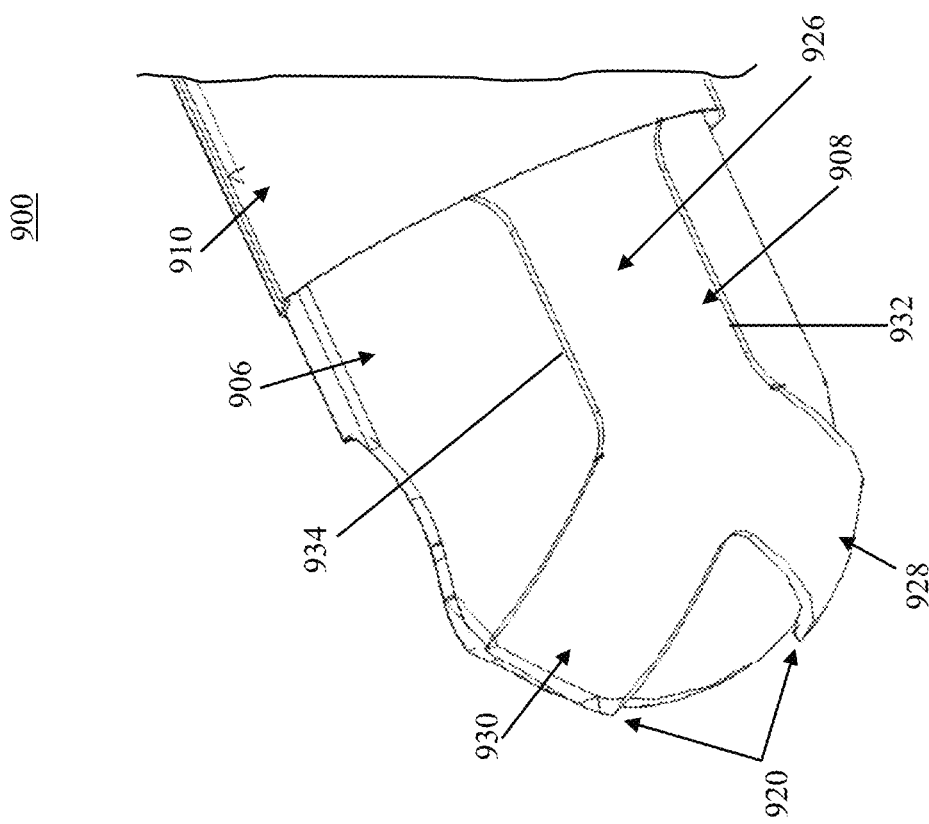
FIG. 47B is a bottom perspective view of the device of FIG. 47A.
Figure 47A:
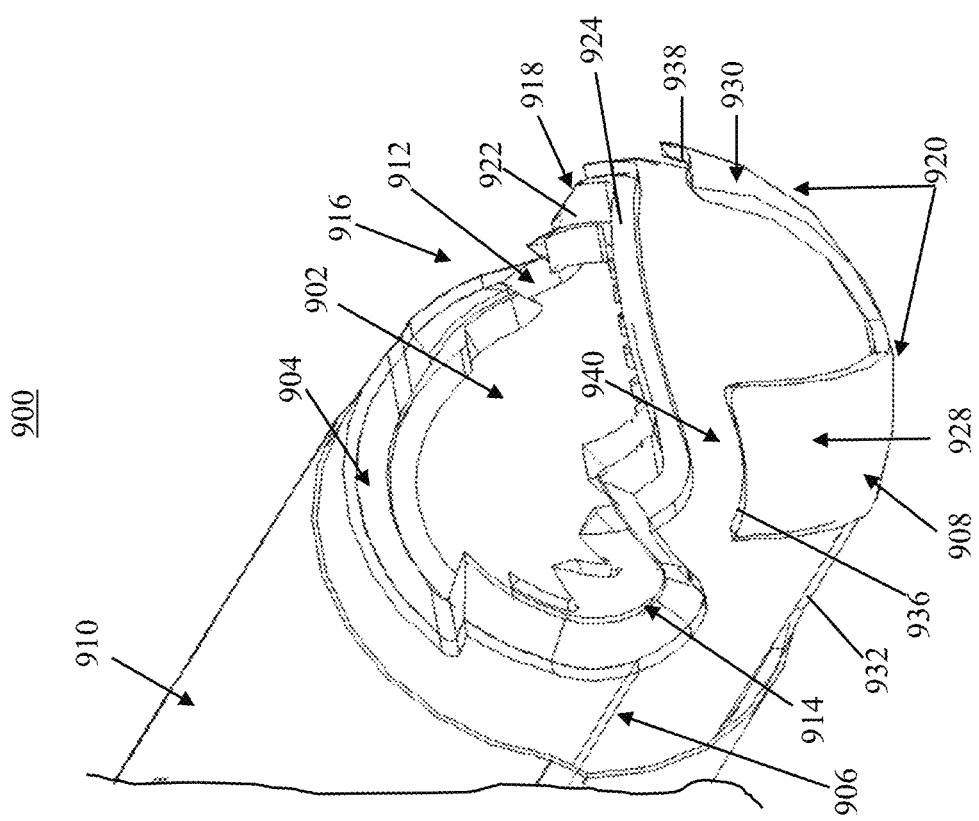
FIG. 47A is an enlarged, top perspective view of a portion of another bipolar electrical surgical device in accordance with principles of the present disclosure.
Figure 47C:
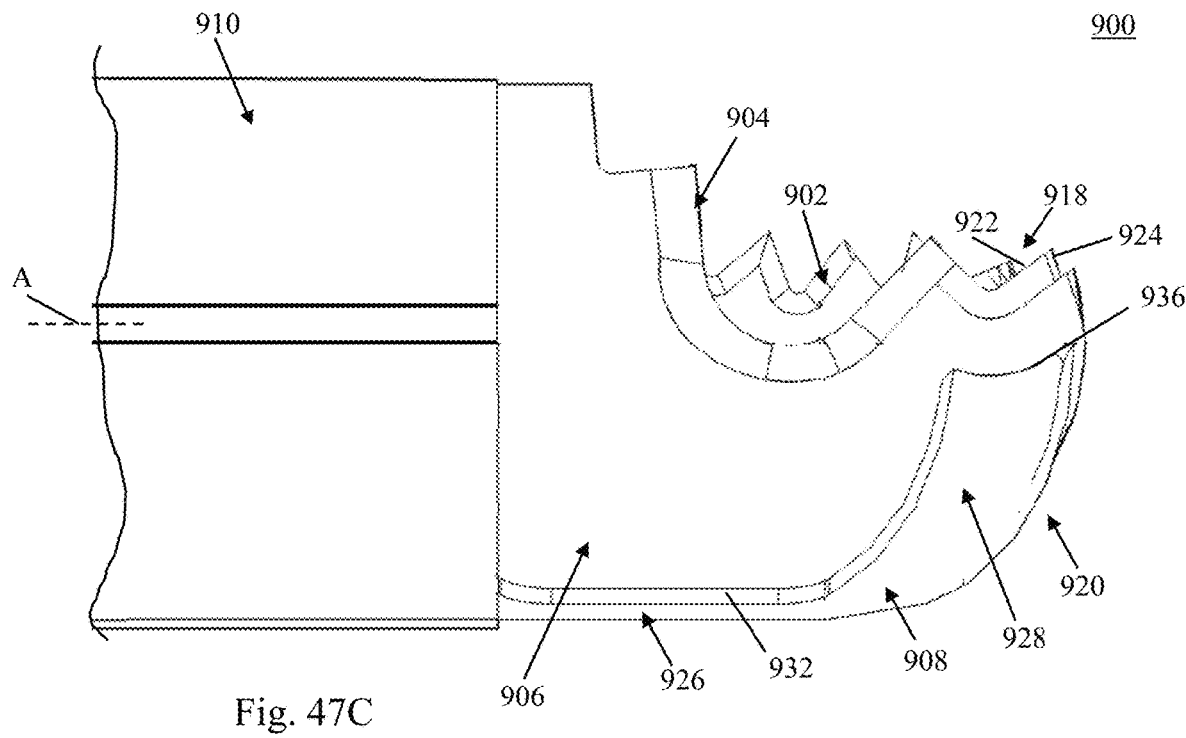
FIG. 47C is an enlarged side view of a portion of the device of FIG. 47A.
Figure 47D:
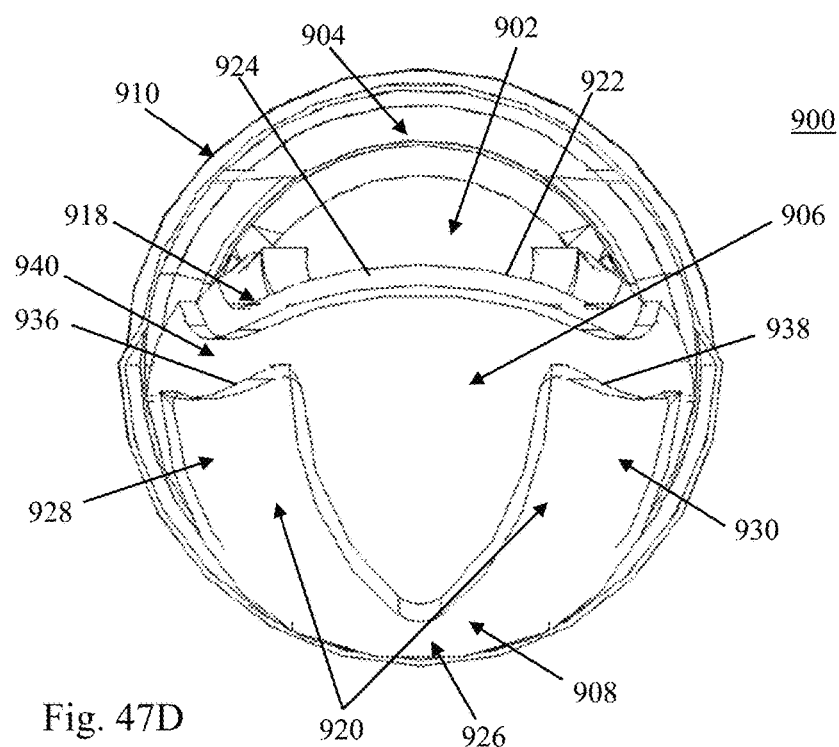
FIG. 47D is an enlarged front view of the device of FIG. 47A.

As shown in FIG. 44, fluid (e.g., saline) F delivered through the irrigation channel 772 (FIG. 43B) is dispensed to an exterior of the device 750 via the irrigation outlet port 774, and can progress into contact with the electrode surfaces 768, 770 to promote operation thereof in a bipolar mode as described above. With embodiments in which the device 750 provides suction or aspiration at the cutting tip 762 (e.g., as described above, a lumen of the inner shaft 752 can be connected to a suction source), the saline or other fluid F expressed from at least a portion of the irrigation outlet port 774 will not be immediately or primarily aspirated from the treatment site.

Regardless of how irrigation is provided, other aspects of the present disclosure relate to geometries of the first and second electrode surfaces. While previous embodiments have illustrated certain geometries and relationships of and between the electrode surfaces, other constructions are also envisioned. As a point of reference, bipolar cautery added to a debrider blade gives a surgeon the ability to control blood loss while resecting tissue. Used in sinus surgery, for example, that are several concerns that a surgeon has while using a cauterizing tool. First, the surgeon must have precise control over the location of cautery. Mucosal tissue in the sinuses is covered with cilia that is required for normal mucus flow and healthy sinus function. When mucosal tissue is thermally damaged, the cilia is permanently lost that can lead to additional sinus problems. Additionally, many sinus surgeries take place in close proximity to the eyes and brain; under these circumstances, precise control over the depth and spread of cauterization can be beneficial. In the embodiments below, various electrode surface geometries are disclosed that are useful with any of the electrical surgical devices of the present disclosure.

Portions of another electrical surgical device 800 in accordance with principles of the present disclosure are shown in FIGS. 45A-45D. In particular, blade and electrode assembly components of the device 800 are shown and described below. For ease of explanation, various other components of the device 800 are omitted from the views; for example, the device 800 can include one or more of the various housings, hubs and electrical connections components described above with respect to the device 110 (FIG. 2A), or equivalent components or mechanisms. Further, the device 800 can incorporate any of the irrigation constructions of the present disclosure. With this in mind, the device 800 includes an inner shaft or tubular member 802, an outer shaft or tubular member 804, an electrical insulator 806, a second electrode body or cap 808, and an insulating layer 810. Akin to the embodiments above, the inner shaft 802 is rotatably disposed within the outer shaft 804 and forms a cutting tip 812. The cutting tip 812 is selectively exposed at a cutting window 814 of the outer shaft 804. The cutting tip 812 and the cutting window 814 combine to define a cutting implement 816. The electrical insulator 806 covers a majority of an exterior of the outer shaft 804. The outer shaft 804 is formed of an electrically conductive material and thus can serve as a first electrode body of the device 800. A distal portion of the outer shaft 804 is free of the electrical insulator 806, defining a first electrode surface 818. The second electrode body 808 receives the outer shaft 804 (coated with the electrical insulator 806). The insulating layer 810 covers a majority of an exterior of the second electrode body 808, optionally securing the second electrode body 808 to the outer shaft 804 (e.g., via heat shrink process). A distal region of the second electrode body 808 is free of the insulating layer 810, defining a second electrode surface 820.

The device 800 operates in a manner highly akin to the device 110 (FIG. 2A) as described above, with the inner shaft 802 powered to rotate or oscillate relative to the outer shaft 804 to perform tissue cutting, dissection, etc., at the cutting implement 816. Further, the electrode surfaces 818, 820 can be operated as bipolar electrodes as described above.

The first electrode surface 818 includes the exposed perimeter face 822 of the outer shaft 804 circumscribing the cutting window 814. Further, a leading face 824 of the first electrode surface 818 is defined beyond the cutting window perimeter face 822 (i.e., the outer shaft 804 is free of the electrical insulator 806 at the leading face 824).

The second electrode surface 820 can have the frame- or rail-like configuration shown, and projects distally from the insulating layer 810. Projection of the second electrode surface 820 defines opposing, upper and lower edges 826, 828. A shape and contour of the upper edge 826 generally corresponds with a shape and contour of the first electrode surface 818 as shown. For example, a gap 830 is defined between the upper edge 826 of the second electrode surface 820 and the first electrode surface 818, with the gap 830 having a shape that mimics a shape of a perimeter edge of the first electrode surface 818. The electrical insulator 806 is exposed at the gap 830.

The frame-like construction of the second electrode surface 820 can be viewed as generating opposing, first and second side segments 832, 834 and a tip segment 836. The side segments 832, 834 extend in a generally longitudinal fashion along opposing sides of the device 800, respectively. The tip segment 836 follows the curved or arcuate shape of a distal end of the outer shaft 804, and extends between the side segments 832, 834. A width or height of the second electrode surface 820 can be larger along the tip segment 836 as compared to a width or height of the side segments 832, 834. The lower edge 828 is continuous or contiguous along the segments 832-836. As best identified in FIG. 45B, the second electrode surface 820 is incomplete or discontinuous relative to a bottom face of the device 800. Stated otherwise, an open region 838 is generated in the second electrode surface 820 at which the electrical insulator 806 is exposed. The lower edge 828 along the first side segment 832 is spaced from the lower edge 828 along the second side segment 834 by the open region 838.

With this construction, bipolar energization at the first and second electrode surfaces 818, 820 is generally focused to a region of the leading face 824 of the first electrode surface 818 and the tip segment 836 of the second electrode surface 820. Energization (e.g., cauterization, ablation, etc.) will not occur at the open region 838 (i.e., region where the second electrode surface 820 is not present). Thus, by eliminating material of the second electrode surface 820 on the "back" side of the blade assembly, the device 800 provides enhanced safety as unintentional tissue energization is prevented from occurring at the back side.

Portions of another electrical surgical device 850 in accordance with principles of the present disclosure are shown in FIGS. 46A-46D. In particular, blade and electrode assembly components of the device 850 are shown and described below. For ease of explanation, various other components of the device 850 are omitted from the views; for example, the device 850 can include one or more of the various housings, hubs and electrical connections components described above with respect to the device 110 (FIG. 2A), or equivalent components or mechanisms. Further, the device 850 can incorporate any of the irrigation constructions of the present disclosure. With this in mind, the device 850 includes an inner shaft or tubular member 852, an outer shaft or tubular member 854, an electrical insulator 856, a second electrode body or cap 858, and an insulating layer 860. Akin to the embodiments above, the inner shaft 852 is rotatably disposed within the outer shaft 854 and forms a cutting tip 862. The cutting tip 862 is selectively exposed at a cutting window 864 of the outer shaft 854. The cutting tip 862 and the cutting window 864 combine to define a cutting implement 866. The electrical insulator 856 covers a majority of an exterior of the outer shaft 854. The outer shaft 854 is formed of an electrically conductive material and thus can serve as a first electrode body of the device 850. A distal portion of the outer shaft 854 is free of the electrical insulator 856, defining a first electrode surface 868. The second electrode body 858 receives the outer shaft 854 (coated with the electrical insulator 856). The insulating layer 860 covers a majority of an exterior of the second electrode body 858, optionally securing the second electrode body 858 to the outer shaft 854 (e.g., via heat shrink process). A distal region of the second electrode body 858 is free of the insulating layer 860, defining a second electrode surface 870.

The device 850 operates in a manner highly akin to the device 110 (FIG. 2A) as described above, with the inner shaft 852 powered to rotate or oscillate relative to the outer shaft 854 to perform tissue cutting, dissection, etc., at the cutting implement 866. Further, the electrode surfaces 868, 870 can be operated as bipolar electrodes as described above.

The first electrode surface 868 includes the exposed perimeter face 872 of the outer shaft 854 circumscribing the cutting window 864. Further, a leading face 874 of the first electrode surface 868 is defined beyond the cutting window perimeter face 872 (i.e., the outer shaft 854 is free of the electrical insulator 856 at the leading face 874).

The second electrode surface 870 can have the rib-like configuration shown, and projects distally from the insulating layer 860. Projection of the second electrode surface 870 defines opposing side edges 876, 878 and a tip edge 880. A shape and contour of the second electrode surface 870 is such that the opposing side edges 876, 878 can be substantially linear or straight, extending substantially parallel with a central axis of the outer shaft 856. Further, the opposing side edges 876, 878 are distinctly spaced from a corresponding (i.e., closest) edge of the first electrode surface 868. The second electrode surface 870 mimics or follows a curvature of a distal end of the outer shaft 856, and locates the tip edge 880 in relatively close proximity to the leading face 874 of the first electrode surface 868. Stated otherwise, while a gap 882 exists between the leading face 874 of the first electrode surface 868 and the tip edge 880 of the second electrode surface 870 (at which the electrical insulator 806 is exposed), a distance between the leading face 874 and the tip edge 880 is substantially less than a distance between the side edges 876, 878 and corresponding (i.e., closest) edge of the first electrode surface 868. For example, in some embodiments, a distance between the tip edge 880 and the first electrode surface 868 is at least 25% less than the distance between at least a majority of the first or second side edges 876, 878 and the first electrode surface 868, alternatively at least 30% less, or at least 50% less.

With this construction, bipolar energization at the first and second electrode surfaces 868, 870 is generally focused to a region of the leading face 874 of the first electrode surface 868 and the tip edge 880 of the second electrode surface 870. Energization (e.g., cauterization, ablation, etc.) will is much less likely to occur at the sides of the second electrode surface 870 or "back" of the blade assembly, providing enhanced safety as unintentional tissue energization is prevented from occurring at the back side. Further, a precise cautery effect is promoted at the tip of the blade assembly.

Portions of another electrical surgical device 900 in accordance with principles of the present disclosure are shown in FIGS. 47A-47D. In particular, blade and electrode assembly components of the device 900 are shown and described below. For ease of explanation, various other components of the device 900 are omitted from the views; for example, the device 900 can include one or more of the various housings, hubs and electrical connections components described above with respect to the device 110 (FIG.

2A), or equivalent components or mechanisms. Further, the device 900 can incorporate any of the irrigation constructions of the present disclosure. With this in mind, the device 900 includes an inner shaft or tubular member 902, an outer shaft or tubular member 904, an electrical insulator 906, a second electrode body or cap 908, and an insulating layer 910. Akin to the embodiments above, the inner shaft 902 is rotatably disposed within the outer shaft 904 and forms a cutting tip 912. The cutting tip 912 is selectively exposed at a cutting window 914 of the outer shaft 904. The cutting tip 912 and the cutting window 914 combine to define a cutting implement 916. The electrical insulator 906 covers a majority of an exterior of the outer shaft 904. The outer shaft 904 is formed of an electrically conductive material and thus can serve as a first electrode body of the device 900. A distal portion of the outer shaft 904 is free of the electrical insulator 906, defining a first electrode surface 918. The second electrode body 908 receives the outer shaft 904 (coated with the electrical insulator 906). The insulating layer 910 covers a majority of an exterior of the second electrode body 908, optionally securing the second electrode body 908 to the outer shaft 904 (e.g., via heat shrink process). A distal region of the second electrode body 908 is free of the insulating layer 910, defining a second electrode surface 920.

The device 900 operates in a manner highly akin to the device 110 (FIG. 2A) as described above, with the inner shaft 902 powered to rotate or oscillate relative to the outer shaft 904 to perform tissue cutting, dissection, etc., at the cutting implement 916. Further, the electrode surfaces 918, 920 can be operated as bipolar electrodes as described above.

The first electrode surface 918 includes the exposed perimeter face 922 of the outer shaft 904 circumscribing the cutting window 914. Further, a leading face 924 of the first electrode surface 918 is defined beyond the cutting window perimeter face 922 (i.e., the outer shaft 904 is free of the electrical insulator 906 at the leading face 924).

The second electrode surface 920 projects distally beyond the insulating layer 910, and forms or defines a base segment 926 and opposing, first and second tab segments 928, 930. The base segment 926 is generally arranged opposite the cutting window 924 and defines opposing side edges 932, 934. Extension of the base segment 926 can be substantially parallel with a central axis A of the outer shaft 904. Regardless, the side edges 932, 934 are substantively spaced from a corresponding (i.e., closest) edge of the first electrode surface 918. The tab segments 928, 930 can be substantially identical (e.g., mirror images), and project from the base segment 926 in a direction off-set from the central axis A while following a shape and contour of the distal end of the outer shaft 904. The tab segments 928, 930 each terminate in a tip edge 936, 938, respectively, that is located proximate the leading face 924 of the first electrode surface 918. As best reflected by FIG. 47D, the tip edges 936, 938 are radially off-set or off-axis from the central axis A, with the tip edge 936 of the first tab segment 928 located at one side of the central axis A and the tip edge 938 of the second tab segment 930 located at an opposite side of the central axis. While a gap 940 exists between the leading face 924 of the first electrode surface 918 and the tip edges 936, 938 of the second electrode surface 920 (at which the electrical insulator 906 is exposed), a distance between the leading face 924 and the tip edges 936, 938 is substantially less than a distance between any other edges of the second electrode surface 920 and corresponding (i.e., closest) edge of the first electrode surface 918. For example, in some embodiments, a distance between the tip edges 936, 938 and the first electrode surface 918 is at least 25% less than the distance between a remainder of the second electrode surface 920 and the first electrode surface 918, alternatively at least 30% less, or at least 50% less.

With this construction, bipolar energization at the first and second electrode surfaces 918, 920 is generally focused to a region of the leading face 924 of the first electrode surface 918 and the off-set tip edges 936, 938 of the second electrode surface 920. Energization (e.g., cauterization, ablation, etc.) is less likely to occur at the "back" of the blade assembly, providing enhanced safety as unintentional tissue energization is prevented from occurring at the back side. Further, a precise cautery control is promoted at the off-axis tips of the blade assembly; this effect can be beneficial, for example, with procedures in which an off-axis electrode is desired to access the target anatomy.

Figure 48A:
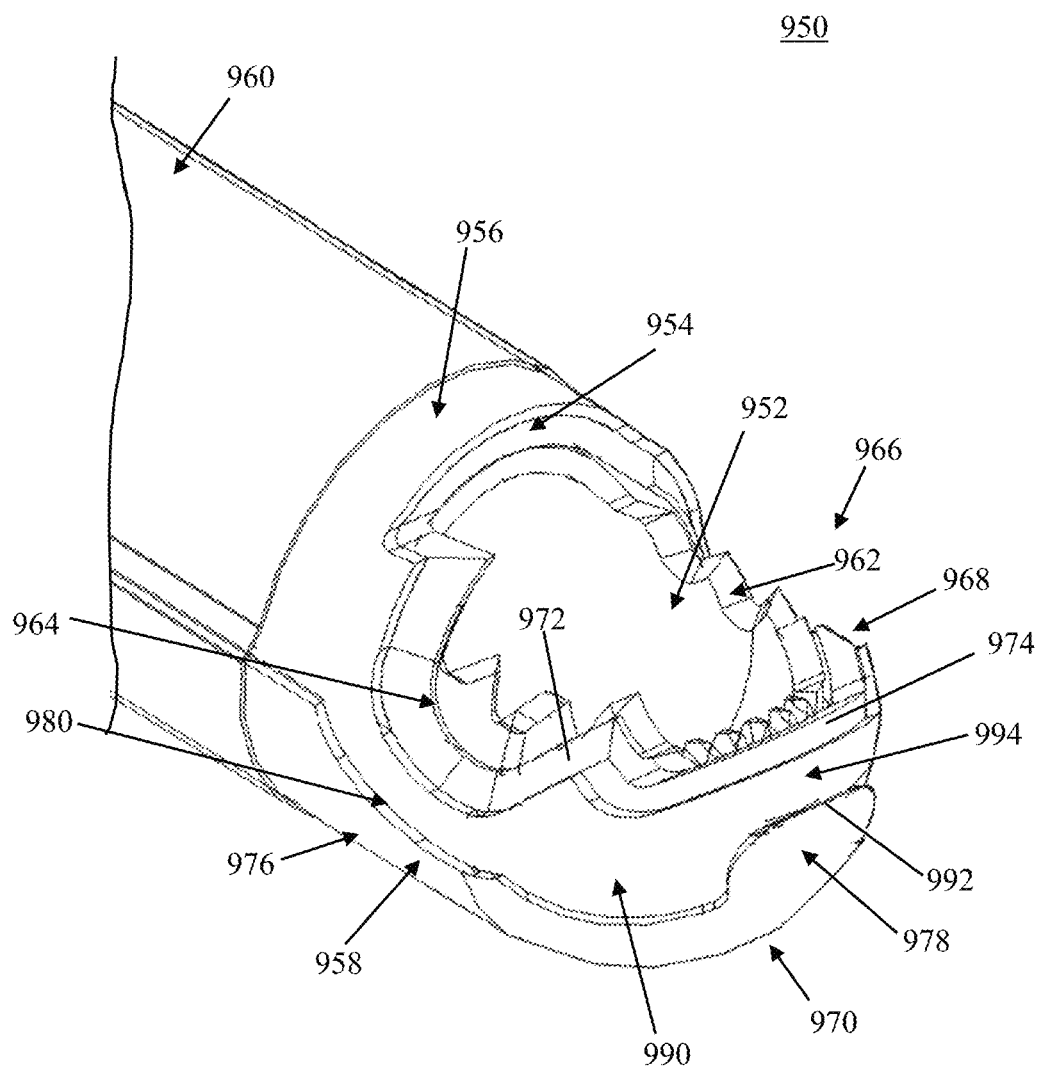
FIG. 48A is an enlarged, top perspective view of a portion of another bipolar electrical surgical device in accordance with principles of the present disclosure.
Figure 48B:
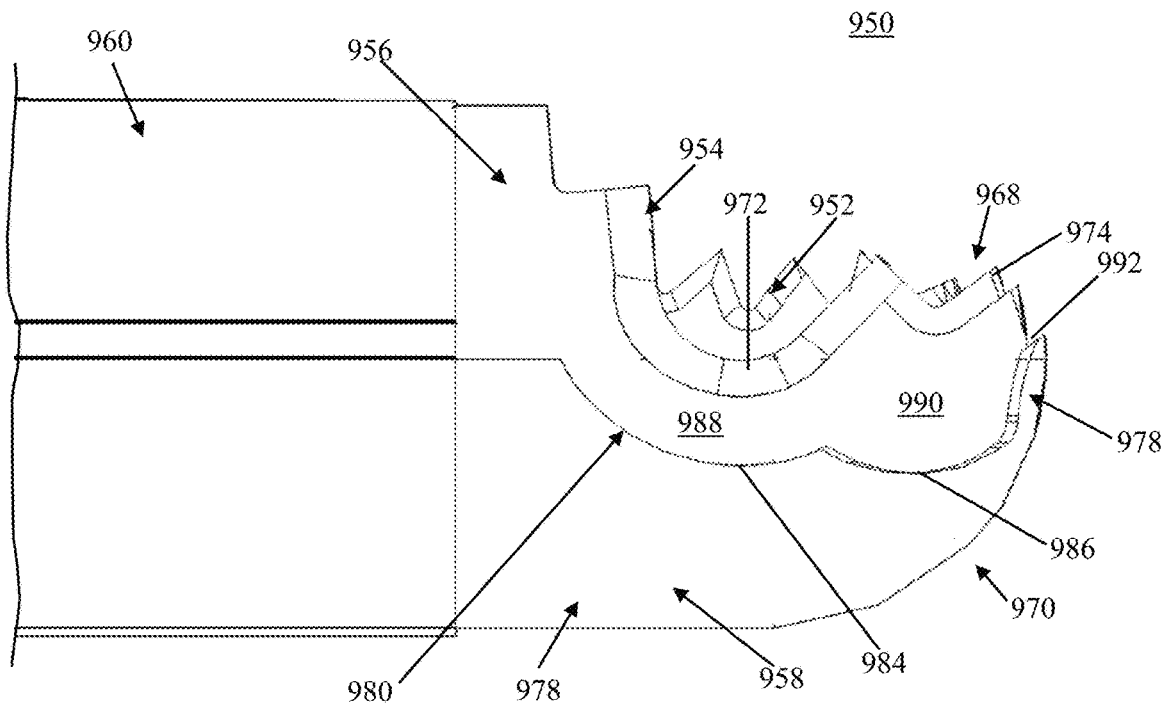
FIG. 48B is an enlarged side view of a portion of the device of FIG. 48A.
Figure 48C:
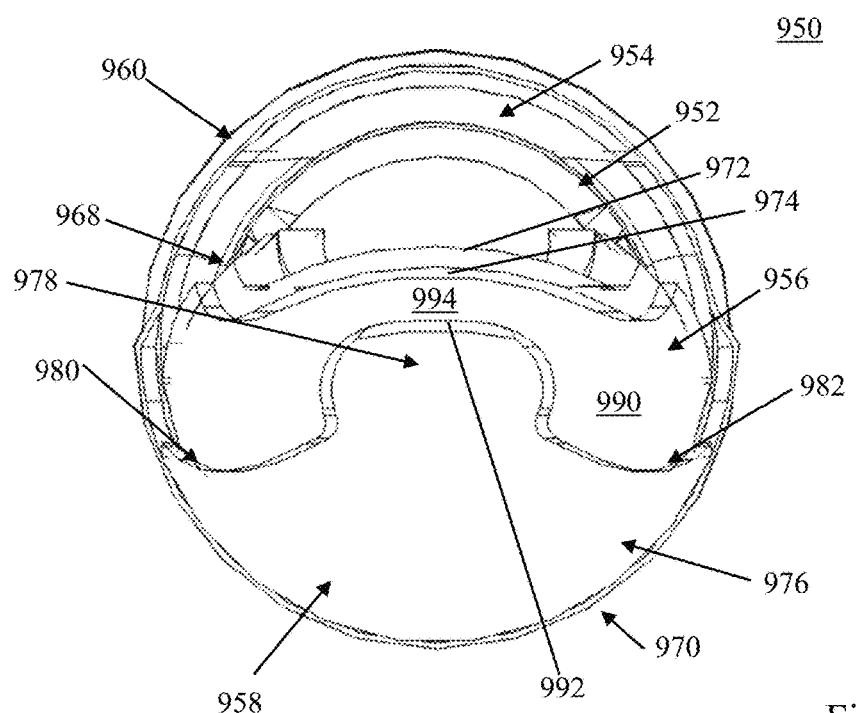
FIG. 48C is an enlarged front view of the device of FIG. 48A.

Portions of another electrical surgical device 950 in accordance with principles of the present disclosure are shown in FIGS. 48A-48C. In particular, blade and electrode assembly components of the device 950 are shown and described below. For ease of explanation, various other components of the device 950 are omitted from the views; for example, the device 950 can include one or more of the various housings, hubs and electrical connections components described above with respect to the device 110 (FIG. 2A), or equivalent components or mechanisms. Further, the device 950 can incorporate any of the irrigation constructions of the present disclosure. With this in mind, the device 950 includes an inner shaft or tubular member 952, an outer shaft or tubular member 954, an electrical insulator 956, a second electrode body or cap 958, and an insulating layer 960. Akin to the embodiments above, the inner shaft 952 is rotatably disposed within the outer shaft 954 and forms a cutting tip 962. The cutting tip 962 is selectively exposed at a cutting window 964 of the outer shaft 954. The cutting tip 962 and the cutting window 964 combine to define a cutting implement 966. The electrical insulator 966 covers a majority of an exterior of the outer shaft 954. The outer shaft 954 is formed of an electrically conductive material and thus can serve as a first electrode body of the device 950. A distal portion of the outer shaft 954 is free of the electrical insulator 956, defining a first electrode surface 968. The second electrode body 958 receives the outer shaft 954 (coated with the electrical insulator 956). The insulating layer 960 covers a majority of an exterior of the second electrode body 958, optionally securing the second electrode body 958 to the outer shaft 954 (e.g., via heat shrink process). A distal region of the second electrode body 958 is free of the insulating layer 960, defining a second electrode surface 970.

The device 950 operates in a manner highly akin to the device 110 (FIG. 2A) as described above, with the inner shaft 952 powered to rotate or oscillate relative to the outer shaft 954 to perform tissue cutting, dissection, etc., at the cutting implement 966. Further, the electrode surfaces 968, 970 can be operated as bipolar electrodes as described above.

The first electrode surface 968 includes the exposed perimeter face 972 of the outer shaft 954 circumscribing the cutting window 964. Further, a leading face 974 of the first electrode surface 968 is defined beyond the cutting window perimeter face 972 (i.e., the outer shaft 954 is free of the electrical insulator 956 at the leading face 974).

The second electrode surface 970 projects distally beyond the insulating layer 960, and forms or defines a base segment 976 and a tip segment 978. The base segment 976 is generally arranged opposite the cutting window 964 and defines opposing side edges 980, 982. The side edges 980, 982 can have identical shapes. For example, a shape of the first side edge 980 is shown in FIG. 48B as defining a proximal region 984 and a distal region 986. A shape of the proximal region 984 can mimic a shape of the corresponding (i.e., closest) edge of the first electrode surface 968, such that a first spacing 988 between the first side edge 980 and the first electrode surface 968 (along the proximal region 984) is relatively uniform. The side edge 980 projects away from the first electrode surface 968 along the distal region 986, establishing an enlarged, second spacing 990 between the first side edge 980 and the first electrode surface 968 in the distal direction. A size of the second spacing 990 is greater than a size of the first spacing 988. Stated otherwise, a distance between the first side edge 980 and the corresponding (i.e., closest) edge of the first electrode surface 968 along the distal region 986 is greater than that along the proximal region 984.

The tip segment 978 follows a curvature of the distal end of the outer shaft 954, and projects upwardly toward the first electrode surface 968. The tip segment 978 terminates at a tip edge 992 that is proximate the leading face 974 of the first electrode surface 968. While a gap 994 exists between the leading face 974 of the first electrode surface 968 and the tip edge 992 of the second electrode surface 970 (at which the electrical insulator 956 is exposed), a distance between the leading face 974 and the tip edge 992 is substantially less than a distance between the side edges 980, 982 and corresponding (i.e., closest) edge of the first electrode surface 968, at least along the corresponding distal region 986. Stated otherwise a size of the gap 994 at the tip edge 992 is substantially less than a size of the second spacing 990 at the distal region 986. For example, in some embodiments, a distance between the tip edge 992 and the first electrode surface 968 is at least 25% less than the distance between side edges 980, 982 along the distal region 986 and the corresponding (i.e., closest) edge of the first electrode surface 968, alternatively at least 30% less, or at least 50% less.

With this construction, bipolar energization at the first and second electrode surfaces 968, 970 is generally focused to a region of the leading face 974 of the first electrode surface 968 and the tip edge 992 of the second electrode surface 970, and at opposing side regions corresponding with the proximal regions 984 of the second electrode surface 970. The energization (e.g., cauterization, ablation, etc.) effect is concentrated at the tip and sides of the blade assembly. Greater cautery precision is afforded during side and tip led cuts when the device 950 is used in simultaneous debride/cauterize procedures.

Figure 49A:
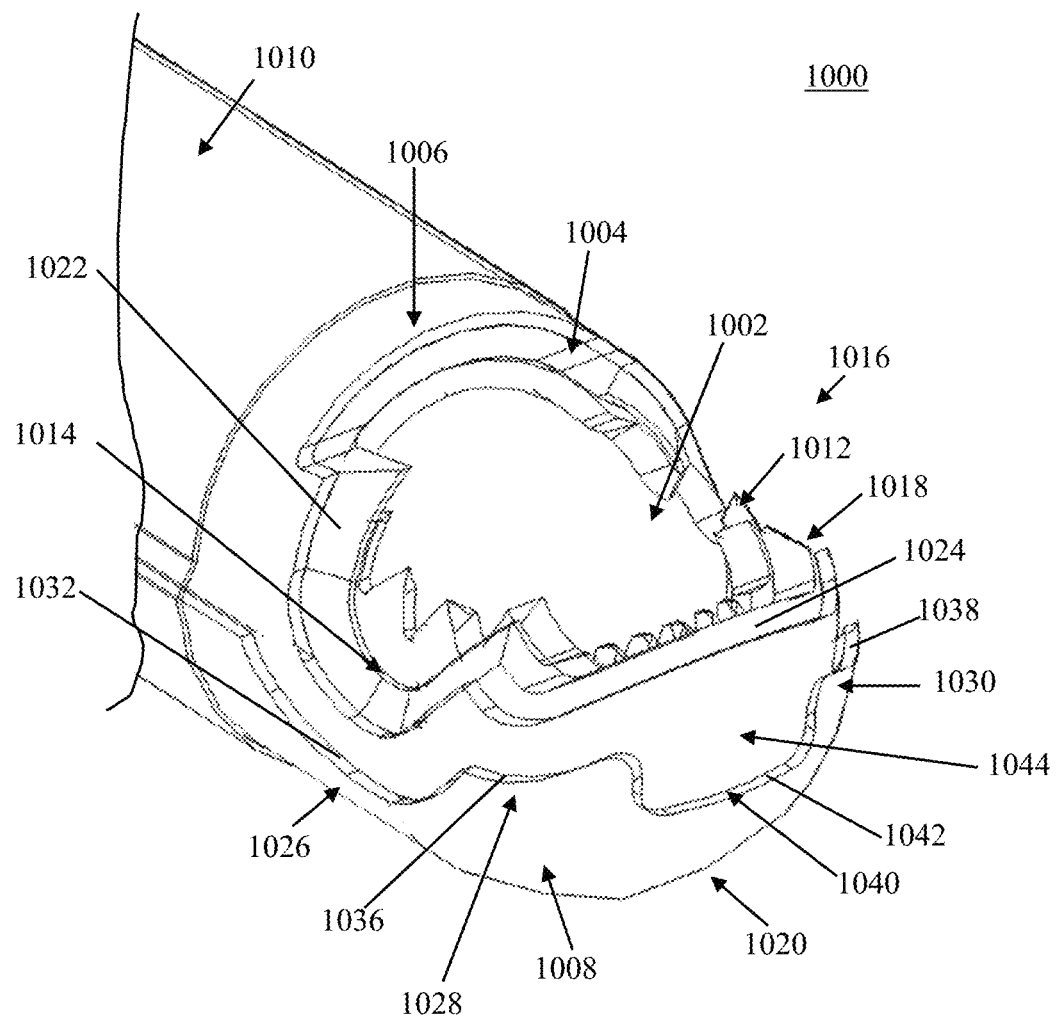
FIG. 49A is an enlarged, top perspective view of a portion of another bipolar electrical surgical device in accordance with principles of the present disclosure.
Figure 49B:
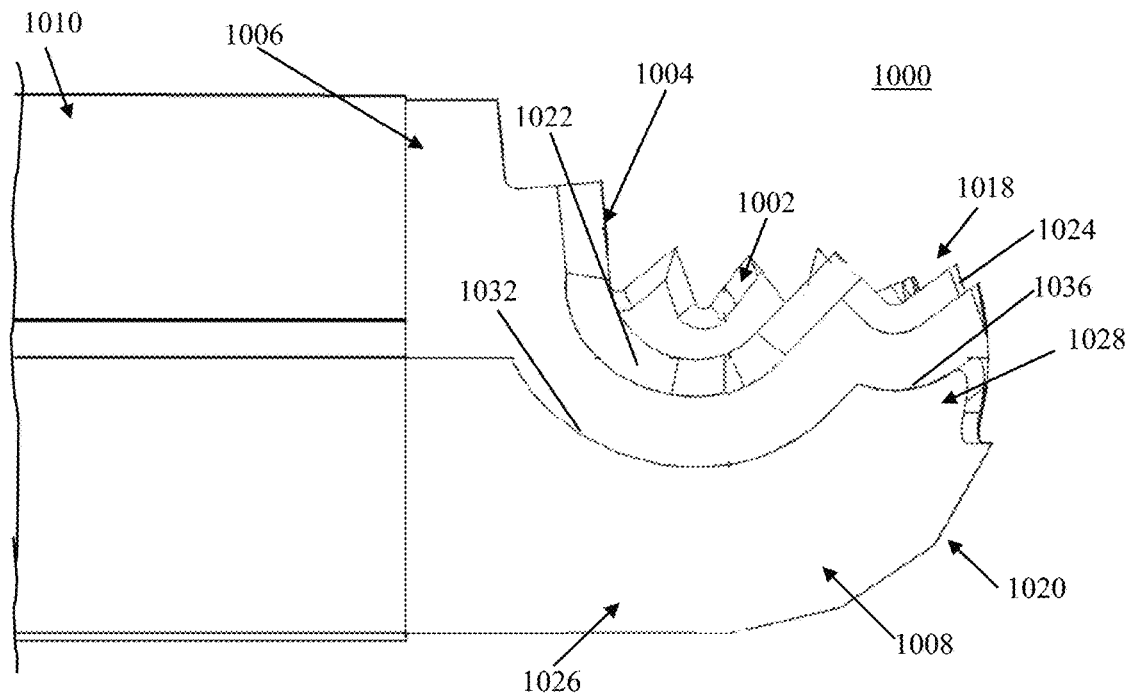
FIG. 49B is an enlarged side view of a portion of the device of FIG. 49A.
Figure 49C:
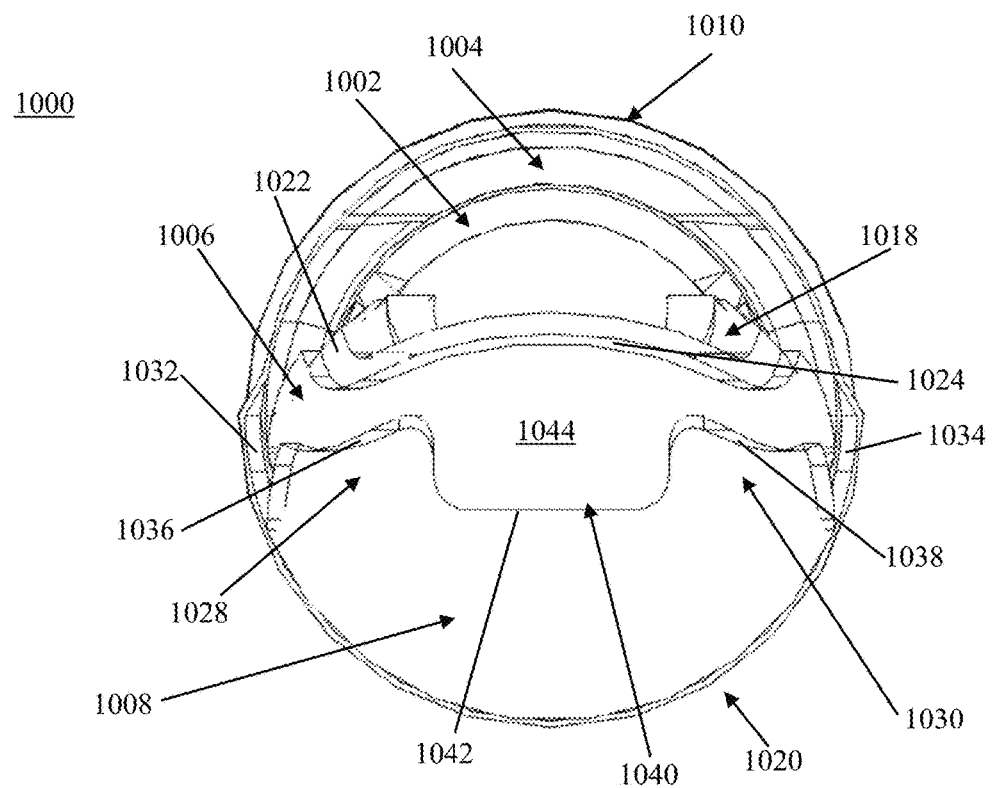
FIG. 49C is an enlarged front view of the device of FIG. 49A.

Portions of another electrical surgical device 1000 in accordance with principles of the present disclosure are shown in FIGS. 49A-49C. In particular, blade and electrode assembly components of the device 1000 are shown and described below. For ease of explanation, various other components of the device 1000 are omitted from the views; for example, the device 1000 can include one or more of the various housings, hubs and electrical connections components described above with respect to the device 110 (FIG. 2A), or equivalent components or mechanisms. Further, the device 1000 can incorporate any of the irrigation constructions of the present disclosure. With this in mind, the device 1000 includes an inner shaft or tubular member 1002, an outer shaft or tubular member 1004, an electrical insulator 1006, a second electrode body or cap 1008, and an insulating layer 1010. Akin to the embodiments above, the inner shaft 1002 is rotatably disposed within the outer shaft 1004 and forms a cutting tip 1012. The cutting tip 1012 is selectively exposed at a cutting window 1014 of the outer shaft 1004. The cutting tip 1012 and the cutting window 1014 combine to define a cutting implement 1016. The electrical insulator 1006 covers a majority of an exterior of the outer shaft 1004. The outer shaft 1004 is formed of an electrically conductive material and thus can serve as a first electrode body of the device 1000. A distal portion of the outer shaft 1004 is free of the electrical insulator 1006, defining a first electrode surface 1018. The second electrode body 1008 receives the outer shaft 1004 (coated with the electrical insulator 1006). The insulating layer 1010 covers a majority of an exterior of the second electrode body 1008, optionally securing the second electrode body 1008 to the outer shaft 1004 (e.g., via heat shrink process). A distal region of the second electrode body 1008 is free of the insulating layer 1010, defining a second electrode surface 1020.

The device 1000 operates in a manner highly akin to the device 110 (FIG. 2A) as described above, with the inner shaft 1002 powered to rotate or oscillate relative to the outer shaft 1004 to perform tissue cutting, dissection, etc., at the cutting implement 1016. Further, the electrode surfaces 1018, 1020 can be operated as bipolar electrodes as described above.

The first electrode surface 1018 includes the exposed perimeter face 1022 of the outer shaft 1004 circumscribing the cutting window 1014. Further, a leading face 1024 of the first electrode surface 1018 is defined beyond the cutting window perimeter face 1022 (i.e., the outer shaft 1004 is free of the electrical insulator 1006 at the leading face 1024).

The second electrode surface 1020 projects distally beyond the insulating layer 1010, and forms or defines a base 1026 and opposing tabs 1028, 1030. The base segment 1026 is generally arranged opposite the cutting window 1014 and defines opposing side edges 1032, 1034. The side edges 1032, 1034 can have identical shapes. For example, a shape of the first side edge 1032 is shown in FIG. 49B as mimicking or following a shape of the corresponding (i.e., closest) edge of the first electrode surface 1018, such that a relatively uniform spacing is established between the side edges 1032, 1034 and the first electrode surface 1018.

The opposing tabs 1028, 1030 generally follow a curvature of the distal end of the outer shaft 1004, and each terminate at a tip edge 1036, 1038, respectively. A shape of each of the tip edges 1036, 1038 mimics or follows a shape of the corresponding (i.e., closest) edge of the first electrode surface 1018, such as a shape of the leading face 1024. A notch 1040 is formed in the second electrode surface 1020 between the opposing tabs 1028, 1030 (e.g., the tabs 1028, 1030 are defined at opposite sides of a central axis of the outer shaft 1006). The notch 1040 defines a recessed leading edge 1042 of the second electrode surface 1020. An enlarged spacing or gap 1044 (at which the electrical insulator 1006 is exposed) is generated between the recessed leading edge 1042 of the second electrode surface 1020 and the leading face 1024 of the first electrode surface 1018. A size of the gap 1044 is greater than a size of the spacing between the first electrode surface 1018 and other edges of the second electrode surface 1020. Stated otherwise, a distance between the recessed leading edge 1042 of the second electrode surface 1020 and the leading face 1024 of the first electrode surface 1018 is greater than the distance between the tip edges 1036, 1038 and the corresponding (i.e., closest) edge (e.g., the leading face 1024) of the first electrode surface 1018, and is greater than the distance between the side edges 1032, 1034 and the corresponding (i.e., closest) edge of the first electrode surface 1018.

With this construction, bipolar energization at the first and second electrode surfaces 1018, 1020 is generally focused to a region of the leading face 1024 of the first electrode surface 1018 and the off-set tip edges 1036, 1038 of the second electrode surface 1020. Enhanced safety is provided by concentrating off-axis cautery (or other electrical stimulation) and reducing cautery effect at the tip for procedures where the tip cannot be visualized.

Portions of another electrical surgical device 1050 in accordance with principles of the present disclosure are shown in FIGS. 50A-50D. In particular, blade and electrode assembly components of the device 1050 are shown and described below. For ease of explanation, various other components of the device 1050 are omitted from the views; for example, the device 1050 can include one or more of the various housings, hubs and electrical connections components described above with respect to the device 110 (FIG. 2A), or equivalent components or mechanisms. Further, the device 1050 can incorporate any of the irrigation constructions of the present disclosure. With this in mind, the device 1050 includes an inner shaft or tubular member 1052, an outer shaft or tubular member 1054, an electrical insulator 1056, a second electrode body or cap 1058, and an insulating layer 1060. Akin to the embodiments above, the inner shaft 1052 is rotatably disposed within the outer shaft 1054 and forms a cutting tip 1062. The cutting tip 1062 is selectively exposed at a cutting window 1064 of the outer shaft 1054. The cutting tip 1062 and the cutting window 1064 combine to define a cutting implement 1066. The electrical insulator 1056 covers a majority of an exterior of the outer shaft 1054. The outer shaft 1054 is formed of an electrically conductive material and thus can serve as a first electrode body of the device 1050. A distal portion of the outer shaft 1054 is free of the electrical insulator 1056, defining a first electrode surface 1068. The second electrode body 1058 receives the outer shaft 1054 (coated with the electrical insulator 1056). The insulating layer 1060 covers a majority of an exterior of the second electrode body 1058, optionally securing the second electrode body 1058 to the outer shaft 1054 (e.g., via heat shrink process). A distal region of the second electrode body 1058 is free of the insulating layer 1060, defining a second electrode surface 1070.

The device 1050 operates in a manner highly akin to the device 110 (FIG. 2A) as described above, with the inner shaft 1052 powered to rotate or oscillate relative to the outer shaft 1054 to perform tissue cutting, dissection, etc., at the cutting implement 1066. Further, the electrode surfaces 1068, 1070 can be operated as bipolar electrodes as described above.

The first electrode surface 1068 includes the exposed perimeter face 1072 of the outer shaft 1054 circumscribing the cutting window 1064.

The second electrode surface 1070 projects distally beyond the insulating layer 1060, and forms or defines a base 1074 and opposing tabs 1076, 1078. The base 1074 is generally arranged toward the cutting window 1064 and defines a back edge 1080. A shape of the back edge 1080 mimics or follows a shape of the corresponding (i.e., closest) edge of the first electrode surface 1068 (e.g., that portion of the perimeter face 1072 immediately adjacent the back edge 1080), such that a relatively uniform spacing is established between the back edge 1080 and the first electrode surface 1068.

Figure 50B:
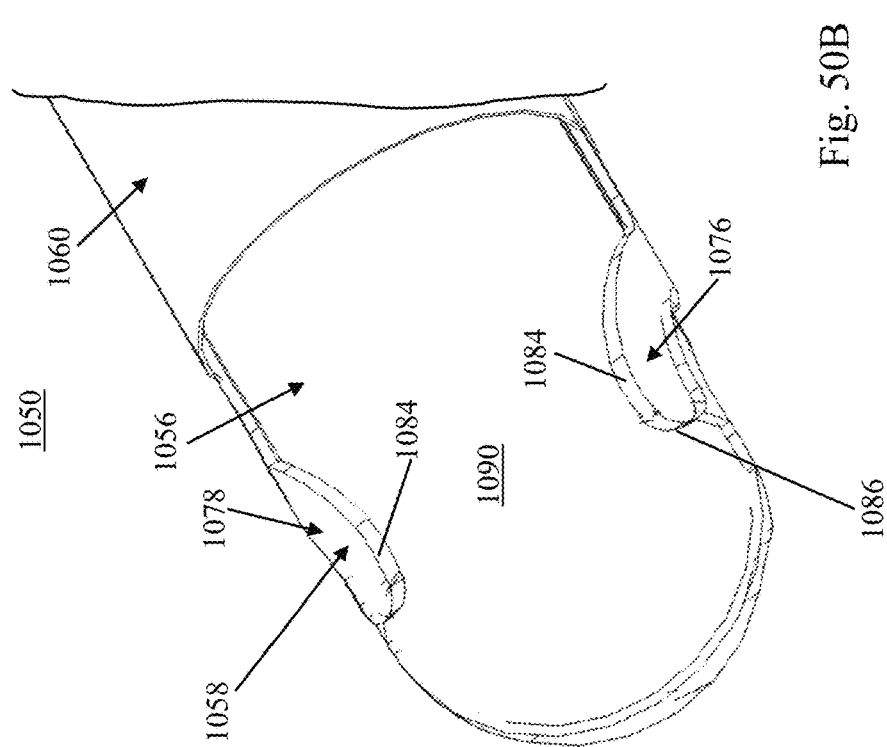
FIG. 50B is a bottom perspective view of the device of FIG. 50A.
Figure 50A:
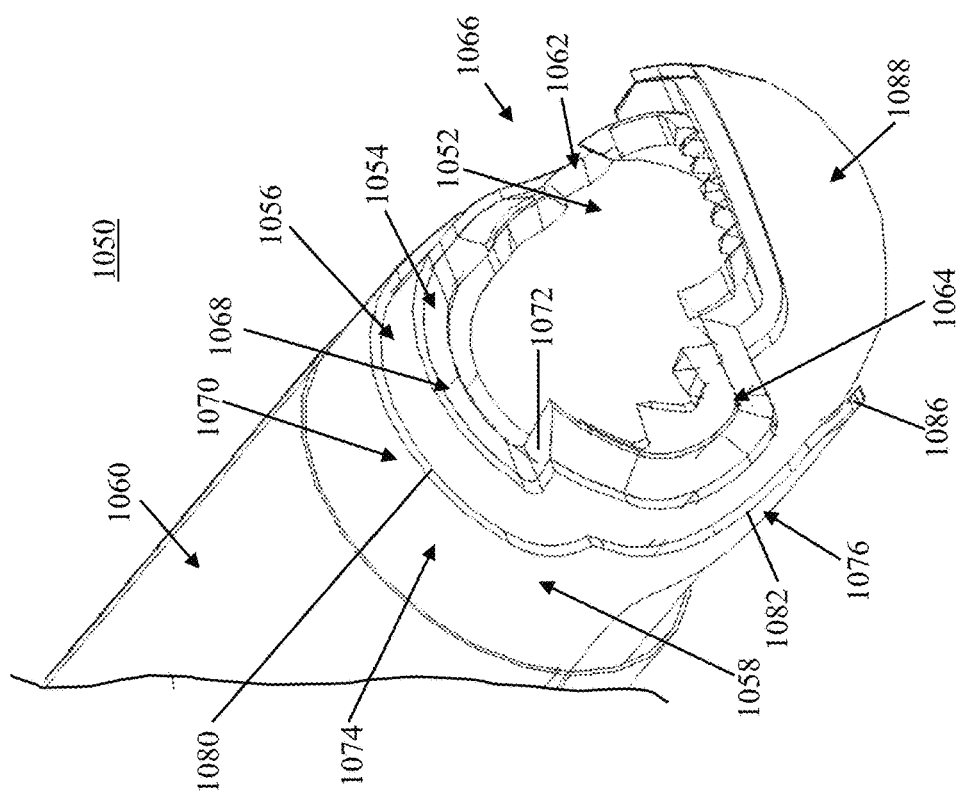
FIG. 50A is an enlarged, top perspective view of a portion of another bipolar electrical surgical device in accordance with principles of the present disclosure.
Figure 50C:
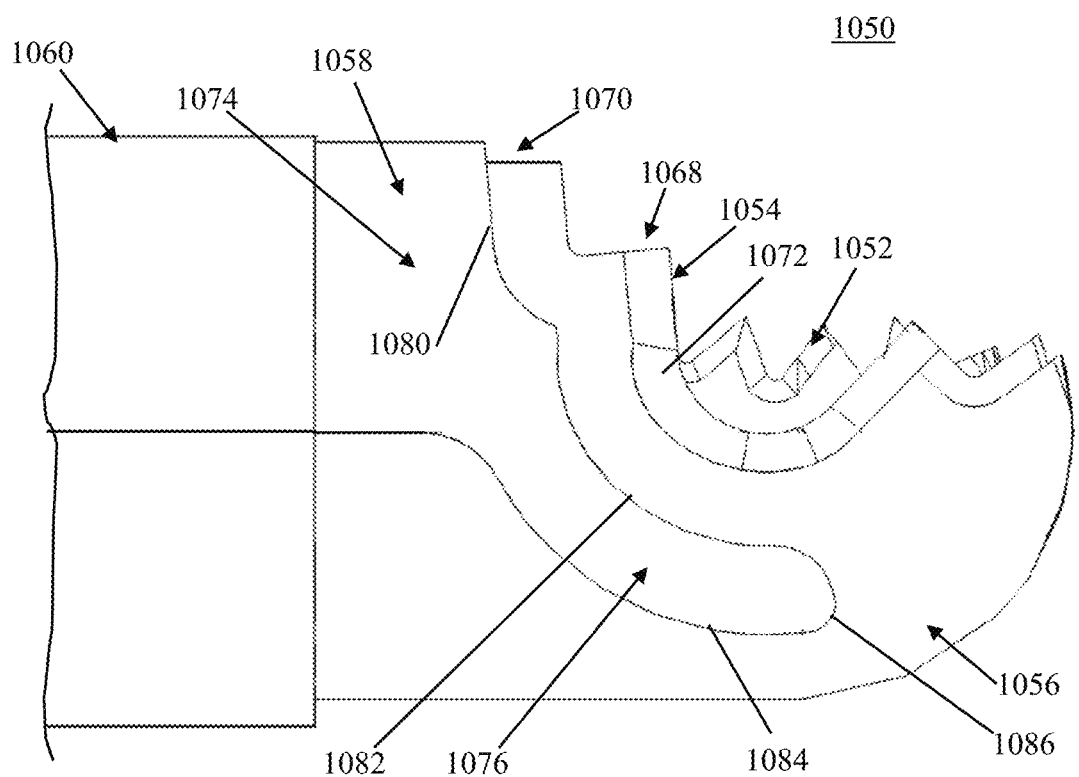
FIG. 50C is an enlarged side view of a portion of the device of FIG. 50A.
Figure 50D:
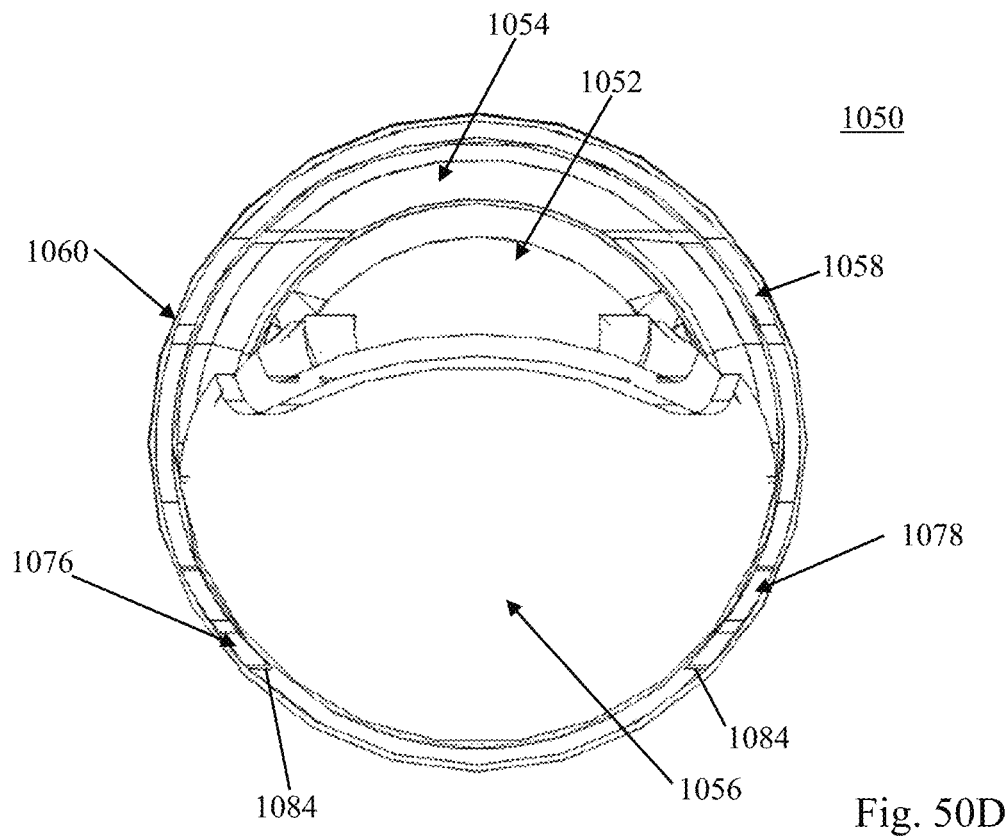
FIG. 50D is an enlarged front view of the device of FIG. 50A.

The tabs 1076, 1078 can be identical in shape, projecting from the base 1074 at opposite sides of the cutting window 1064. Each tab defines an upper edge 1082 opposite a lower edge 1084, and terminates at a tip edge 1086. A shape of the 1082 mimics or follows a shape of the corresponding (i.e., closest) edge of the first electrode surface 1068 (e.g., that portion of the perimeter face 1072 immediately adjacent the respective upper edge 1082). The tabs 1076, 1078 do not extend to (or about) the distal end of the outer shaft 1054; the tip edge 1086 of each of the tabs 1076, 1078 is proximal the distal end of the outer shaft 1054. As best shown in FIG. 50A, a distal insulated region 1088 is generated at which the second electrode surface 1070 does not exist and at which the electrical insulator 1056 is exposed. Further, and as best reflected by FIG. 50B, the opposing lower edges 1084 of the tabs 1076, 1078 are circumferentially spaced from one another. Thus, a substantive open region 1090 is defined between the tabs 1076, 1078 and at which the electrical insulator 1056 is exposed.

With this construction, bipolar energization at the first and second electrode surfaces 1068, 1070 is generally focused to a proximal region of the first electrode surface 1068. Enhanced safety is provided for procedures where the tip cannot be visualized.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A bipolar electrical device, comprising: an outer shaft defining a lumen extending along a central axis, a proximal end and a distal end opposite the proximal end, wherein the distal end forms a cutting window open to the lumen; an inner shaft rotatably disposed within the lumen of the outer shaft about the central axis, the inner shaft defining a distal portion forming a cutting tip; Wherein the cutting tip and the cutting window combine to define a cutting implement; and first and second electrically isolated electrode surfaces formed at the cutting implement; an irrigation channel extending parallel to the outer shaft, the irrigation channel terminating in at least one outlet port proximally spaced from the cutting window and located on an outer surface of the outer shaft.

2. The device of claim 1, wherein the outer shaft serves as a first electrode body defining the first electrically isolated electrode surface.

3. The device of claim 2, further comprising a second electrode body connected to the outer shaft and defining the second electrically isolated electrode surface.

4. The device of claim 3, further comprising an electrical insulator disposed over the outer shaft to electrically isolate the outer shaft and the second electrode body.

5. The device of claim 4, wherein at least a portion of the cutting window is free of the electrical insulator such that the at least a portion of the cutting window defines at least a portion of the first electrode surface.

6. The device of claim 5, further comprising an insulating layer disposed about the second electrode body and the outer shaft.

7. The device of claim 6, wherein at least a portion of the second electrode body is free of the insulating layer to form the second electrode surface.

8. The device of claim 1, wherein the irrigation channel is defined by a spacing between the inner and outer shafts.

9. The device of claim 8, wherein the at least one outlet port includes a weep hole.

10. The device of claim 8, wherein the at least one outlet port is formed by a porous material.

11. The device of claim 8, wherein the at least one outlet port includes a hole formed in the outer shaft.

12. The device of claim 11, further comprising an electrical insulator disposed over the outer shaft, wherein a region of the outer shaft is free of the electrical insulator to define the first electrode surface, and further wherein the at least one outlet port includes a hole formed through a thickness of the electrical insulator.

13. The device of claim 12, wherein the hole formed in the outer shaft is aligned with the hole formed through the thickness of the electrical insulator.

14. The device of claim 12, further comprising a second electrode body at least partially surrounding the outer shaft, and an insulating layer disposed about the second electrode body and the outer shaft, and further wherein the at least one outlet port includes a hole formed through a thickness of the insulating layer.

15. The device of claim 14, wherein the hole formed in the outer shaft, the hole formed through the thickness of the electrical insulator and the hole formed through the thickness of the insulating layer are aligned.

16. The device of claim 15, wherein the second electrode body defines the second electrode surface, and further wherein the at least one outlet port does not include a hole through the second electrode body.

17. The device of claim 8, further comprising an electrical insulator applied to the outer shaft, and a second electrode body connected to the outer shaft and defining the second electrode surface, wherein the at least one outlet port includes a hole formed through a thickness of the outer shaft, and the at least one outlet port opens to the irrigation channel, and further wherein the irrigation channel is defined between an outer surface of the electrical insulator and an inner surface of the second electrode body.

18. The device of claim 8, wherein a radial spacing between the inner shaft and the outer shaft distal the at least one outlet port is less than the radial spacing between the inner shaft and the outer shaft at the at least one outlet port.

19. The device of claim 1, further comprising an electrical insulator applied over the outer shaft, and further wherein the irrigation channel is defined by an inner surface of the electrical insulator and the outer surface of the outer shaft.

20. The device of claim 1, wherein the irrigation channel and the at least one outlet port proximally spaced from the cutting window are configured such that a majority of liquid within the irrigation channel exits the irrigation channel via the at least one outlet port proximally spaced from the cutting window.

21. The device of claim 20, wherein the device comprises a single outlet port and a single irrigation channel.

* * * * *